United States Patent
Waeber et al.

(10) Patent No.: US 6,620,914 B1
(45) Date of Patent: *Sep. 16, 2003

(54) TRANSCRIPTION FACTOR ISLET-BRAIN 1 (IB1)

(75) Inventors: Gerard Waeber, Chemin de la Rueyre 59, Jouxtens (CH), CH-1008; Christophe Bonny, Geneva (CH)

(73) Assignees: Gerard Waeber (CH); Pascal Nicod (CH)

(*) Notice: Subject to any disclaimer, the term of this patent is extended or adjusted under 35 U.S.C. 154(b) by 0 days.

This patent is subject to a terminal disclaimer.

(21) Appl. No.: 09/402,214
(22) PCT Filed: Apr. 2, 1998
(86) PCT No.: PCT/GB98/00972
§ 371 (c)(1), (2), (4) Date: Dec. 22, 1999
(87) PCT Pub. No.: WO98/44106
PCT Pub. Date: Oct. 8, 1998

(30) Foreign Application Priority Data

May 15, 1997 (GB) .............................................. 9709920
Apr. 3, 1997 (GB) .............................................. 9706731

(51) Int. Cl.$^7$ .............................................. A61K 38/16
(52) U.S. Cl. ...................... 530/358; 530/300; 435/69.1; 435/235.1; 435/325; 536/23.5
(58) Field of Search ................................. 530/300, 350, 530/358; 435/69.1, 235.1, 325; 514/12; 536/23.5

(56) References Cited

PUBLICATIONS

Skolnick et al., Trends in Biotechnology, 18:34–9, Jan. 2000.*
Bonny et al., J. Biol. Chem. 273:1843–1846, Jan. 1998.*
Peterson et al., Trends in Biotechnology, 11:11–17, Jan. 1993.*
Olefsky, JM., Nature 408–421, Nov. 2000.*

* cited by examiner

*Primary Examiner*—Patrick J. Nolan
(74) *Attorney, Agent, or Firm*—Dann, Dorfman, Herrell and Skillman

(57) ABSTRACT

The identification and characterisation of human and rat Islet-Brain 1 (IB1) is disclosed, a transcriptional activator that is involved in the control of the GLUT2 and insulin genes by interacting with homologous cis-regulatory elements of the GLUT2 and insulin promoters. The rat IB1 cDNA encodes a 714 amino acid protein and the human IB1 cDNA a 711 amino acid protein. The use of IB1 polypeptides, nucleic acid, agonists and antagonists in the treatment or diagnosis of diabetes, neurological diseases such as dementia and/or parkinsonism, the inhibition/promotion of apoptosis and cancer is disclosed.

10 Claims, 23 Drawing Sheets ccgccccagtccgaacccgcggcggcggcggcggcctcctccacgcctccacctccgcctccgccgccgcc

GAGAGCGGCCTGAGCGGGGTGCCGCGTCCCACCGGCCGCTTCCCATTCCTGGGACTGCACATGCGTCGCCTC
E  S  G  L  S  G  G  A  A  S  P  P  A  A  S  P  F  F  L  G  L  H  I  A  S  P  P

CACTGATGAGTGTGGCATCAGCCTGCAAAGACACCTTGTCTCTCCGGCCCCGCGCCCCGGCCGGGCTACTGTCT
T  D  E  C  G  I  S  L  Q  C  K  D  T  L  S  L  R  P  P  R  A  G  L  L  S

ACGCGGCAAGTGACACTCCGGGTGCCGAGGACGCCGAAGAGGACGACGAGTGCCAACGGCTCGCCAGGAGT
A  A  S  D  T  P  G  A  E  D  D  E  E  D  D  D  E  L  A  A  Q  R  P  G  V

CCCGGCACAGGCTGCGGAGACTACCGGCCAAGAGCTCAACCAGCTCTACCCTTTTCCCGAGTTCCGCGTT
P  G  T  G  C  G  D  T  Y  R  P  K  R  P  T  T  L  N  L  F  P  Q  V  P  R  S

ATCATCCTCCCCTGAAAGACAGGGGAGCAGACTCCACATGAACATATCTGCCTGAGTGATGAGCTGCCGCCC
S  S  P  L  K  T  G  E  Q  T  P  P  H  E  H  I  C  L  S  D  E  L  P  P

CAGCCACCAGATGCCACCTTCCAAGTGTCCCCGGCCACTGCCCCGGCCACTCCCATCGAGATCG
A  T  Q  M  A  P  P  S  G  P  P  A  T  A  P  G  G  R  G  H  S  H  R  D  R

CCCCCAGACCCTGCAGAACCCTCCACCTTCTTGCCACCTCCTACTGAGAGCCGGATGTCTGTCAGTCGGATCCTG
P  P  D  P  A  E  P  T  S  T  F  L  P  P  T  E  S  R  M  S  V  S  S  D  P  D

CTTCGACTGTCTGTCATCCCAGAGCAAGCTGAGCCTCCCGGAGGTGGGGGGTGGGGGCCTCGGGGAGCCACCA
F  D  C  L  S  S  P  E  Q  A  E  P  P  G  G  G  W  R  G  S  L  G  E  P  P

*Fig. 1a (Part 1 of 4)*

```
gccgccgcctcccgcgccgctctccgcccggATGGCCAGGCTGAGCCCGGGAATGGCGGAGCGA       140
                               M  A  R  L  S  P  G  M  A  E  R         11

CCAATTTCAGGCTCCACCCATGATATCAGCCTGGAGGAGTTTGAGGATGAAGACCTTTCGGAGAT      280
 N  F  R  L  T  H  D  I  S  L  E  E  F  E  D  E  D  L  S  E  I         58

GCGGGTAGCAGCGGTAGCGCGGGGAGCCGGCTGCAGGCGGAGATGCTGCAGATGGACCTGATCG       420
 A  G  S  S  G  S  A  G  S  R  L  Q  A  E  M  L  Q  M  D  L  I  D     105

GGGGCCTTCCAAAGCCGAGTCTGGCCAGGAGCCGGCTTCTCGCAGCCAGGGTCAGGGCCAGGGC       560
 G  P  S  K  A  E  S  G  Q  E  P  A  S  R  S  Q  G  Q  G  Q  G         151

CTCAGGACACGCTGAATAATAACTCTTTAGGCAAAAAGCACAGTTGGCAGGACCGTGTGTCTCG       700
 Q  D  T  L  N  N  N  S  L  G  K  K  H  S  W  Q  D  R  V  S  R         198

CAGGGCAGTCCTGTTCCACCAGGATCGTGGCCACTTCCACCGACAGCCCTTGTCGCGTACTG       840
 Q  G  S  P  V  P  T  Q  D  R  G  T  S  T  D  S  P  C  R  R  T  A     245

GTCCATATCAGCAGATGTGCGGCTCGAGGCGACTGAGGAGATCTACCTGACCCCAGTGCAGAGG      980
 S  I  S  A  D  V  R  L  E  A  T  E  E  I  Y  L  T  P  V  Q  R         291

ACCCTGCCGCTTACTCTGTAACTGCAGGGCGACCGGCACCCTTCCATCAGTGAAGAGGATGAGGG    1120
 P  A  A  Y  S  V  T  A  G  R  P  H  P  S  I  S  E  E  D  E  G         338

CCGCCTCCACGGCCTCACTGAGCTCGGACACCAGCGCACTGTCCTACGACTCTGTCAAGTACA      1260
 P  P  P  R  A  S  L  S  S  D  T  S  A  L  S  Y  D  S  V  K  Y  T     385
```

*Fig. 1a (Part 2 of 4)*

```
CACTGTGGTGGATGAGCATGCCCAGTTGGTGAGCTTGTGAGTTGGTGAGATTACAGTGACGAAAG
 L  V  V  D  E  H  A  Q  L  E  L  V  S  L  R  P  C  F  G  D  Y  S  D  E  S

GAGGAATATGAGGAGGCCCCTCAACCCGGCCTCCACCTGCTGTCAGAGGACTCCACACCGGATGAGCCTGACG
 E  E  Y  E  E  A  P  Q  P  R  P  P  T  C  L  S  E  D  S  T  P  D  E  P  D  V

GTCCTTGGGCTGTTCTCCTGTGTCATCAATGGGGAGGAGCAAACCATCGGCTATATTCAGGTTTGTG
 S  F  G  L  F  S  C  V  I  N  G  E  E  H  E  Q  T  H  R  A  I  F  R  F  V

AAGACTATTGGTATGAGGCCTATAACATGCGCACTGGAGCCCGTGGTGTCTTTCCTGCTACTATGCCATTGAGGT
 D  Y  W  Y  E  A  Y  N  M  R  T  G  A  R  G  V  F  P  A  Y  Y  A  I  E  V

GTGAAGTTCCTGGGCTCTGTCCAGTTGTCCAAGATAGTGTCAAAGCTGATGAAGCTCAGGAGGCCCAAGAGATCG
 V  K  F  L  G  S  V  Q  V  P  Y  H  K  G  N  D  V  L  C  A  A  M  Q  K  I  A

TAGGGGGTGTCAAGATAGGTGTCAAAGCTGTCAAAGCTGATGAAGCTCAGGAGGCCAAGGGAAATAAATGTAGCCACTTTTTCCAG
 R  G  V  K  I  G  V  K  A  D  E  A  Q  E  A  K  G  N  K  C  S  H  F  F  Q

AGCACCCTGCTGACCCGGTTGCTCTGCCATGTCTTTGTGTCTGAAGATTCCACCAAAGCCCTGGCAGAGTCGT
 H  P  A  D  H  R  F  A  C  H  V  F  V  S  E  D  S  T  K  A  L  A  E  S  V

TACTTGGAGTTAGcagcaacccccctctctgcagccccctcagcccccaggccagtactaggacagctgactgctgaca
 Y  L  E  * ggggagaggcagatgcagtttattgtaatatatgggttagattaatctatggaggacagtacaggctctctcggg
agaggcgctgcaccatcctggcttgttctcatctagaggccctggcttctgctcctgcctgacaa
gagcccaagcacctccgaaggacttccagtaaggaaatggcaacatgtgacagtgagacctgttctcatctgtg
aagaggagagggccacagcaagccctgcctgccaggggaagttccctctcagctgcctcagctgcctcagctgcctcaactgtcact
aaaaaaactcgag   2953
```

*Fig 1a (Part 3 of 4)*

```
CGACTCTGCCACTGTCTATGACAACTGCCTCCTGCCCTAGAGTCAGCATTGGT    1400
 D  S  A  T  V  Y  D  N  C  A  S  A  S  S  P  Y  E  S  A  I  G      431

TCCACTTCTCAAGAAGTTTCTGAATGTCTTCATGAGTGGCCGTCTCTGTTCCTCCAGTGCGA    1540
 H  F  S  K  K  F  L  N  V  F  M  S  G  R  S  R  S  S  S  A  E      478

CCTCGGCATGAAGATGAACTTGAGCTGGAAGTGGACGACCCTCTGCTGGTGGAGCTGCAGGCAG    1680
 P  R  H  E  D  E  L  E  L  E  V  D  D  P  L  L  V  E  L  Q  A  E      525

CACCAAGGAGCCTGAGCACATGGCAGCCCTTGCCAAAAACAGCGACTGGATTGACCAGTTCCGG    1820
 T  K  E  P  E  H  M  A  A  L  A  K  N  S  D  W  I  D  Q  F  R      571

CCACCACCCGGCTCACCGTGCACTTTAACCCGCCTCAGCTGTGTCCTTGAAATCAGCGT    1960
 T  T  R  R  L  T  V  H  F  N  P  P  S  S  C  V  L  E  I  S  V      618

CTAAAAACATCTCTTTCTGTGGGTACCATCCAAAGAACAACAAGTACTTTGGGTTTATCACTA    2100
 L  K  N  I  S  F  C  G  Y  H  P  K  N  N  K  Y  F  G  F  I  T  K      665

GGGGCGTGCATTTCAGCAGTTCTACAAGCAATTTGTGGAATATACCTGTCCTACAGAAGATATC    2240
 G  R  A  F  Q  Q  F  Y  K  Q  F  V  E  Y  T  C  P  T  E  D  I      711

GGATGTTGTACTGCCACGAGAGAATGGGGGTGGGGTGTTGGGGTCGGGGGCAGGGGTTT    2380 gctggggaagggcagggctggggtgggggtcaggcatctggccacaaagggtccccctaggac    2520
agcccagccgcacctggaagtgtcaccttcccttgtccacctcaccagtgccctgagctcatgct    2660
gggctccggcagctccgaccccagcctgccagcacgctgacccctggcaagcttgtgttca    2800
gtcttgtcacctggctactactaaagtgccattcttgtctgaaaaaaaaaaaaaaaaa    2940
```

*Fig 1a (Part 4 of 4)*

```
IB1    RTGAEGNFPEYYAIEVTKEPHMAAALANS............KGNDWCANVQKLLTTR
E47    R-ERERLRMRNLKRDLNRLERDINEAFRELGRMC.........KLQQQVREGQE
MyoD   A-DRRKAATVRERRRLSKVNEAFETLKRCT............KERNRVRHEGLQ
c-myc  N-VCSRTHNLLQRNELKRSFAHRDQI...............KVLKKTAVYILSVQ
E12    K-ERERLRMRNLKRDLNRLERDINEAFKELGRMC.........HQAVSVLLNLE
ITF-1  R-ERERLRMRNLKRDLNRLERDINEAFRELGRMC.........KLQQQVMTLGLE IB1
E47
MyoD
c-myc
E12
ITF-1
```

*Fig. 1B*

```
hIB-1    1 .......MAERESGGLGGGAASPPAASPFLGLHIASPPNFRLTHDISLEE  43
           |||||| || |||||||||||||||||||||||||||||||||
rIB1     1 MARLSPGMAERES.GLSGGAASPPAASPFLGLHIASPPNFRLTHDISLEE  49 hIB-1   44 FEDEDLSEITDECGISLQCKDTLSLRPPRAGLLSAG.GGGAGSRLQAEML  92
           ||||||||||||||||||||||||||||||||||| | |||||||||||
rIB1    50 FEDEDLSEITDECGISLQCKDTLSLRPPRAGLLSAGSSGSAGSRLQAEML  99 hIB-1   93 QMDLIDATGDTPGAEDDEEDDDEERAARRPGAGPPKAESGQEPASRGQGQ 142
           |||||| ||||||||||||| | ||·||| |||||||||||||||
rIB1   100 QMDLIDAASDTPGAEDDEEDDD.ELAAQRPGVGPSKAESGQEPASRSQG. 147 hIB-1  143 SQGQSQGPGSGDTYRPKRPTTLNLFPQVPRSQDTLNNNSLGKKHSWQDRV 192
           ||| | | |||||||||||||||||||||||||||||||||||||||||
rIB1   148 .QGQGPGTGCGDTYRPKRPTTLNLFPQVPRSQDTLNNNSLGKKHSWQDRV 196 hIB-1  193 SRSSSPLKTGEQTPPHEHICLSDELPPQSGPAPTTDRGTSTDSPCRRSTA 242
           |||||||||||||||||||||||||||| | || |||||||||||·  |
rIB1   197 SRSSSPLKTGEQTPPHEHICLSDELPPQGSPVPTQDRGTSTDSPCRRTAA 246 hIB-1  243 TQMAPPGGPPAAPPGGRGHSHRDRIHYQADVRLEATEEIYLTPVQRPPDA 292
           |||||| ||||  || |||||||| ||||||||||||||||||||||||
rIB1   247 TQMAPPSGPPATAPGGRGHSHRDR.SISADVRLEATEEIYLTPVQRPPDP 295 hIB-1  293 AEPTSAFLPPTESRMSVSSDPDPAAYPSTAGRPHPSISEEEEGFDCLSSP 342
           ||||| ||||||||||||||||||||| ||||||||||||·||||||||
rIB1   296 AEPTSTFLPPTESRMSVSSDPDPAAYSVTAGRPHPSISEEDEGFDCLSSP 345 hIB-1  343 ERAEPPGGGWRGSLGEPPPPPRASLSSDTSALSYDSVKYTLVVDEHAQLE 392
           |·||||||||||||||||||||||||||||||||||||||||||||||||
rIB1   346 EQAEPPGGGWRGSLGEPPPPPRASLSSDTSALSYDSVKYTLVVDEHAQLE 395 hIB-1  393 LVSLRPCFGDYSDESDSATVYDNCASVSSPYESAIGEEYEEAPRPQPPAC 442
           ||||||||||||||||||||||||||||·|·||
rIB1   396 LVSLRPCFGDYSDESDSATVYDNCASASSPYESAIGEEYEEAPQPRPPTC 445 hIB-1  443 LSEDSTPDEPDVHFSKKFLNVFMSGRSRSSSAESFGLFSCIINGEEQEQT 492
           |||||||||||||||||||||||||||||||||||||||||·|||||·|||
rIB1   446 LSEDSTPDEPDVHFSKKFLNVFMSGRSRSSSAESFGLFSCVINGEEHEQT 495 hIB-1  493 HRAIFRFVPRHEDELELEVDDPLLVELQAEDYWYEAYNMRTGARGVPPAY 542
           |||||||||||||||||||||||||||||||||||||||||||||||||
rIB1   496 HRAIFRFVPRHEDELELEVDDPLLVELQAEDYWYEAYNMRTGARGVPPAY 545 hIB-1  543 YAIEVTKEPEHMAALAKNSDWVDQFRVKFLGSVQVPYHKGNDVLCAAMQK 592
           ||||||||||||||||||||·|||||||||||||||||||||||||||
rIB1   546 YAIEVTKEPEHMAALAKNSDWIDQFRVKFLGSVQVPYHKGNDVLCAAMQK 595 hIB-1  593 IATTRRLTVHFNPPSSCVLEISVRGVKIGVKADDSQEAKGNKCSHFFQLK 642
           |||||||||||||||||||||||||||||||||·-||||||||||||||
rIB1   596 IATTRRLTVHFNPPSSCVLEISVRGVKIGVKADEAQEAKGNKCSHFFQLK 645
```

*Fig 1D (Part 1 of 2)*

```
hIB-1    643 NISPCGYHPKNNKYFGPITKHPADHRFACHVFVSEDSTKALAESVGRAFQ 692
             |||||||||||||||||||||||||||||||||||||||||||||||||
rIB1     646 NISPCGYHPKNNKYFGPITKHPADHRFACHVFVSEDSTKALAESVGRAFQ 695 hIB-1    693 QFYKQFVEYTCPTEDIYLE 711
             |||||||||||||||||||
rIB1     696 QFYKQFVEYTCPTEDIYLE 714
```

*Fig. 1D (Part 2 of 2)*

```
   1 ATGGCGGAGC GAGAAAGCGG CGGCCTGGGA GGGGGGGCCG CGTCCCCGCC
  51 CGCCGCCTCC CCGTTCCTGG GGCTGCACAT CGCTTCGCCT CCCAATTTCA
 101 GGCTCACCCA TGACATCAGC CTGGAGGAGT TTGAGGATGA AGACCTCTCG
 151 GAGATCACTG ATGAGTGTGG CATCAGCTTA CAGTGCAAAG ACACCCTGTC
 201 CTTACGGCCC CCGCGCGCCG GGCTGCTCTC TGCGGGCGGC GGCGGCGCGG
 251 GGAGCCGGTT GCAGGCCGAG ATGCTGCAGA TGGACCTGAT CGACGCGACG
 301 GGGGACACTC CCGGGGCCGA GGACGACGAG GAGGACGACG ACGAGGAGCG
 351 CGCGGCCCGG CGGCCGGGAG CGGGGCCGCC CAAGGCCGAG TCCGGCCAGG
 401 AGCCGGCGTC CCGCGGCCAG GGCCAGAGCC AAGGCCAGAG CCAGGGCCCG
 451 GGCAGCGGGG ACACGTACCG GCCCAAGCGG CCCACCACGC TCAACCTCTT
 501 TCCGCAGGTG CCGCGGTCTC AGGACACACT GAATAATAAT TCTCTGGGCA
 551 AAAAGCACAG TTGGCAGGAT CGGGTGTCTC GATCATCCTC ACCCCTGAAG
 601 ACAGGGGAGC AGACACCACC GCATGAACAC ATCTGCCTGA GCGATGAGCT
 651 GCCCCCCCAG AGCGGCCCCG CCCCCACCAC AGATCGAGGC ACCTCCACCG
 701 ACAGCCCTTG CCGCCGCAGC ACAGCCACCC AGATGGCACC TCCGGGTGGT
 751 CCCCCTGCTG CCCCGCCTGG GGGTCGGGGC CACTCGCATC GAGACCGAAT
 801 CCACTACCAG GCCGATGTGC GACTAGAGGC CACTGAGGAG ATTAACCTGA
 851 CCCCAGTGCA GAGGCCCCCA GACGCTGCAG AGCCCACCTC CGCCTTCCTG
 901 CCGCCCACTG AGAGCCGGAT GTCAGTCAGT TCCGATCCAG ACCCTGCCGC
 951 CTACCCCTCC ACGGCAGGGC GGCCGCACCC CTCCATCAGT GAAGAGGAAG
1001 AGGGCTTCGA CTGCCTGTCG TCCCAGAGC GGGCTGAGCC CCCAGGCGGA
1051 GGGTGGCGGG GGAGCCTGGG GGAGCCGCCG CCACCTCCAC GGGCCTCTCT
1101 GAGCTCGGAC ACCAGCGCCC TGTCCTATGA CTCTGTCAAG TACACGCTGG
1151 TGGTAGATGA GCATGCACAG CTGGAGCTGG TGAGCCTGCG GCCGTGCTTC
1201 GGAGACTACA GTGACGAGAG TGACTCTGCC ACCGTCTATG ACAACTGTGC
1251 CTCCGTCTCC TCGCCCTATG AGTCGGCCAT CGGAGAGGAA TATGAGGAGG
```

*Fig 1E (Part 1 of 2)*

```
1301  CCCCGCGGCC CCAGCCCCCT GCCTGCCTCT CCGAGGACTC CACGCCTGAT
1351  GAACCCGACG TCCATTTCTC CAAGAAATTC CTGAACGTCT TCATGAGTGG
1401  CCGCTCCCGC TCCTCCAGTG CTGAGTCCTT CGGGCTGTTC TCCTGCATCA
1451  TCAACGGGGA GGAGCAGGAG CAGACCCACC GGGCCATATT CAGGTTTGTG
1501  CCTCGACACG AAGACGAACT TGAGCTGGAA GTGGATGACC CTCTGCTAGT
1551  GGAGCTCCAG GCTGAAGACT ACTGGTACGA GGCCTACAAC ATGCGCACTG
1601  GTGCCCGGGG TGTCTTTCCT GCCTATTACG CCATCGAGGT CACCAAGGAG
1651  CCCGAGCACA TGGCAGCCCT GGCCAAAAAC AGTGACTGGG TGGACCAGTT
1701  CCGGGTGAAG TTCCTGGGCT CAGTCCAGGT TCCCTATCAC AAGGGCAATG
1751  ACGTCCTCTG TGCTGCTATG CAAAAGATTG CCACCACCCG CCGGCTCACC
1801  GTGCACTTTA ACCCGCCCTC CAGCTGTGTC CTGGAGATCA GCGTGCGGGG
1851  TGTGAAGATA GGCGTCAAGG CCGATGACTC CAGGAGGCC AAGGGGAATA
1901  AATGTAGCCA CTTTTTCCAG TTAAAAAACA TCTCTTTCTG CGGATATCAT
1951  CCAAAGAACA ACAAGTACTT TGGGTTCATC ACCAAGCACC CCGCCGACCA
2001  CCGGTTTGCC TGCCACGTCT TTGTGTCTGA AGACTCCACC AAAGCCCTGG
2051  CAGAGTCCGT GGGGAGAGCA TTCCAGCAGT TCTACAAGCA GTTTGTGGAG
2101  TACACCTGCC CCACAGAAGA TATCTACCTG GAGTAG
```

Fig. 1E (Part 2 of 2)

Amino acids sequence of human IB1

```
  1 MAERESGGLG GGAASPPAAS PFLGLHIASP PNFRLTHDIS LEEFEDEDLS
 51 EITDECGISL QCKDTLSLRP PRAGLLSAGG GGAGSRLQAE MLQMDLIDAT
101 GDTPGAEDDE EDDDEERAAR RPGAGPPKAE SGQEPASRGQ GQSQGQSQGP
151 GSGDTYRPKR PTTLNLFPQV PRSQDTLNNN SLGKKHSWQD RVSRSSSPLK
201 TGEQTPPHEH ICLSDELPPQ SGPAPTTDRG TSTDSPCRRS TATQMAPPGG
251 PPAAPPGGRG HSHRDRIHYQ ADVRLEATEE INLTPVQRPP DAAEPTSAFL
301 PPTESRMSVS SDPDPAAYPS TAGRPHPSIS EEEEGFDCLS SPERAEPPGG
351 GWRGSLGEPP PPPRASLSSD TSALSYDSVK YTLVVDEHAQ LELVSLRPCF
401 GDYSDESDSA TVYDNCASVS SPYESAIGEE YEEAPRPQPP ACLSEDSTPD
451 EPDVHFSKKF LNVFMSGRSR SSSAESFGLF SCIINGEEQE QTHRAIFRFV
501 PRHEDELELE VDDPLLVELQ AEDYWYEAYN MRTGARGVFP AYYAIEVTKE
551 PEHMAALAKN SDWVDQFRVK FLGSVQVPYH KGNDVLCAAM QKIATTRRLT
601 VHFNPPSSCV LEISVRGVKI GVKADDSQEA KGNKCSHFFQ LKNISFCGYH
651 PKNNKYFGFI TKHPADHRFA CHVFVSEDST KALAESVGRA FQQFYKQFVE
701 YTCPTEDIYL E*
```

*Fig. 1F*

Southern Blot Analysis of the Human *IB-1* Gene ized insulin-secreting cDNA library. In part, the success of this exercise was based on the inventors' realisation of the importance of GTII and the library they constructed to find the IB1 gene. The IB1 polypeptides described herein are relatively large, and cloning them was achieved by the construction by the inventors of a high quality cDNA library for expression cloning.

TRANSCRIPTION FACTOR ISLET-BRAIN 1 (IB1)

CROSS REFERENCE TO RELATED APPLICATIONS

This application is a §371 application of PCT/GB98/00972, filed on Apr. 2, 1998, which in turn claims priority to GB applications 9706731.8 filed Apr. 3, 1997 and 9709920.4 filed May 15, 1997. Each of the above-identified applications is incorporated by reference herein.

FIELD OF THE INVENTION

The present invention relates to identification and characterisation of Islet-Brain 1 (IB1), a transcriptional activator that is involved in the control of the GLUT2 and insulin genes by interacting with homologous cis-regulatory elements of the GLUT2 and insulin promoters, and to materials and methods deriving from this work. In particular, the present invention relates to the uses of IB1 nucleic acid, IB1 polypeptides, IB1 antagonists and antibodies in the diagnosis, and prophylactic and therapeutic treatment of conditions such as diabetes, neurological diseases such as dementia and/or parkinsonism, cancer and in the promotion or inhibition of apoptosis.

BACKGROUND OF THE INVENTION

The GLUT2 facilitated glucose transporter isoform is a membrane protein present in the pancreatic β-insulin-secreting cells, the basolateral membrane of intestinal and kidney absorptive cells, in hepatocytes and in a subset of neurons (21,31,44). In these cells, GLUT2 catalyzes the transepithelial transport of glucose. In pancreatic islets, GLUT2 allows a rapid equilibration of glucose between the extracellular space and the interior of the cells and it may play a crucial role in the glucose signalling mechanism leading to insulin secretion (43). However, the relative importance of GLUT2 in the sensing of the β-pancreatic cells to glucose remains debated. In human β-cells, the level of expression of GLUT2 is low and the intracellular glucokinase activity seems to be the rate-limiting step in the glycolytic pathway (5,11). On the other hand, insulinoma cells that had lost their normal glucose responsiveness have low GLUT2 content, but some glucose sensitivity may be recovered after reintroducing GLUT2 expression through stable transfection of these cells (10,16). Furthermore, transgenic mice that express GLUT2 antisense RNAs driven by the insulin promoter led to an 80% reduction in GLUT2 which was paralleled by a decreased glucose-induced insulin secretory response and by the onset of diabetes (48). These observations are critical since several experimental models of diabetes have shown that GLUT2 expression is dramatically reduced specifically in the pancreatic β-cells, and that this mechanism could participate to the onset of the disease (18,29,30,32,45–47). Therefore, while GLUT2 levels are unchanged or even upregulated in several tissues such as the liver and the intestine during the hyperglycemic conditions observed in diabetes, the same gene undergoes a drastic dysregulation only in the pancreatic islets.

A fragment of the murine GLUT2 promoter has been cloned and shown to be glucose-responsive when transfected into differentiated insulin-producing cells or into hepatocytes (35,36,52). Important cis-regulatory sequences were identified within this promoter region including a functionally responsive PDX-1 element, a cyclic AMP responsive element, and three cis-elements termed GTI, GTII and GTIII (3,36,53). The presence of GTI, II and III are both sufficient and necessary to confer pancreatic-specific expression to a reporter gene in vitro or in vivo, using a transgenic mice approach (3,51). GTI and GTIII have been previously shown to bind distinct, but ubiquitously expressed trans-acting factors.

SUMMARY OF THE INVENTION

The present invention is based on successful expression cloning of a transcription factor that binds to the GTII element of the GLUT2 and insulin genes from a differentiated insulin-secreting cDNA library. In part, the success of this exercise was based on the inventors' realisation of the importance of GTII and the library they constructed to find the IB1 gene. The IB1 polypeptides described herein are relatively large, and cloning them was achieved by the construction by the inventors of a high quality cDNA library for expression cloning.

This factor is abundantly expressed in the pancreatic islets and in the brain and has been named IB-1 for Islet-Brain 1. Both human and rat IB1 genes and polypeptides have been obtained. The rat IB1 cDNA (SEQ ID NO: 1) encodes a 714 amino acid protein (SEQ ID NO: 2) and the human IB1 cDNA (SEQ ID NO: 3) a 711 amino acid protein (SEQ ID NO: 4). The cDNAs encoding the rat and human IB1 polypeptides have a 94% sequence identity and the polypeptides have a 97% amino acid sequence identity (see the alignment of the sequences in FIG. 1D), and have a proline-rich region and a putative basic helix-loop-helix domain (bHLH). The IB1 gene is highly expressed in the pancreatic islets and in the brain and to a much lesser extent in the heart and the kidney. In the Langerhans islets and in β-cell lines, these transcripts are translated into immunodetectable cytoplasmic and nuclear protein. When tested in vitro, IB1 bound specifically to the GTII cis element of the GLUT2 gene and to an homologous regulatory sequence of the insulin promoter termed RIPE3. This rat insulin promoter element 3 (RIPE3) is an important enhancer sequence sufficient to confer β-cell specific expression to the insulin gene. Functionally, IB1 transactivated the proximal region of the GLUT2 promoter linked to a luciferase reporter gene and was also a potent activator of the insulin gene. This effect is mediated through the RIPE3 sequence as demonstrated by the observation that multiple copies of this enhancer sequence cloned 5' of an heterologous promoter was transactivated by an expression vector encoding IB1 in transient transfection studies. IB1 appears to function only in insulin-secreting cells as no transactivation was observed in non-pancreatic or in glucagon-producing cell lines. These data demonstrate the presence of a novel transcriptional activator abundantly expressed in the endocrine pancreas and which participates to the proper β-cell specific control of the GLUT2 and the insulin genes through homologous sequences present in both promoters.

The nucleic acid and amino acid sequences (SEQ ID NOS: 1 and 2) of rat IB1 are shown in FIG. 1A. The human IB1 cDNA (SEQ ID NO: 3) is shown in FIG. 1E, with the translated amino acid sequence (SEQ ID NO: 4) shown in FIG. 1F. The human IB1 gene is located on chromosome 11 at 11p11.12 on the LDB cytogenic map. The IB1 gene is adjacent to markers D11S134 and D11S3979.

The human cDNA was constructed as RNA using tissue obtained from a surgically removed human insulinoma. Poly A$^+$ RNA was extracted and a cDNA library constructed and subsequently screened with a radiolabelled rat IB1 cDNA probe. This allowed the inventors to isolate the human cDNA encoding IB1. This cDNA was then used as a probe to clone the human IB1 gene from a bacterial artificial chromosome (BAC). Several clones were obtained and part of them sequenced. The above protocol was then used to complete the sequencing of the human IB1 nucleic acid shown in FIG. 1E (SEQ ID NO: 3).

The human IB1 gene is multiexonic and is located in chromosome 11p11.12. The chromosomal mapping was obtained by FISH experiments and PCR of hybrid cells (hamster-human) using as a probe the multiexonic IB1 gene. IB1 is expressed in the brain of rat, mouse and human species and in tissues with a high degree of similarity such as the endocrine pancreas (many neuronal features are present in the insulin β-cells).

In a first aspect, the present invention provides a substance which is an isolated polypeptide comprising a polypeptide having the amino acid sequence set out in FIG. 1A (SEQ ID NO: 2) or FIG. 1F (SEQ ID NO: 4).

In a further aspect, the present invention provides a substance which is an isolated polypeptide having greater than 80% amino acid sequence identity with the amino acid sequence set out in FIG. 1A (SEQ ID NO: 2) or 1F (SEQ ID NO: 4).

In a further aspect, the present invention provides a substance which is a polypeptide which is a mutant, variant, derivative or allele of any one of the above polypeptides.

In a further aspect, the present invention provides a substance which is a fragment of a polypeptide having the amino acid sequence set out in FIG. 1A or 1F which exhibits a biological property of full length IB1 protein. In one embodiment, the fragment includes the domain from amino acids 566–612 (SEQ ID NO: 2) of the sequence shown in FIG. 1A or the domain from amino acids 563–609 (SEQ ID NO: 4) of the sequence shown in FIG. 1F, or an active portion of that domain. In an alternative embodiment, the present invention provides a polypeptide which is a protein interaction domain having the sequence shown in FIG. 1A from amino acids 566–612 (SEQ ID NO: 2) and in FIG. 1E from amino acids 563–609 (SEQ ID NO: 4). As this domain is believed to be responsible for some of the interactions between IB1 and other polypeptides, it can be used in methods of screening for binding partners, e.g. peptides which could act as inhibitors of IB1.

In a further aspect, the present invention provides isolated nucleic acid molecules encoding any one of the above polypeptides. Examples of such nucleic acid sequences are the nucleic acid sequences set out in FIGS. 1A (SEQ ID NO: 1) and 1E (SEQ ID NO: 3). The present invention also include nucleic molecules having greater than a 90% sequence homology with the nucleic acid sequence of FIG. 1A or 1E.

In further aspects, the present invention provides an expression vector comprising the above IB1 nucleic acid operably linked to control sequences to direct its expression, and host cells transformed with the vectors. The present invention also includes a method of producing IB1 polypeptides comprising culturing the host cells and isolating the IB1 polypeptide thus produced.

In a further aspect, the present invention provides an expression vector comprising IB1 nucleic acid for use in methods of gene therapy, e.g. in the treatment of patients unable to produce sufficient IB1 or to engineer cell lines capable of producing IB1.

In a further aspect, the present invention provides a cell line for transplantation into a patient, the cell line being transformed with nucleic acid encoding an IB1 protein, and being capable of producing IB1 polypeptide. The expression of IB1 in a transformed cell line can affect endogenous genes such as the insulin or GLUT2 genes. In one embodiment, the cell lines can be encapsulated, e.g. in a biocompatible polymer so that the IB1 produced by the cells line can be secreted into the patient, while preventing rejection by the immune system of the host. Methods for encapsulating cells in biocompatible polymers are described in WO93/16687 and WO96/31199.

In a further aspect, the present invention provides a pharmaceutical composition comprising an IB1 nucleic acid molecule.

In a further aspect, the present invention provides a pharmaceutical composition comprising one or more IB1 polypeptides as defined above.

In further aspects, the present invention provides the above IB1 polypeptides and nucleic acid molecules for use in methods of medical treatment. The present invention further provides the use of the IB1 polypeptides in the preparation of medicament for activating the GLUT2 or insulin promoters leading to the production of GLUT2 or insulin. Preferably, the activation takes place in a cell specific manner, e.g. in β-cells. This could be used in the treatment of conditions treatable using insulin or GLUT2, such as diabetes. Since IB1 is also present in muscle tissue such as the heart it may function by modulating insulin sensitivity and ameliorating abnormal glucose disposal in diabetic patients.

IB1 could also be used as an agent which maintains a state of differentiation within in a cell, i.e. acts as an anti-apoptotic agent. Thus, IB1 can be used as an anti-neoplastic agent, e.g. as a drug to control or treat some cancers. As an example, insulinomas are human tumours which undergo dedifferentiation and divide. Thus, IB1 antagonists could be used to attack tumour cells, while IB1 could be used to protect surrounding healthy tissue from the effects of treating tumour cells, using IB1 antagonists and/or conventional radiotherapy or chemotherapy. Thus, IB1 could act as a differentiation agent to treat these cells. A further application of IB1 antagonists is in the treatment of brain tumours, such as glioblastomas which are typically untreatable using conventional medicine.

IB1 is similar to JIP-1, a cytoplasmic protein identified by Dickens et al,. Science, 277:693–696, 1997. However, IB1 differs from JIP-1 by the insertion of 47 amino acids in the carboxy terminal portion of the protein, and has a 97% amino acid homology over the remaining sequence of rat IB1 shown in FIG. 1A (i.e. excluding the insert not present in JIP-1). As overexpression of JIP-1 in neuronal cells inhibits apoptosis of the cells, IB1 could be used to suppress apoptosis in cells, e.g. stress-induced apoptosis induced in neurons. This stress activation can be caused by ultraviolet (uv) radiation, anoxia, hypoglycemia, cytokines such as IL-6, or by trauma.

This in turn supports the present inventors' earlier suggestion to the use of IB1 to prevent cell death that occurs in diseases such as dementia, neurodegenerative diseases, ischemia of the heart, myocardial infarction (IB1 is present in heart), and post trauma, e.g. in sections of the spine in paraplegia and in neuronal trauma.

In a further aspect, the present invention provides the use of the IB1 polypeptides in screening candidate compounds for IB1 biological activity, e.g. to find peptidyl or non-peptidyl mimetics of the IB1 polypeptides to develop as lead compounds in pharmaceutical research.

In a further aspect, the present invention provides antibodies capable of specifically binding to the above IB1 polypeptides. These antibodies can be used in assays to detect and quantify the presence of IB1 polypeptide, in methods of purifying IB1 polypeptides, and in pharmaceutical compositions, e.g. to neutralize IB1 in conditions in which its overexpression has deleterious effect, or to inhibit the anti-apoptotic effect of IB1 in diseased tissue such as tumours. Accordingly, antagonists such as antibodies which block the expression of IB1 or neutralize IB1 in the tissues in which it is overexpressed can be used for treating such conditions and are included within the present invention. Polyclonal antibodies to the N-terminal portion (residues 1–280 (SEQ ID NO: 2)) of the IB1 protein of FIG. 1A are exemplified below.

In a further aspect, the present invention method for determining the presence of IB1 nucleic acid and/or mutations within an IB1 nucleic acid sequence in a test sample comprising detecting the hybridization of test sample nucleic acid to a nucleic acid probe based on the IB1 nucleic acid sequences set out in FIG. 1A or 1E.

In a further aspect, the present invention provides the use of IB1 nucleic acid as defined above in the design of antisense oligonucleotides to restrict IB1 expression in a population of cells, i.e. phosphorothiolated or chloresterol linked oligonucleotides which can facilitate internalization and stabilization of the oligonucleotides.

In a further aspect, the present invention provides a method of amplifying a nucleic acid test sample comprising priming a nucleic acid polymerase reaction with nucleic acid encoding an IB1 polypeptide as defined above. The present invention also provides the use of the above nucleic acid in the search for mutations in the IB1 genes, e.g. using techniques such as single stranded conformation polymorphism (SSCP).

These and other aspects of the present invention are described in more detail below.

By way of example, embodiments of the present invention will now be described in more detail with reference to the accompanying figures.

Figure 1C:
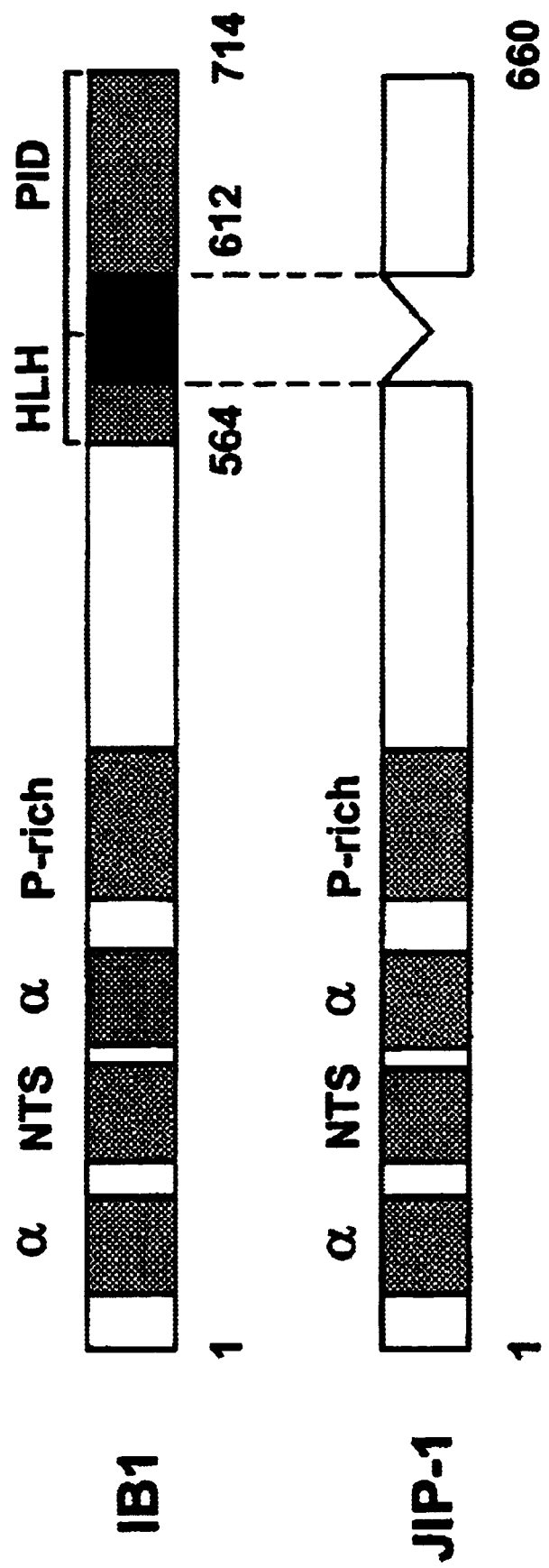
FIG. 1
IB1 cDNA and Predicted Protein Sequence.
A. Nucleotide sequence of rat IB1 cDNA (SEQ ID NO: 1) and its predicted amino acid sequence (SEQ ID NO: 2). The nucleic acid residues are numbered from the nucleotide in the cDNA, and the amino acid residues are numbered from the beginning of the long open reading frame. Computer assisted analysis of the protein sequence indicates the presence of highly helicoidal structure (residues 31–61 and 114–125) and a proline-rich region (residues 292–366) in amino-terminal part of the protein, a putative nuclear localization signal (underlined twice) as well as a putative DNA-binding domain and bHLH dimerization domain (underlined once).
B. Amino acid sequence comparison of IB1 with other bHLH proteins (SEQ ID NOS: 5–16). Amino acid sequence were aligned to maximize homology within the bHLH region. Shaded amino acids are conserved among bHLH proteins.
C. A schematic diagram of the IB1 protein with putative domains indicated. Note the 47 amino acid insertion (black box) which differentiates IB1 from JIP-1.
D. Comparison of the rat and human IB1 translated amino acid sequences (SEQ ID NOS: 2 and 17, respectively). =identity, bold=47 amino acid insert in IB1, =no amino acid present.
E. Complete nucleotide sequence of human IB1 cDNA (SEQ ID NO: 3), =exon-intron junction.
F. Complete amino acid sequence of human IB1 polypeptide (SEQ ID NO: 4).

A. Nucleic acid sequences (SEQ ID NOS: 54 and 55) comparison between the murine GTII cis regulatory element and the rat insulin promoter element 3 (RIPE3). Some sequence identity is depicted and correspond, in part, to the RIPE3b element.

B. SouthWestern experiments were conducted using INS-1 nuclear extracts separated by SDS-PAGE gel electrophoresis and transferred to nitrocellulose membrane subsequently incubated with concatanated GTII, GTIII and RIPE3 labelled oligonucleotides. No specific binding was detected with the GTIII probe whereas the GTII and RIPE3 probes bind to an approximately 120 kDa protein and with less specificity to a factor present at 40 kDa, also detectable with the GTIII probe.

C. Plasmids containing the IB1 CDNA driven by a CMV promoter (pCMV-IB1) or its parent vector (pCMV) was transiently transfected into COS-7 cells and crude cellular extracts (20 μg) of these transfected cells were analyzed by SouthWestern with the labeled GTII probe. The 120 kDa expressed protein is detected only in the transfected cells with the eukaryotic expression vector containing IB1 cDNA.

D. Gel retardation analysis conducted with the GTII and RIPE3 probes using βTC3 nuclear extracts. The RIPE3-binding activity is competed with an 100-fold excess of unlabelled RIPE3 or GTII oligonucleotides but not with an unrelated sequence (GTI). Conversely, the GTII-binding activity is competed with a 1000-fold excess of unlabelled RIPE3 oligonucleotides but not with an unrelated sequence (GTI).

FIG. 5

Activation of the Insulin Enhancer Constructs and the GLUT2 Promoter by IB1

A. Two μg of the eukaryotic expression vector containing the IB1 cDNA (PBKS/IB1) or its parent vector (PBKS) were transiently transfected into βTC3 cells together with 1 μg of the promoterless vector encoding the luciferase gene (pGL3) or −338 bp of the murine GLUT2 promoter cloned into the pGL3 vector (−338LUC) or −410 bp of the rat insulin I promoter similarly cloned into pGL3 (−410LUC). IB1 transactivates the GLUT2 promoter (1.6·0.1 (SEM) over basal) but is a potent transactivator of the insulin promoter (3.8·0.8 (SEM) fold increase over basal). This effect is β-cell specific as it was not observed in a glucagon-producing cell line (InR1-G9, data not shown) or in an unrelated cells (COS-3).

B. Several exonuclease III deletions constructs of the rat insulin promoter linked to a CAT reporter gene were transiently transfected into βTC3 cells in the presence of PBKS or PBKS/IB1. IB1 transactivated the insulin promoter and this effect was maximal within the −316 to −159 bp of the gene. Representative study done in duplicate in three independent experiments, normalized by protein content.

C. Five copies of the RIPE3 motif were multimerized 5' of a SV40 promoter linked to a luciferase reporter gene. This construct was transfected into βTC3 cells in the presence of the PBKS or the PBKS/IB1 construct. IB1 transactivated the RIPE3-luc construct in these cells (2.9·0.3 (SEM) fold increase over basal). Representative experiment done 12 times, in duplicate and normalized by protein content and/or the co-transfection of a HSK/TK-Renilla luciferase construct as internal control.

FIG. 6

Structure and Organization of the Human IB1 Gene, the Human IB1 cDNA and the Human IB1 Pseudogene.

The 3' end sequence of the human IB1 cDNA was obtained by screening a human insulinoma cDNA library, whereas the 5' end was obtained by RACE approach (upper lane) or by comparing the genomic sequence (obtained by subcloning a BAC clone) with the sequence of the rat IB1 cDNA, as described in the Methods. The human IB1 gene contains 12 exons (black rectangles) separated by 11 introns. The functional domains of IB1, as deduced from computer analysis, are given within the cDNA rectangle; α denotes alpha-helicoidl structure; NTS: nuclear translocation signal: P-rich: proline rich region; HLH: helix-loop-helix structure; PID: phosphotyrosine-interaction-domain. Sequence of the IB1 pseudogene was obtained by sequence analysis of part of a 4.8 kb fragment isolated by subcloning of a BAC clone.

FIG. 7

Southern Blot Analysis

This figure shows Southern blot analysis of the human IB1 gene.

DETAILED DESCRIPTION

IB1 Nucleic Acid

AIB1 nucleic acid® includes a nucleic acid molecule which has a nucleotide sequence encoding a polypeptide which includes the amino acid sequence shown in FIG. 1A (SEQ ID NO: 2), 1D (SEQ ID NOS: 2 and 17) or 1F (SEQ ID NO: 4).

The IB1 coding sequence may be that shown in FIG. 1A (SEQ ID NO: 1) or 1E (SEQ ID NO: 3), a complementary nucleic acid sequence, or it may be a mutant, variant, derivative or allele of these sequences. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in FIG. 1A or 1E yet encode a polypeptide with the same amino acid sequence. The amino acid sequence of the complete rat IB1 polypeptide shown in FIG. 1A (SEQ ID NO: 2) consists of 714 amino acids. The complete human IB1 cDNA sequence is set out in FIG. 1E (SEQ ID NO: 3), with the translated amino acid sequence consisting of 711 amino acids set out in FIG. 1F (SEQ ID NO: 4). Human and rat IB1 share a 94% nucleic acid sequence identity and a 97% amino acid sequence identity.

On the other hand, the encoded polypeptide may comprise an amino acid sequence which differs by one or more amino acid residues from the amino acid sequence shown in FIG. 1A, 1D or 1F. Nucleic acid encoding a polypeptide which is an amino acid sequence mutant, variant, derivative or allele of the sequence shown in FIG. 1A, 1D or 1F is further provided by the present invention. Such polypeptides are discussed below. Nucleic acid encoding such a polypeptide may show greater than about 60% homology with the coding sequence shown in FIG. 1A or 1E greater than about 70% homology, greater than about 80% homology, greater than about 90% homology, greater than about 95% homology, greater than about 98% homology, or greater than about 99% homology.

The present invention also includes fragments of the IB1 nucleic acid sequences described herein, the fragments preferably being at least 12, 15, 30, 45, 60, or 120 nucleotides in length.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, CDNA or RNA. Where nucleic acid according to the invention includes RNA, reference to the sequence shown should be construed as reference to the RNA equivalent, with U substituted for T.

Nucleic acid sequences encoding all or part of the IB1 gene and/or its regulatory elements can be readily prepared by the skilled person using the information and references contained herein and techniques known in the art (for example, see Sambrook, Fritsch and Maniatis, AMolecular Cloning, A Laboratory Manual, Cold Spring Harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) amplification in E. coli. Modifications to the IB1 sequences can be made, e.g. using site directed mutagenesis, to provide expression of modified IB1 polypeptide or to take account of codon preference in the host cells used to express the nucleic acid.

In order to obtain expression of the IB1 nucleic acid sequences, the sequences can be incorporated in a vector having control sequences operably linked to the IB1 nucleic acid to control its expression. The vectors may include other sequences such as promoters or enhancers to drive the expression of the inserted nucleic acid, nucleic acid sequences so that the IB1 polypeptide is produced as a fusion and/or nucleic acid encoding secretion signals so that the polypeptide produced in the host cell is secreted from the cell. IB1 polypeptide can then be obtained by transforming the vectors into host cells in which the vector is functional, culturing the host cells so that the IB1 polypeptide is produced and recovering the IB1 polypeptide from the host cells or the surrounding medium. Prokaryotic and eukaryotic cells are used for this purpose in the art, including strains of E. coli, yeast, and eukaryotic cells such as COS or CHO cells. The choice of host cell can be used to control the properties of the IB1 polypeptide expressed in those cells, e.g. controlling where the polypeptide is deposited in the host cells or affecting properties such as its glycosylation and phosphorylation.

PCR techniques for the amplification of nucleic acid are described in U.S. Pat. No. 4,683,195. In general, such techniques require that sequence information from the ends of the target sequence is known to allow suitable forward and reverse oligonucleotide primers to be designed to be identical or similar to the polynucleotide sequence that is the target for the amplification. PCR comprises steps of denaturation of template nucleic acid (if double-stranded), annealing of primer to target, and polymerisation. The nucleic acid probed or used as template in the amplification reaction may be genomic DNA, cDNA or RNA. PCR can be used to amplify specific sequences from genomic DNA, specific RNA sequences and cDNA transcribed from mRNA, bacteriophage or plasmid sequences. The IB1 nucleic acid sequences provided herein readily allow the skilled person to design PCR primers. References for the general use of PCR techniques include Mullis et al, Cold Spring Harbor Symp. Quant. Biol., 51:263, (1987), Ehrlich (ed), PCR Technology, Stockton Press, NY, 1989, Ehrlich et al, Science, 252:1643–1650, (1991), "PCR protocols; A Guide to Methods and Applications", Eds. Innis et al, Academic Press, New York, (1990).

Also included within the scope of the invention are antisense oligonucleotide sequences based on the IB1 nucleic acid sequences described herein, particularly to block the synthesis of IB1 in situations where IB1 overexpression has a deleterious effect, or where it is desirable to inhibit the anti-apoptotic effect of IB1, e.g. in the treatment of cancer. Antisense oligonucleotides may be designed to hybridize to the complementary sequence of nucleic acid, pre-mRNA or mature mRNA, interfering with the production of polypeptide encoded by a given DNA sequence (e.g. either native IB1 polypeptide or a mutant form thereof), so that its expression is reduce or prevented altogether. In addition to the IB1 coding sequence, antisense techniques can be used to target the control sequences of the IB1 gene, e.g. in the 5' flanking sequence of the IB1 coding sequence, whereby the antisense oligonucleotides can interfere with IB1 control sequences. The construction of antisense sequences and their use is described in Peyman and Ulman, Chemical Reviews, 90:543–584, (1990), Crooke, Ann. Rev. Pharmacol. Toxicol., 32:329–376, (1992), and Zamecnik and Stephenson, P.N.A.S, 75:280–284, (1974).

The nucleic acid sequences provided in FIGS. 1A and 1E are useful for identifying nucleic acid of interest (and which may be according to the present invention) in a test sample. The present invention provides a method of obtaining nucleic acid of interest, the method including hybridization of a probe having the sequence shown in FIG. 1A (SEQ ID NO: 1) or 1E (SEQ ID NO: 3) or a complementary sequence, to target nucleic acid.

Hybridization is generally followed by identification of successful hybridization and isolation of nucleic acid which has hybridized to the probe, which may involve one or more steps of PCR.

Nucleic acid according to the present invention is obtainable using one or more oligonucleotide probes or primers designed to hybridize with one or more fragments of the nucleic acid sequence shown in FIG. 1A (SEQ ID NO: 1) or 1E (SEQ ID NO: 3), particularly fragments of relatively rare sequence, based on codon usage or statistical analysis. A primer designed to hybridize with a fragment of the nucleic acid sequence shown in the above figures may be used in conjunction with one or more oligonucleotides designed to hybridize to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridizes with the sequence shown in FIG. 1A (SEQ ID NO: 1) or 1E (SEQ ID NO: 3) and a primer which hybridizes to the oligonucleotide linker.

Such oligonucleotide probes or primers, as well as the full-length sequence (and mutants, alleles, variants and derivatives) are also useful in screening a test sample containing nucleic acid for the presence of alleles, mutants and variants, especially those that lead to the production of inactive forms of IB1 protein, the probes hybridizing with a target sequence from a sample obtained from the individual being tested. The conditions of the hybridization can be controlled to minimise non-specific binding, and preferably stringent to moderately stringent hybridization conditions are preferred. The skilled person is readily able to design such probes, label them and devise suitable conditions for the hybridization reactions, assisted by textbooks such as Sambrook et al (1989) and Ausubel et al (1992).

As well as determining the presence of polymorphisms or mutations in the IB1 sequence, the probes may also be used to determine whether mRNA encoding IB1 is present in a cell or tissue.

Nucleic acid isolated and/or purified from one or more cells (e.g. human) or a nucleic acid library derived from nucleic acid isolated and/or purified from cells (e.g. a cDNA library derived from mRNA isolated from the cells), may be probed under conditions for selective hybridization and/or subjected to a specific nucleic acid amplification reaction such as the polymerase chain reaction (PCR). The human IB1 gene is located on chromosome 11 (11p11.12) and contains multiple exons. Polymorphisms within this gene may be used as markers for human genetic diseases such as diabetes, and neurological disorders including neurodegenerative diseases, such as dementia, Parkinsonism, and Alzheimer's disease; refractory epilepsy (familial forms); neuronal disabilities such as speech disorders and memory alteration; neuronal or glial tumours such as neuroblastoma or glioblastoma; autoimmune disease affecting the CNS such as systematic lupus erythromatosis; diabetes; heart diseases such as myocardial infarct and ischemia as apoptosis is involved in areas surrounding infarct; and brain attack, in particular in the prevention of apoptosis in ischemia or infarct.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

A method may include hybridization of one or more (e.g. two) probes or primers to target nucleic acid. Where the nucleic acid is double-stranded DNA, hybridization will generally be preceded by denaturation to produce single-stranded DNA. The hybridization may be as part of a PCR procedure, or as part of a probing procedure not involving PCR. An example procedure would be a combination of PCR and low stringency hybridization. A screening procedure, chosen from the many available to those skilled in the art, is used to identify successful hybridization events and isolated hybridized nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAse cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridized to the DNA fragments on the filter and binding determined. DNA for probing may be prepared from RNA preparations from cells.

Preliminary experiments may be performed by hybridizing under low stringency conditions various probes to Southern blots of DNA digested with restriction enzymes. Suitable conditions would be achieved when a large number of hybridizing fragments were obtained while the background hybridization was low. Using these conditions, nucleic acid libraries, e.g. cDNA libraries representative of expressed sequences, may be searched.

Those skilled in the art are well able to employ suitable conditions of the desired stringency for selective hybridization, taking into account factors such as oligonucleotide length and base composition, temperature and so on.

On the basis of amino acid sequence information, oligonucleotide probes or primers may be designed, taking into account the degeneracy of the genetic code, and where appropriate, codon usage of the organism from the candidate nucleic acid is derived. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but not more than 18–20. Those skilled in the art are well versed in the design of primers for use processes such as PCR.

A further aspect of the present invention provides an oligonucleotide or polynucleotide fragment of the nucleotide sequence shown in FIG. 1A (SEQ ID NO: 1) or 1E (SEQ ID NO: 3), or a complementary sequence, in particular for use in a method of obtaining and/or screening nucleic acid. The sequences referred to above may be modified by addition, substitution, insertion or deletion of one or more nucleotides, but preferably without abolition of ability to hybridize selectively with nucleic acid with the sequence shown in FIG. 1A (SEQ ID NO: 1) or 1E (SEQ ID NO: 3), that is wherein the degree of homology of the oligonucleotide or polynucleotide with one of the sequences given is sufficiently high.

In some preferred embodiments, oligonucleotides according to the present invention that are fragments of any of the sequences shown in FIG. 1A (SEQ ID NO: 1) or 1E (SEQ ID NO: 3), or an allele thereof, are at least about 10 nucleotides in length, more preferably at least about 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of susceptibility to one of the conditions mentioned above, e.g. diabetes, Parkinsonism and/or dementia.

Nucleic acid according to the present invention may be used in methods of gene therapy, for instance in treatment of individuals with the aim of preventing or curing (wholly or partially) the above mentioned conditions. This too is discussed below.

A convenient way of producing a polypeptide according to the present invention is to express nucleic acid encoding it, by use of the nucleic acid in an expression system. The use of expression systems has reached an advanced degree of sophistication.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction of nucleic acid may take place in vivo by way of gene therapy, as discussed below.

A host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

This may have a therapeutic aim. (Gene therapy is discussed below.) The presence of a mutant, allele or variant sequence within cells of an organism, particularly when in place of a homologous endogenous sequence, may allow the organism to be used as a model in testing and/or studying the role of the IB1 gene or substances which modulate activity of the encoded polypeptide in vitro.

Instead of or as well as being used for the production of a polypeptide encoded by a transgene, host cells may be used as a nucleic acid factory to replicate the nucleic acid of interest in order to generate large amounts of it. Multiple copies of nucleic acid of interest may be made within a cell when coupled to an amplifiable gene such as DHFR. Host cells transformed with nucleic acid of interest, or which are descended from host cells into which nucleic acid was introduced, may be cultured under suitable conditions, e.g. in a fermenter, taken from the culture and subjected to processing to purify the nucleic acid. Following purification, the nucleic acid or one or more fragments thereof may be used as desired, for instance in a diagnostic or prognostic assay as discussed elsewhere herein.

IB1 Proteins

The term "IB-1 biological activity" is herein defined as binding to nucleic acid defining the GTII or RIPE3 promoter elements to cause transcriptional activation of a gene under the control of a promoter including those elements. Experiments to determine this and other IB1 activities are described in detail below.

The skilled person can use the techniques described herein and others well known in the art to produce large amounts of the IB1 polypeptide, or fragments or active portions thereof, for use as pharmaceuticals, in the developments of drugs and for further study into its properties and role in vivo.

Thus, a further aspect of the present invention provides a polypeptide which has the amino acid sequence shown in FIG. 1A (SEQ ID NO: 2), 1D (SEQ ID NOS: 2 and 17) or 1F (SEQ ID NO: 4), which may be in isolated and/or purified form, free or substantially free of material with which it is naturally associated, such as other polypeptides or such as human polypeptides other than IB1 polypeptide or (for example if produced by expression in a prokaryotic cell) lacking in native glycosylation, e.g. unglycosylated.

Polypeptides which are amino acid sequence variants, alleles, derivatives or mutants are also provided by the present invention. A polypeptide which is a variant, allele, derivative or mutant may have an amino acid sequence which differs from that given in FIG. 1A, 1D or 1F by one or more of addition, substitution, deletion and insertion of one or more amino acids. Preferred polypeptides have IB1 function, that is to say they activate the GLUT2 or insulin promoters, leading to production of GLUT2 protein or insulin. Preferably, this activation is specific to insulin-secreting cells and does not take place in non-pacreatic or glucagon producing cells.

A polypeptide which is an amino acid sequence variant, allele, derivative or mutant of the amino acid sequence shown in FIG. 1A (SEQ ID NO: 2), 1D (SEQ ID NOS: 2 and 17) or 1F (SEQ ID NO: 4) may comprise an amino acid sequence which shares greater than about 35% sequence identity, greater than about 40%, greater than about 50%, greater than about 60%, greater than about 70%, greater than about 80%, greater than about 90%, greater than about 95%, greater than about 97%, greater than about 98% or greater than about 99% sequence identity with the amino acid sequence shown in FIG. 1A (SEQ ID NO: 2), 1D (SEQ ID NOS: 2 and 17) or 1F (SEQ ID NO: 4). Sequence comparison was made using the GCG program which is available from Genetics Computer Group, Oxford Molecular Group, Madison, Wisconsin, USA, Version 9.1. Particular amino acid sequence variants may differ from those shown in FIG. 1A (SEQ ID NO: 2), 1D (SEQ ID NOS: 2 and 17) or 1F (SEQ ID NO: 4) by insertion, addition, substitution or deletion of 1 amino acid, 2, 3, 4, 5–10, 10–20 20–30, 30–50, 50–100, 100–150, or more than 150 amino acids. In this connection, "sequence identity" means strict amino acid identity between the sequences being compared. However, "sequence similarity" includes conserved changes in amino acid sequence on the basis that such conserved changes will not substantially affect the structure and/or function of the protein. By way of example, sequence identity exists when two polypeptides have a Met residue at corresponding positions. If the two polypeptides had a Val and Ile at corresponding positions, there is a high degree of similarity as both amino acids have hydrophobic side chains. A lower degree of similarity exists between Ser and Ala, while no similarity exists between Gln and Glu. Methods of comparing similarity are well known in the art.

The present invention also includes active portions, fragments, derivatives and functional mimetics of the IB1 polypeptides of the invention.

An "active portion" of IB1 polypeptide means a peptide which is less than said full length IB1 polypeptide, but which retains at least some of its essential biological activity. For instance, smaller fragments of IB1 can act as sequestrators or competitive antagonists by interacting with other proteins.

A "fragment" of the IB1 polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the IB1 polypeptide sequence antigenic determinants or epitopes useful for raising antibodies to a portion of the IB1 amino acid sequence.

A "derivative" of the IB1 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one, two, three, five or more amino acids, without fundamentally altering the essential activity of the wild type IB1 polypeptide.

"Functional mimetic" means a substance which may not contain an active portion of the IB1 amino acid sequence, and probably is not a peptide at all, but which retains the essential biological activity of natural IB1 polypeptide. The design and screening of candidate mimetics is described in detail below.

In some embodiments, the fragments or derivatives include the domain from amino acids 566–612 of the sequence shown in FIG. 1A (SEQ ID NO: 1) or the domain from amino acids 563–609 of the sequence shown in FIG. 1F (SEQ ID NO: 4), or an active portion of that domain.

As shown in FIG. 1C, IB1 comprises several distinct domains. The 47 amino acid insert contains a putative helix-loop-helix domain as well as a PID. PID domains have an average length of 100–160 amino acids and consist of four conserved blocks. The first block of the PID domain of IB1 is contained within the 47 amino acid insert. This and the neighbouring HLH domain may allow for protein-protein interactions, possibly with other members of the tyrosine kinase signalling pathway or with transcription factors. Computer analysis also showed two acidic helicoidal structures (aa 31–61 and 114–125 in the rat IB1 sequence (SEQ ID NO: 2)) and a proline rich region (aa 292–366). Putative nuclear localization signals were found at aa 163–190 and 242–270.

A polypeptide according to the present invention may be isolated and/or purified (e.g. using an antibody) for instance after production by expression from encoding nucleic acid (for which see below). Polypeptides according to the present invention may also be generated wholly or partly by chemical synthesis. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A polypeptide, peptide fragment, allele, mutant or variant according to the present invention may be used as an immunogen or otherwise in obtaining specific antibodies. Antibodies are useful in purification and other manipulation of polypeptides and peptides, diagnostic screening and therapeutic contexts. This is discussed further below.

A polypeptide according to the present invention may be used in screening for molecules which affect or modulate its activity or function. Such molecules may be useful in a therapeutic (possibly including prophylactic) context.

The IB1 polypeptides can also be linked to a coupling partner, e.g. an effector molecule, a label, a drug, a toxin and/or a carrier or transport molecule. Techniques for coupling the peptides of the invention to both peptidyl and non-peptidyl coupling partners are well known in the art. In one embodiment, the carrier molecule is a 16 aa peptide sequence derived from the homeodomain of Antennapedia (e.g. as sold under the name "Penetratin"), which can be coupled to a peptide via a terminal Cys residue. The "Penetratin" molecule and its properties are described in WO 91/18981.

IB1 Antagonists

IB1 antagonists include substances which have one or more of the following properties:

(a) substances capable of inhibiting expression of IB1;

(b) substances capable of reducing the levels of IB1 present in a target tissue or cell type by binding to and neutralizing the IB1; and/or, (c) substances capable of counteracting a biological property of IB1 protein.

An example of an IB1 antagonist is an antibody capable of specifically binding to IB1 protein. Anti-IB1 antibodies and their production are discussed below.

Anti-IB1 Antibodies

A further important use of the IB1 polypeptides is in raising antibodies that have the property of specifically binding to the IB1 polypeptides, or fragments or active portions thereof. As mentioned above, anti-IB1 antiserum was prepared against recombinant IB1 (amino acids 1–280). These antibodies were raised in a rabbit and are polyclonal. The antibodies were affinity purified and are useful tools as they can recognise IB1 epitope(s). These and other antibodies that can be made based on the disclosure herein can be used as a diagnostic tools and in the characterisation of IB1.

It is possible to produce monoclonal antibodies to IB1 protein and the techniques for doing this are well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184.187, GB-A-2188638 or EP-A-239400. A hybridoma producing a monoclonal antibody may be subject to genetic mutation or other changes, which may or may not alter the binding specificity of antibodies produced.

The provision of the novel IB1 polypeptides enables for the first time the production of antibodies able to bind it specifically. Accordingly, a further aspect of the present invention provides an antibody able to bind specifically to the polypeptide whose sequence is given in FIG. 1A (SEQ ID NO: 2) or 1F (SEQ ID NO: 4). Such an antibody may be specific in the sense of being able to distinguish between the polypeptide it is able to bind and other human polypeptides for which it has no or substantially no binding affinity (e.g. a binding affinity of about 1000× worse). Specific antibodies bind an epitope on the molecule which is either not present or is not accessible on other molecules. Antibodies according to the present invention may be specific for the wild-type polypeptide. Antibodies according to the invention may be specific for a particular mutant, variant, allele or derivative polypeptide as between that molecule and the wild-type IB1 polypeptide, so as to be useful in diagnostic and prognostic methods as discussed below. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80–82, 1992). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanised antibodies in which CDRs from a non-human source are grafted onto human framework regions, typically with the alteration of some of the framework amino acid residues, to provide antibodies which are less immunogenic than the parent non-human antibodies, are also included within the present invention.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser exciting dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor. Antibodies may modulate the activity of the polypeptide to which they bind and so, if that polypeptide has a deleterious effect in an individual, may be useful in a therapeutic context (which may include prophylaxis).

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

Diagnostic Methods

A number of methods are known in the art for analysing biological samples from individuals to determine whether the individual carries a IB1 allele predisposing them to may be used as markers for human genetic diseases such as diabetes; neurological disorders including neurodegenerative diseases, such as dementia, Parkinsonism, and Alzheimer's disease; refractory epilepsy (familial forms); neuronal disabilities such as speech disorders and memory alteration; neuronal or glial tumours such as neuroblastoma or glioblastoma; autoimmune disease affecting the CNS such as systematic lupus erythromatosis (SLE); diabetes; heart diseases such as myocardial infarct and ischemia as apoptosis is involved in areas surrounding infarct; and brain attack, in particular in the prevention of apoptosis in ischemia or infarct. The purpose of such analysis may be used for diagnosis or prognosis, to assist a physician in determining the severity or likely course of the condition and/or to optimise treatment of it. Alternatively, the methods can be used to detect IB1 alleles that are statistically associated with a susceptibility to these conditions in the future, e.g. identifying individuals who would benefit from regular screening or prophylactic treatment.

Broadly, the methods divide into those screening for the presence of IB1 nucleic acid sequences and those that rely on detecting the presence or absence of the IB1 polypeptide. The methods make use of biological samples from individuals that are suspected of contain the nucleic acid sequences or polypeptide. Examples of biological samples include blood, plasma, serum, tissue samples, tumour samples, saliva and urine.

Exemplary approaches for detecting IB1 nucleic acid or polypeptides include:

(a) comparing the sequence of nucleic acid in the sample with the IB1 nucleic acid sequence to determine whether the sample from the patient contains mutations; or, (b) determining the presence in a sample from a patient of the polypeptide encoded by the IB1 gene and, if present, determining whether the polypeptide is full length, and/or is mutated, and/or is expressed at the normal level; or, (c) using DNA fingerprinting to compare the restriction pattern produced when a restriction enzyme cuts a sample of nucleic acid from the patient with the restriction pattern obtained from normal IB1 gene or from known mutations thereof; or, (d) using a specific binding member capable of binding to a IB1 nucleic acid sequence (either a normal sequence or a known mutated sequence), the specific binding member comprising nucleic acid hybridisable with the IB1 sequence, or substances comprising an antibody domain with specificity for a native or mutated IB1 nucleic acid sequence or the polypeptide encoded by it, the specific binding member being labelled so that binding of the specific binding member to its binding partner is detectable; or, (e) using PCR involving one or more primers based on normal or mutated IB1 gene sequence to screen for normal or mutant IB1 gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, molecules and receptors and complementary nucleotide sequences. The skilled person will be able to think of many other examples and they do not need to be listed here. Further, the term "specific binding pair" is also applicable where either or both of the specific binding member and the binding partner comprise a part of a larger molecule. In embodiments in which the specific binding pair are nucleic acid sequences, they will be of a length to hybridise to each other under the conditions of the assay, preferably greater than 10 nucleotides long, more preferably greater than 15 or 20 nucleotides long.

In most embodiments for screening for IB1 susceptibility alleles, the IB1 nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

A variant form of the IB1 gene may contain one or more insertions, deletions, substitutions and/or additions of one or more nucleotides compared with the wild-type sequence which may or may not disrupt the gene function. Differences at the nucleic acid level are not necessarily reflected by a difference in the amino acid sequence of the encoded polypeptide, but may be linked to a known dysfunction. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/ or addition of one or more amino acids or regions in the polypeptide. A mutation in a promoter sequence or other regulatory region may prevent or reduce expression from the gene or affect the processing or stability of the mRNA transcript.

There are various methods for determining the presence or absence in a test sample of a particular nucleic acid sequence, such as the sequence shown in FIG. 1A (SEQ ID NO: 1) or 1E (SEQ ID NO: 3) or a mutant, variant or allele thereof. Exemplary tests include nucleotide sequencing, hybridization using nucleic acid immobilized on chips, molecular phenotype tests, protein truncation tests (PTT), single-strand conformation polymorphism (SSCP) tests, mismatch cleavage detection and denaturing gradient gel electrophoresis (DGGE). These techniques and their advantages and disadvantages are reviewed in Nature Biotechnology, 15:422–426, 1997.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RNAses.

Nucleic acid in a test sample may be sequenced and the sequence compared with the sequence shown in FIG. 1A (SEQ ID NO: 1) or 1E (SEQ ID NO: 3), to determine whether or not a difference is present. If so, the difference can be compared with known susceptibility alleles to determine whether the test nucleic acid contains one or more of the variations indicated.

Since it will not generally be time- or labour-efficient to sequence all nucleic acid in a test sample or even the whole IB1 gene, a specific amplification reaction such as PCR using one or more pairs of primers may be employed to amplify the region of interest in the nucleic acid, for instance the IB1 gene or a particular region in which mutations associated with a susceptibility to one of the conditions mentioned above. The amplified nucleic acid may then be sequenced as above, and/or tested in any other way to determine the presence or absence of a particular feature. Nucleic acid for testing may be prepared from nucleic acid removed from cells or in a library using a variety of other techniques such as restriction enzyme digest and electrophoresis.

Nucleic acid may be screened using a variant- or allele-specific probe. Such a probe corresponds in sequence to a region of the IB1 gene, or its complement, containing a sequence alteration known to be associated with a susceptibility to the conditions mentioned above. Under suitably stringent conditions, specific hybridisation of such a probe to test nucleic acid is indicative of the presence of the sequence alteration in the test nucleic acid. For efficient screening purposes, more than one probe may be used on the same test sample.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected.

An alternative or supplement to looking for the presence of variant sequences in a test sample is to look for the presence of the normal sequence, e.g. using a suitably specific oligonucleotide probe or primer.

Use of oligonucleotide probes and primers has been discussed in more detail above.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RNAse A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal IB1 gene (either sense or anti-sense strand) in which mutations are known to occur may be annealed to test nucleic acid and the presence or absence of a mis-match determined. Detection of the presence of a mis-match may indicate the presence in the test nucleic acid of a mutation. On the other hand, an oligonucleotide probe that has the sequence of a region of the IB1 gene including a mutation may be annealed to test nucleic acid and the presence or absence of a mis-match determined. The absence of a mis-match may indicate that the nucleic acid in the test sample has the normal sequence. In either case, a battery of probes to different regions of the gene may be employed.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

The presence or the absence of an important regulatory element in a promoter or other regulatory sequence located in introns may also be assessed by determining the level of mRNA production by transcription or the level of polypeptide production by translation from the mRNA.

A test sample of nucleic acid may be provided for example by extracting nucleic acid from cells, e.g. in saliva or preferably blood, or for pre-natal testing from the amnion, placenta or foetus itself.

There are various methods for determining the presence or absence in a test sample of a particular polypeptide, such as the polypeptide with the amino acid sequence shown in FIG. 1A (SEQ ID NO: 2), 1D (SEQ ID NOS: 2 and 17) or 1F (SEQ ID NO: 4) or an amino acid sequence mutant, variant or allele thereof.

A sample may be tested for the presence of a binding partner for a specific binding member such as an antibody (or mixture of antibodies), specific for one or more particular variants of the polypeptide shown in FIG. 1A (SEQ ID NO: 2), 1D (SEQ ID NOS: 2 and 17), or 1F (SEQ ID NO: 4).

A sample may be tested for the presence of a binding partner for a specific binding member such as an antibody (or mixture of antibodies), specific for the polypeptide shown in FIG. 1A (SEQ ID NO: 2), 1D (SEQ ID NOS: 2 and 17) or 1F (SEQ ID NO: 4).

In such cases, the sample may be tested by being contacted with a specific binding member such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the polypeptide whose sequence is shown in FIG. 1A (SEQ ID NO: 2) or 1F (SEQ ID NO: 4), or if it is a mutant or variant form. Amino acid sequence is routine in the art using automated sequencing machines.

Therapeutics

Pharmaceuticals and Peptide Therapies

IB1 polypeptides and antagonists and agonists may be useful in the treatment of a wide range of disorders because of the biological activities of IB1. Broadly the conditions that can be treated fall into four main areas, diabetes, neurological disorders, cancer and in the inhibition or promotion of apoptosis.

For the treatment of diabetes, IB1 or an IB1 agonist can be used to elevate the insulin content and secretion in a patient and/or to elevate GLUT2 expression and therefore the sensitivity of a patient to glucose. Further, the anti-apoptotic effects of IB1 can be used to inhibit the apoptosis of β-cells which occurs when β cell exhaustion occurs in the type II diabetes. IB1 could also be used to inhibit the apoptosis seen during the autoimmune destruction in type I diabetes. IB1 can also help to improve cell survival when β cells are engineered for xenotransplantation or encapsulation, e.g. in a biocompatible polymer.

In the treatment of neurological disorders, IB1 antagonists can be used to promote cell death by reducing or removing the anti-apoptotic effects of IB1. This could have applications in the treatment of brain tumours such as neuroblastomas and glioblastomas, and in the treatment of refractory epilepsy. On the other hand, IB1 or IB1 agonists could be used to promote cell survival in neurons and consequently be useful therapies for neurodegenerative disorders, ischemic diseases, autoimmune diseases of the CNS, infarct of the brain to promote cell survival in cells surrounding the infarct, Parkinsonism and to promote cell survival in sections of the spine.

In the treatment of cancer, IB1 antagonists can be used to promote cell death in tumour cells in cancers in which the cells do not undergo an apoptotic program. In surrounding, healthy tissues, IB1 or IB1 agonists could be used help protect the cells from the effects of cancer treatments. In these embodiments, clearly some form of selective delivery of the agents is preferred.

From the above applications, IB1 and IB1 agonists have a general role in the protection if cells from apoptosis, while conversely IB1 antagonists can be used to promote cell death.

The IB1 polypeptides, antagonists (e.g. antibodies), peptides and nucleic acid of the invention can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, eg in a viral vector (a variant of the VDEPT technique—see below) The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO90/07936).

A composition may be administered alone or in combination with other treatments, either simultaneously or sequentially, dependent upon the condition to be treated.

Methods of Gene Therapy

As a further alternative, the nucleic acid encoded the authentic biologically active IB1 polypeptide could be used in a method of gene therapy, to treat a patient who is unable to synthesize the active polypeptide or unable to synthesize it at the normal level, thereby providing the effect provided by wild-type IB1 and suppressing the occurrence of diabetes in the target cells.

Vectors such as viral vectors have been used in the prior art to introduce genes into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted tumour cells, providing long lasting effect, or alternatively the treatment may have to be repeated periodically.

A variety of vectors, both viral vectors and plasmid vectors, are known in the art, see U.S. Pat. No. 5,252,479 and WO93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

As mentioned above, the aim of gene therapy using nucleic acid encoding the IB1 polypeptide, or an active portion thereof, is to increase the amount of the expression product of the nucleic acid in cells in which the level of the wild-type IB1 polypeptide is absent or present only at reduced levels. Target cells for gene therapy include insulin secreting β-cells or any neuron derived cells. Cell engineering can be used to provide the overexpression or repression of IB1 in transfected cell lines which can then be subsequently transplanted to humans. Gene therapy can be employed using a promoter to drive IB1 expression in a tissue specific manner (i.e. an insulin promoter linked to IB1 cDNA will overexpress IB1 in β-cells and transiently in the brain). If defective function of IB1 is involved in neurological disease, IB1 can be overexpressed in transformed cell lines for transplantation.

Gene transfer techniques which selectively target the IB1 nucleic acid to target tissues are preferred. Examples of this included receptor-mediated gene transfer, in which the nucleic acid is linked to a protein ligand via polylysine, with the ligand being specific for a receptor present on the surface of the target cells.

IB1 expressing vectors (used in several vectors such as adenovirus or retrovirus could be used if stably integrated as an anti-apoptotic gene product. This allows cells to survive the stressful event of encapsulation for xenotransplantation, and/or to survive hypoxia if transplanted into a low oxygen environment such as the peritoneum. The cells can then survive and, if needed, secrete IB1. The IB1 could be useful in the treatment or prevention of conditions described above, e.g. to promote cell survival if secreted into the central nervous system in the treatment of neurodegenerative disease.

Antisense technology based on the IB1 nucleic acid sequences is discussed above.

Methods of Screening for Drugs

A polypeptide according to the present invention may be used in screening for molecules which affect or modulate its activity or function. Such molecules may be useful in a therapeutic (possibly including prophylactic) context.

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility.

A method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Combinatorial library technology provides an efficient way of testing a potentially vast number of different substances for ability to modulate activity of a polypeptide. Such libraries and their use are known in the art. The use of peptide libraries is preferred.

Prior to or as well as being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide. Alternatively, the screen could be used to screen test substances for binding to a IB1 specific binding partner, to find mimetics of the IB1 polypeptide, e.g. for testing as therapeutics.

In one embodiment, the present invention provides a method for screening test substances for a biological activity of an IB1 polypeptide, the method employing a cell line which does not express IB1 polypeptide, the cell line being transformed with an expression vector comprising a reporter gene under the specific control of GTII promoter, the method comprising exposing cell line to a test substance and determining whether expression of the reporter gene occurs. Thus, the binding of a test substance to the GTII promoter element causes a signal from the reporter (e.g. a colour change or the expression of a detectable product).

Following identification of a substance which modulates or affects polypeptide activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition to a patient, e.g. for treatment (which may include preventative treatment) of diabetes, use of such a substance in manufacture of a composition for administration, and a method of making a pharmaceutical composition comprising admixing such a substance with a pharmaceutically acceptable excipient, vehicle or carrier, and optionally other ingredients.

A substance identified using as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. Alanine scans of peptide are commonly used to refine such peptide motifs. These parts or residues constituting the active region of the compound are known as its "pharmacophore".

Once the pharmacophore has been found, its structure is modelled to according its physical properties, eg stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

Screening for Substances Affecting IB1 Expression

The present invention also provides the use of all or part of the nucleic acid sequence of the IB1 promoter in methods of screening for substances which modulate the activity of the promoter and increase or decrease the level of IB1 expression.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction. Use of a reporter gene facilitates determination of promoter activity by reference to protein production.

Further provided by the present invention is a nucleic acid construct comprising a IB1 promoter region set out in FIG. 5 or a fragment, mutant, allele, derivative or variant thereof able to promoter transcription, operably linked to a heterologous gene, e.g. a coding sequence. A "heterologous" or "exogenous" gene is generally not a modified form of IB1 Generally, the gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectrophotometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to or a limitation of the present invention.

Nucleic acid constructs comprising a promoter (as disclosed herein) and a heterologous gene (reporter) may be employed in screening for a substance able to modulate activity of the promoter. For therapeutic purposes, e.g. for treatment of diabetes a substance able to up-regulate expression of the promoter directing the expression of normal may be sought. Alternatively, substances to down-regulate the promoter may help to prevent or inhibit the production of mutated IB1 polypeptide, if this is an agent implicated in the development of diabetes. A method of screening for ability of a substance to modulate activity of a promoter may comprise contacting an expression system, such as a host cell, containing a nucleic acid construct as herein disclosed with a test or candidate substance and determining expression of the heterologous gene.

The level of expression in the presence of the test substance may be compared with the level of expression in the absence of the test substance. A difference in expression in the presence of the test substance indicates ability of the substance to modulate gene expression. An increase in expression of the heterologous gene compared with expression of another gene not linked to a promoter as disclosed herein indicates specificity of the substance for modulation of the promoter.

A promoter construct may be introduced into a cell line using any technique previously described to produce a stable cell line containing the reporter construct integrated into the genome. The cells may be grown and incubated with test compounds for varying times. The cells may be grown in 96 well plates to facilitate the analysis of large numbers of compounds. The cells may then be washed and the reporter gene expression analysed. For some reporters, such as luciferase the cells will be lysed then analysed.

Following identification of a substance which modulates or affects promoter activity, the substance may be investigated further. Furthermore, it may be manufactured and/or used in preparation, i.e. manufacture or formulation, of a composition such as a medicament, pharmaceutical composition or drug. These may be administered to individuals.

Materials and Methods

Construction of an INS-1 cDNA Expression Library and Cloning of the IB1 cDNA

An oligo(dT)-primed cDNA was generated from 10 µg of poly(A)$^+$ RNA obtained from the differentiated INS-1 insulin secreting cell line using a cDNA synthesis kit (Stratagene, La Jolla, Calif.) according to the manufacturer's instructions. The cDNAs were cloned into the EcoRI and XhoI sites of the LambdaZap Express expression vector (Stratagene, La Jolla, Calif.). A total of $2 \times 10^6$ colonies were screened by the procedure described by Singh et al (38) using as probe concatenated GTII oligonucleotides. 5 µg of double stranded GTII oligonucleotides (5'-GTAAAGGGTGTATTGATTGGATTACCATCA ATACTCAGCTTCT-3') (SEQ ID NO: 54) were filled in by the Klenow fragment of DNA polymerase I in the presence of ($\alpha^{32}$P)deoxycytosine-triphosphate and the free nucleotides separated through a G-50 spun column. These labelled oligonucleotides were subsequently ligated to generate the concatanated probe. The expression cloning was performed exactly as previously described for the SouthWestern experiments, except that we used 10 ug/ml of single stranded DNA in place of poly dI/dC in a total reaction volume of 250 ml(3). One IB1 positive clone was obtained from the screening and the cDNA sequenced in both 5' and 3' orientations.

Cell Lines

The transplantable X-ray induced rat insulinoma INS-1 cell line was provided by Asfari et al. and grown as described (1). The mouse insulin-producing βTC3 cell line, the hamster glucagon-producing InR1-G9 cells and the kidney-derived COS-7 cell line were cultured in RPMI 1640 medium containing 10% fetal calf serum, 2 mM L-glutamine, 100 U/ml penicillin and 100 mg/ml streptomycin(9,40).

Plasmid Constructions, Transient Transfections, CAT and Luciferase Assays

The eukaryotic expression vector encoding IB1 was constructed by inserting the IB1 cDNA in the NheI/XhoI sites of the CMV-driven plasmid PBKS (Stratagene, La Jolla, Calif.) to generate the PBKS-IB1 vector. PCR mutagenesis was used to add a FLAG epitope (Kodak, New Haeven, Conn.) just C-terminal of the initiating methionine of the IB1 cDNA in the PBKS-IB1 construct. Dideoxy sequencing of the resulting plasmids was used to confirm the correct sequence of the clones thus obtained. The −410 bp of the rat insulin II promoter and the −338 bp of the murine GLUT2 promoter were cloned 5' of the luciferase gene of the pGL3Basic vector (Promega, Madison, Wis.). The RIPE3 double-stranded oligonucleotides (5-GATCTGGAAACTGCAGCTTCAGCCCCTCT GGCCATCTGCTGATCCG-3') (SEQ ID NO: 55) were multimerized, filled-in by Klenow, and blunt-end ligated into the SmaI site of the SV40 early minimal promoter linked to a luciferase gene (pGL3 promoter, Promega). The five copies of the RIPE3 element cloned into pGL3promoter were sequenced. The −316, −289, −254, −188, −159 and −66 bp of the rat I insulin promoter linked to the CAT reporter gene were kindly provided by Jacques Philippe from the University Medical School of Geneva.

All constructs were transiently transfected using the cationic reagent DOTAP in solution as recommended by the supplier (Boehringer Mannheim). Two µg of the reporter DNAs (luciferase or CAT constructs) with 1 µg of transactivator (PBKS or PBK/IB1) were used for $1-2 \times 10^6$ cells and incubated for 48–56 hours. In some transfection experiments, co-transfection with 500 ng of the herpes simplex virus thymidine kinase (HSV-TK) promoter driving the Renilla luciferase gene (Promega, Madison, Wis.) were included in order to control the transfection efficiency. The transfected cells were harvested with Promega lysis buffer, the cellular debris removed, and the supernatant collected. Protein concentrations were determined using the Bio-Rad protein assay (Bio-Rad Laboratories, Richmond, Calif.). Luciferase activities were measured twice with 50 to 100 µg of protein extracts from each transfected plate according to the protocol of Brasier et al(4).

Gel Shift Assays and SouthWestern Experiments

Nuclear and cytoplasmic extracts were prepared according to the method of Dent and Latchmann (7). The sequences of the oligonucleotides GTII and RIPE3 are described above. Complementary sense and antisense oligonucleotides were hybridized and then filled in by the Klenow fragment of DNA polymerase I in the presence of (α32P) deoxycytosine triphosphate. The end-labelled probe was incubated with 2 µg nuclear extracts exactly as described previously for the band shift assays (3). The SouthWestern experiments were conducted as described with the modifications detailed above (3). The in vitro translation experiments were conducted using the coupled translation-traduction kit (TNT) from Promega (Madison, Mich.) and according to the manufacturer's instructions in the presence of ($^{35}$S) methionine. The labelled protein was resolved by PAGE on a 10% SDS-containing gel.

RNA and Northern Blot Analysis

The RNA isolation and Northern blot analysis from rat tissues or cell lines were conducted exactly as previously described (3). The rat pancreatic islets were isolated by the method of Gotoh et al (15).

Preparation of Antisera

Anti-IB1 antiserum was prepared using a cDNA fragment encoding the first 280 amino acids of the protein. This fragment was inserted into the His-tagged pQE-9 expression vector (Quiagen, Basel, Switzerland), expressed and subsequently purified through a Ni$^{2+}$-containing column following instructions from the manufacturer (Quiagen, Basel, Switzerland) and used to elicit polyclonal antibodies in rabbits. To affinity-purified the antibodies, the Ni$^{2+}$-column purified 1-280 aa of the recombinant protein was immobilized onto a nitrocellulose membrane and the rabbit serum purified by several steps of incubation with this membrane in PBS (phosphate-buffered saline) buffer and elution in 0.2M Tris-glycine at pH 2.8, followed by neutralization to pH ~7.5.

Immunohistochemistry

Adult mice under deep anesthesia were perfused with PBS and pancreata were quickly removed, incubated for 6 hours in 4% paraformaldehyde and processed for paraffin embedding. Sections of 8 μm were used for immunocytochemistry. In brief, sections were incubated in the presence of 5% $H_2O_2$ for 30 min at room temperature, washed in PBS and incubated overnight in the presence of 5% bovine serum albumin dissolved in PBS buffer containing 0.5% Triton X-100 and 2% goat serum. The sections were then incubated for 14 hours at 4° C. with the affinity-purified preimmune or immune anti IB1 serum (dilution 1/200) and then for 2 hours at room temperature with the secondary antibody (biotinylated goat anti-rabbit IgG from Vector/Reactolab S.A.) and 2 hours at room temperature with avidin-biotinylated peroxidase complex (ABC, Vector Reactolab SA). The peroxidase reaction was finally visualized with 3,3'-diaminobenzidine tetrahydrochloride dihydrate (Fluka, Buchs, Switzerland) in PBS containing 0.2% $H_2O_2$. Photographs were taken with a Leica microscope using transmitted light optics and Kodak Ektachrome EPJ 320 films. For immunostaining, the βTC3 or the transfected COS-7 cells, these cells were plated on glass coverslips 48 hours before the experiment. The cells were fixed in ice-cold methanol/acetone (50:50) and processed as described above with the ABC detection kit. In COS-7 cells, the detection of the FLAG epitope was obtained using as a secondary antibody, the commercially available (Kodak, New Haeven, Conn.) monoclonal mouse antibody directed against the FLAG subsequently visualized with fluoroscein isothiocyanate (FITC)-labelled goat anti-mouse antibodies. The rabbit anti-IB1 antibodies were detected using a Texas red-labelled goat anti-rabbit antibody. The fluorescence images were obtained with 1600 ASA Kodak films.

Sequence of Human IB1 cDNA

A radiolabelled rat IB1 cDNA was initially used to screen at low stringency a human insulinoma cDNA library. Briefly, poly(A)+RNA was isolated using the Promega PolyA+RNA purification kit (Promega, Madison, Wis.) and a cDNA library was constructed using the α/Zapp II Express expression vector (Stratagene, La Jolla, Calif.) according to the manufacturer's instructions. One positive clone was subjected to sequence analysis which revealed that the 1.8-kb insert was homologous to nucleotides 1440 to 2252 of rat IB1 cDNA. Two 5' RACE reactions (Boehringer-Mannheim, Mannheim, Germany) were used to obtain part of the 5' sequence of the human IB1 cDNA. The first step in these two reactions was an RT-PCR amplification on total RNA isolated from a human glucagonoma. RT-PCR amplifications was performed using an oligo-dT-anchor primer (SEQ ID NO: 18) (provided in the kit) and as antisense primers oligonucleotides RACE-1 or -2 (SEQ ID NOS: 20–21), respectively (Table 1). Two consecutive PCR amplification steps were then performed on the RT-PCR product using the PCR anchor primer (SEQ ID NO: 19) (provided in the kit) and as antisense primers the nested oligonucleotides RACE-3 and -4 (SEQ ID NOS: 22–23) (for the first reaction) or RACE-5 and -6 (SEQ ID NOS: 24–25) (for the second reaction). The first RACE reaction yielded the sequence corresponding to nucleotides 70 to 290 whereas the second RACE reaction gave sequences 480 to 711 of human IB1 cDNA. The remaining sequences of human IB1 cDNA (nucleotides 1 to 69, 291 to 479 and 712 to 1439) were deduced by comparing the sequence of the rat IB1 cDNA to genomic sequences obtained from a bacterial artificial chromosome (BAC) library of human genomic DNA (see below).

Screening of a BAC Library of Human Genomic DNA and Sequence Analysis of BAC Clones A BAC library of human genomic DNA (Research Genetics, Rockville, Md.) was screened using as a probe the 1.8-kb fragment corresponding to the 3' end of the human IB1 cDNA, as described above. Positive BAC clones were selected, purified according to the instructions of the manufacturer and digested with BamHI/BglII for analysis by Southern blotting according to standard protocols. Genomic DNA extracted from circulating leukocytes of an apparently healthy individual was used for comparison.

Fragments generated by BamHI/BglII digest of two positive BAC clones were subcloned within a KS=/−Bluescript vector. These subclones were screened using two non-overlapping probes, the 1.8 kb fragment corresponding to the 3' end of human IB1 cDNA, as described above, or a 955-bp fragment corresponding to the 5' end of rat IB1 cDNA. Positive clones were identified and subjected to sequence analysis using T3 and T7 oligonucleotides. A walking approach was used to obtain intervening sequences. Finally, two pairs of oligonucleotides (IB1–787F and IB-1326R; IB1-1346F and IB1-1602R) (SEQ ID NOS: 26–29) designed based on the sequence of the human IB1 cDNA were used for PCR-amplification using the BAC clone or Bluescript subclones as templates. PCR amplified fragments were either cloned within the pGEM-T Easy plasmid factor (Promega) or sequenced directly.

Fluorescent in-situ Hybridization (FISH)

FISH analysis was performed using as probes the products of BAC-A or BAC-B clones digested with BamHI/BglII, respectively. An aliquot of fresh peripheral blood cells was washed twice in PBS and cultured for 2–3 days in RPMI 1640 containing 20% fetal calf serum. Cells were incubated with colcemid, treated with a hypotonic KCl solution and fixed with an acetic acid:methanol (1:3) solution. Chromosome slides were denatured in a solution containing 70% formamide in 2×SSC at 75 C for 2 min. A total of ~250 ng of DNA were labelled by nick-translation incorporating biotin-dUTP (Boehringer-Mannheim) and then treated with DNase I (Pharmacia, Uppsala, Sweden) at a concentration of 50 pg/μl for 20 min at room temperature. DNase I was inactivated at 70 C for 10 min. Labelled probe were denatured at 37 C for 10 min in 25 μl Hybridsol VII (Oncor), allowed to reanneal to human Cot1 DNA (3 μg) at 37 C for 15 to 30 min, and hybridized overnight. The hybridization signals were detected using FITC-avidin or rhodamine-conjugated anti-digoxigenin monoclonal antibodies (Boehringer-Mannheim).

Radiation Hybrid Mapping

Radiation hybrid mapping was used to precisely map the IB1 gene. In the first series of experiments, PCR amplification was performed using one pair of oligonucleotides (IB1-1346F and IB1-1602R) (SEQ ID NOS: 28–29) were originally designed according to the sequence of human IB1 cDNA (nucleotides 1346 to 1602). Subsequently, a second set of oligonucleotides (IB1-f and IB1-r) were designed. Amplification was performed in 96-well plates (Polyfiltronics, Rockland, Mass.). Each reaction contained 25 ng DNA, 0.3 mM of each primer, 0.2 mM dNTP's, 0.2 unit AmpliTaq polymerase and 1×PCR buffer (Perkin-Elmer, Norwalk, Conn.) (5% DMSO was also added when using the second set of primers) in a total volume of 20 μl. The PCR program consisted of a 2 min (4 min for the second set of primers) initial denaturation at 94 C followed by 35 cycles of 94 C for 30 sec (1 min), 58 C (62 C) for 1 min, 72 C for 1 min and a final extension of 3 min (4 min) at 72 C. Amplicons were scored after electrophoresis through a 3% (w/v) 3:1 NuSieve agarose gel (FMC BioProducts, Rockland Me.). The IB1 STS's were evaluated by somatic cell and radiation hybrid on both the NIGMS Human/Rodent somaticcell hybrid Mapping Panel #2 (Coriell Institute for Medical Research, Camden N.J.) and the PCRable DNA Monochromosomal Somatic Cell Hybrid Panel (BIOS, New Haven Conn.). The Stanford 3 (G3) and Genebridge 4 (GB4) radiation hybrid panels (Research Genetics) were used to more precisely localize the genes. The vectors from G3 and BG4 panels were analyzed using the RHMAP RH2PT Version 3.0 (57) and the RHMAPPER Version 1.1 (58) respectively.

Northern Blot Analysis of IB1 Expression in Human Tissues

A total of 2 μg of poly(A)+RNA isolated from various human tissues (Clontech) were hybridized at 42 C with the $^{32}$P-labelled 1.8 kb probe corresponding to the 3' end of the human IB1 cDNA (as described above) in a 5×SSC buffer continuing 0.1 M NaPO$_4$, 10 mmol/l EDTA, 50% (v/V) formamide, 1% (w/v) SDS, 5×Denhardt's and 0.1 mg/ml tRNA. After washing, the filter was exposed.

RESULTS

EXAMPLE 1

Isolation and Sequence Analysis of the IB1 cDNA

The identification of a cis element named GTII located in the proximal region of the GLUT2 promoter which is functionally important to confer pancreatic expression of the gene was the initial step towards the identification of putative islet-specific trans-acting factors (3). Therefore, the inventors constructed a library using INS-1 cells as GTII-binding activity is restricted to insulin-secreting cells and its abundance was highest in a cell line that expresses high amounts of endogenous GLUT2. A poly-dT primed INS-1 cDNA expression libary was therefore constructed and screened by the procedure described by Singh et al (38) using as a probe concatanated GTII oligonucleotides. One positive clone was isolated from a primary screen of approximatively 2×10$^6$ phage plaques. The 2,990 bp long insert encodes a large open reading frame of 714 amino acids (SEQ ID NO: 1). The gene product contained in this clone was subsequently termed IB1 for Islet-Brain 1 as its expression is mainly restricted to these two tissues, as discussed below. The deduced amino acid sequence (SEQ ID NO: 2) revealed the presence of a putative HLH dimerization domain conserved with other members of the bHLH family (FIG. 1). Using the SOPMA algorithm (self optimized prediction method from alignements, CNRS, Lyon, France), computer analysis predicts two acidic helicoidal structures (a.a. 31–61 and 114–125) and a proline-rich (a.a. 292–366) region in the amino-terminal part of the protein that could act as transactivation domains (25). Putative nuclear localisation signals were also recognized (a.a. 163–190 and 242–270) (8).

EXAMPLE 2

Tissue Distribution of IB1 Expression

Figure 2A:
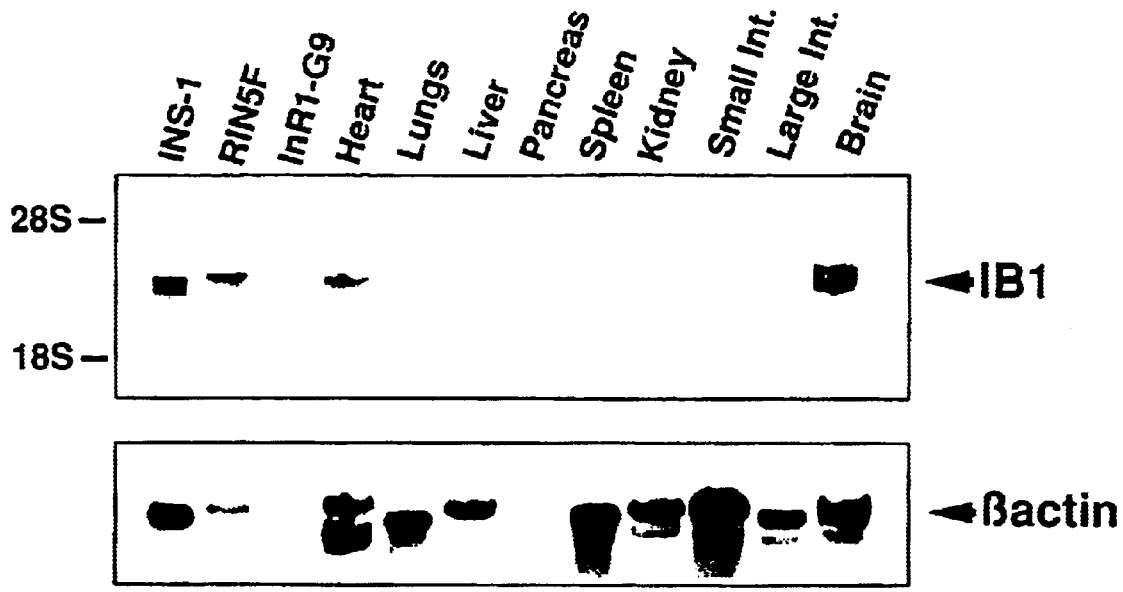
FIG. 2
Tissue-specific Expression of IB1 Gene.
A. The distribution of IB1 transcript in tissues and cell lines was determined by Northern blot analysis using 10 μg of total RNA prepared from INS-1 and RIN5F (two insulin-producing β-cell lines), from InR1-G9 (a glucagon-producing α-cell line) and several rat tissues. IB1 transcripts of 3.0 and 3.2 kb were detected only in the insulin-secreting cell lines and in the brain and to a lesser extent in the heart and kidney. The blot was stripped and rehybridized with a β-actin probe (bottom).
B. Five micrograms of poly(A+) RNA prepared from 2 different insulin-secreting cell lines, from rat liver, kidney and pancreas were similarly analyzed for IB1 gene expression. IB1 transcripts were detected in a cell- and tissue-specific manner.
C. A total of 5 μg of RNA obtained from isolated rat pancreatic islets incubated in 2.8 mM or 30 mM glucose for 14 hours were analyzed by Northern blotting together with rat liver and adipose tissue RNAs. IB1 is abundantly expressed in the isolated islets and its expression is not regulated by glucose.
D. IB1 gene expression in the rat brain. A total of 10 μg RNA extracted from the cortex (lane 1), pituitary gland (lane 2), hypothalamus (lane 3), cerebellum (lane 4) and medulla (lane 5) were separated in a formaldehyde gel and analyzed by Northern blot for IB1 presence. The two IB1 transcripts were detected at high abundance in the cortex and the hypothalamus regions. The same blot was subsequently rehybridized with β-actin (bottom).
Figure 2B:
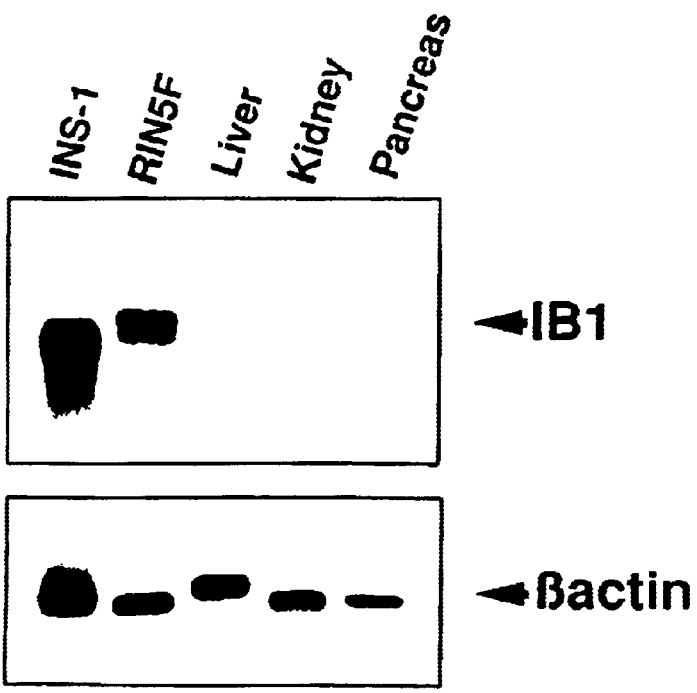
Figure 2D:
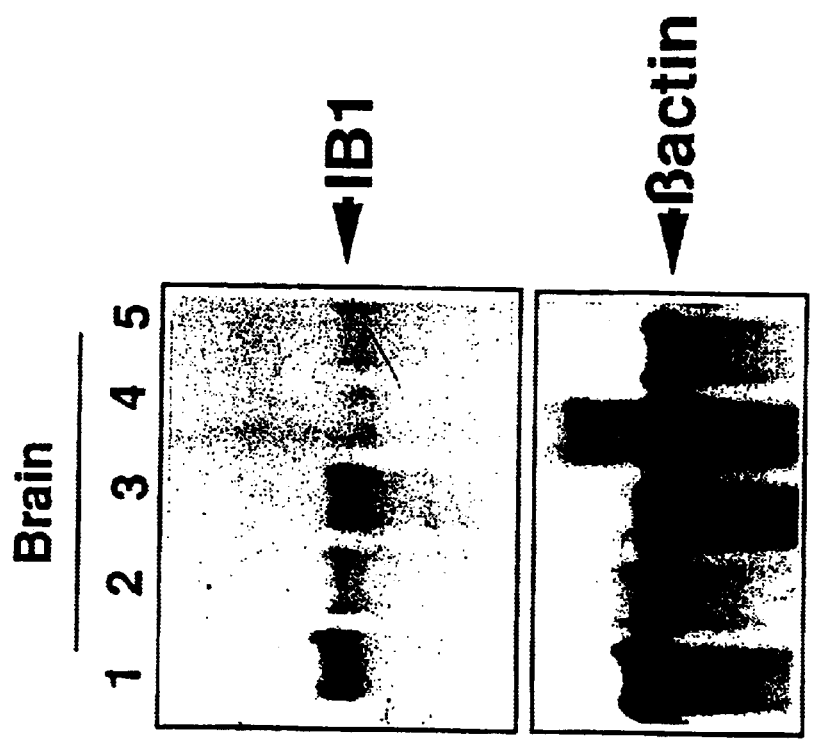
Figure 2C:
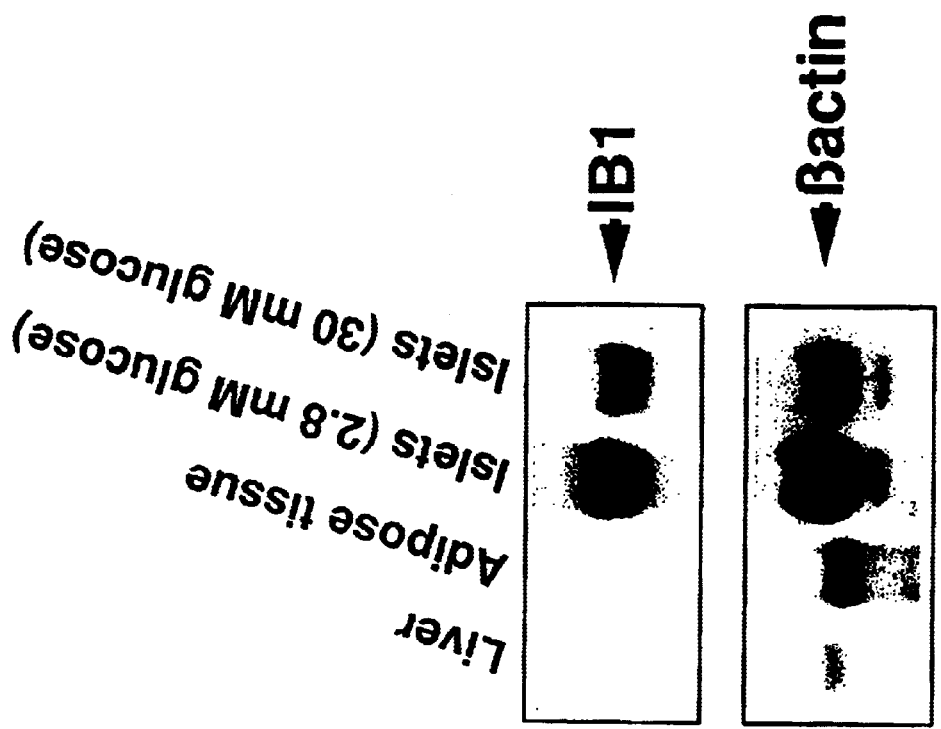

Northern blot analysis of total RNA and polyA$^+$ RNA from several adult rat tissues and cell lines indicated that IB1 is abundantly expressed as a 3 and 3.2 kb transcript in several insulin-secreting cell lines (INS-1 and RIN5F), in isolated pancreatic islets and in the brain (FIG. 2) IB1 transcripts were also detected, although to a lower extent, in the kidney and the heart. In this latter, a single 3.2 kb transcript was detected. In the brain, IB1 expression is highest in the cortex and in the pituitary gland, although the IB1 transcripts were also detected in the hypothalamus, the cerebellum and the medulla (FIG. 2D). In the isolated pancreatic islets, IB1 expression was not regulated by increasing the glucose concentration in the incubation medium from 2.8 mM to 30 mM suggesting that the gene is not transcriptionally regulated by glucose as this is the case for GLUT2 (52). IB1 expression is therefore restricted to a few tissues and, importantly, the IB1 mRNA is not detected in the liver where GLUT2 is abundantly expressed.

EXAMPLE 3

IB1 is Immunodetected in Rat Tissues and in Insulin-secreting Cell Lines

Figure 3A:
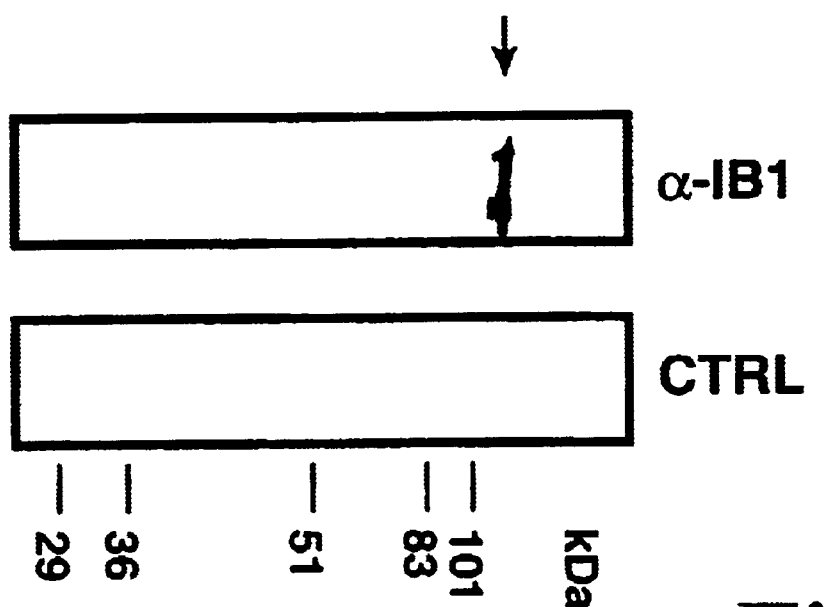
FIG. 3
The IB1 Protein is Detected in Adult RaT Tissues.
A. Immunoblot analysis of IB1. A rabbit polyclonal antibody (α-IB1) was raised towards the N-terminal part of the recombinant protein (aa 1–280) and affinity purified. Western blot analysis of βTC3 whole cell extracts with the α-IB1 antibody demonstrated the presence of a 120 kDa product which was undetected with the preimmune serum (CTRL).
B. Determination of the apparent molecular weight of IB1. In vitro translated IB1 cDNA in the sense (S, T3 RNA-polymerase) or the antisense (AS, T7 RNA-polymerase) orientation in presence of $^{35}$S labelled methionine was separated by SDS-PAGE electrophoresis. An 120 kDa product is detected only in the cDNA translated in the sense orientation.
C. A plasmid containing the IB1 cDNA driven by a CMV promoter or its parent vector was transiently transfected into COS-7 cells and crude cellular extracts (20 μg) of these transfected cells analyzed by Western blotting. Using the α-IB1 antibodies, an approximately 120 kDa protein was detected only in the transfected cells overexpressing IB1.
D. Similar experiments were carried out in transiently transfected COS-7 cells with the pCMV-IB1 vector and cytoplasmic (CE) or nuclear (NE) extracts prepared 48 hours after transfection. By Western blot analysis, IB1 is detected in the cytoplasm and the nucleus of the transfected cells.
E. 20 μg of crude cellular extracts from several rat tissues and of the insulin-secreting β-cell line βTC3 were analyzed by Western blotting using the α-IB1 antibodies. IB1 protein was detected in the brain and the insulin-secreting cell line.
Figure 3B:
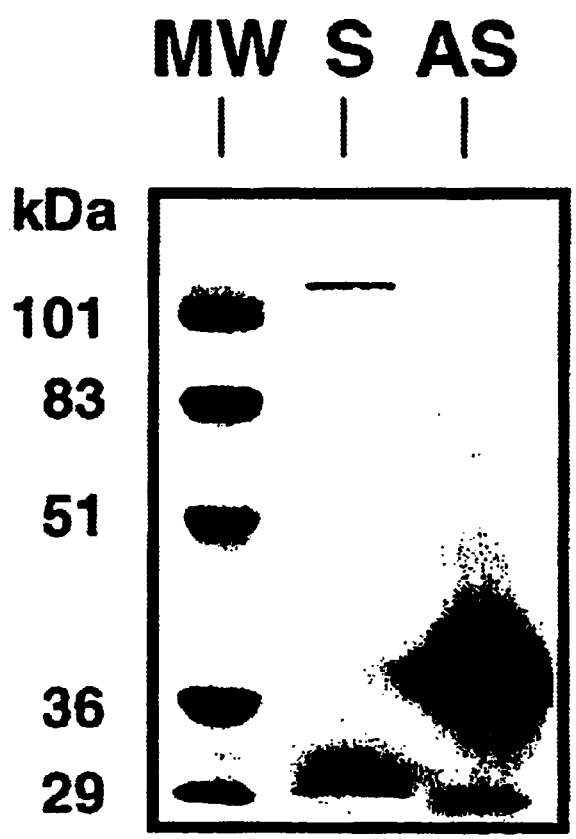
Figure 3C:
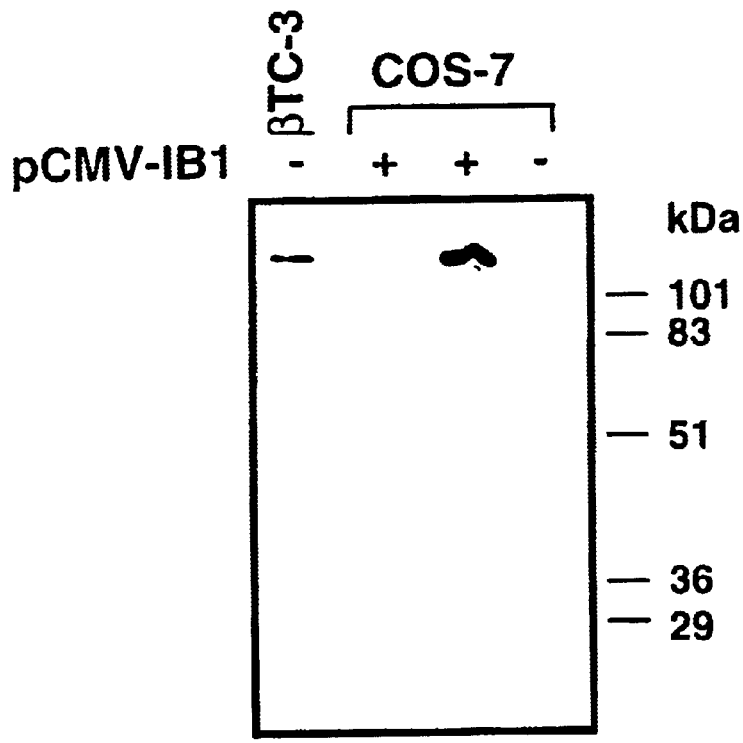
Figure 3D:
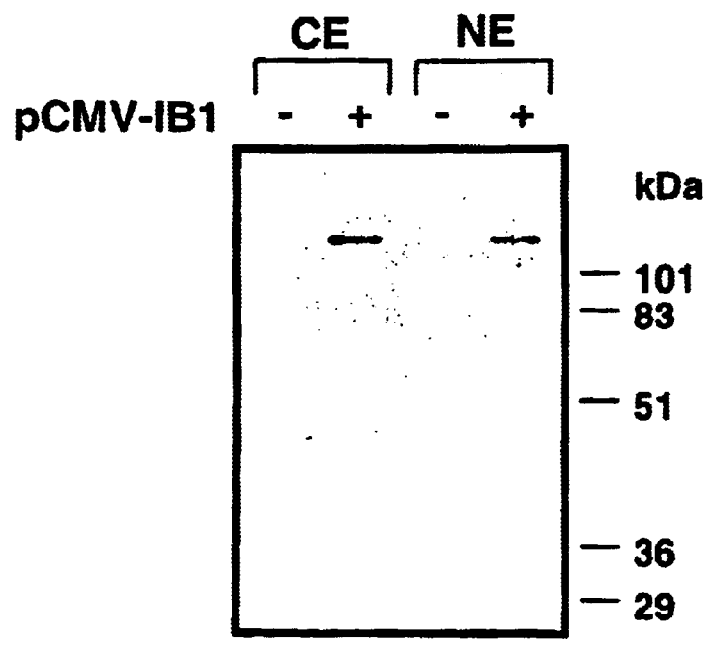
Figure 3E:
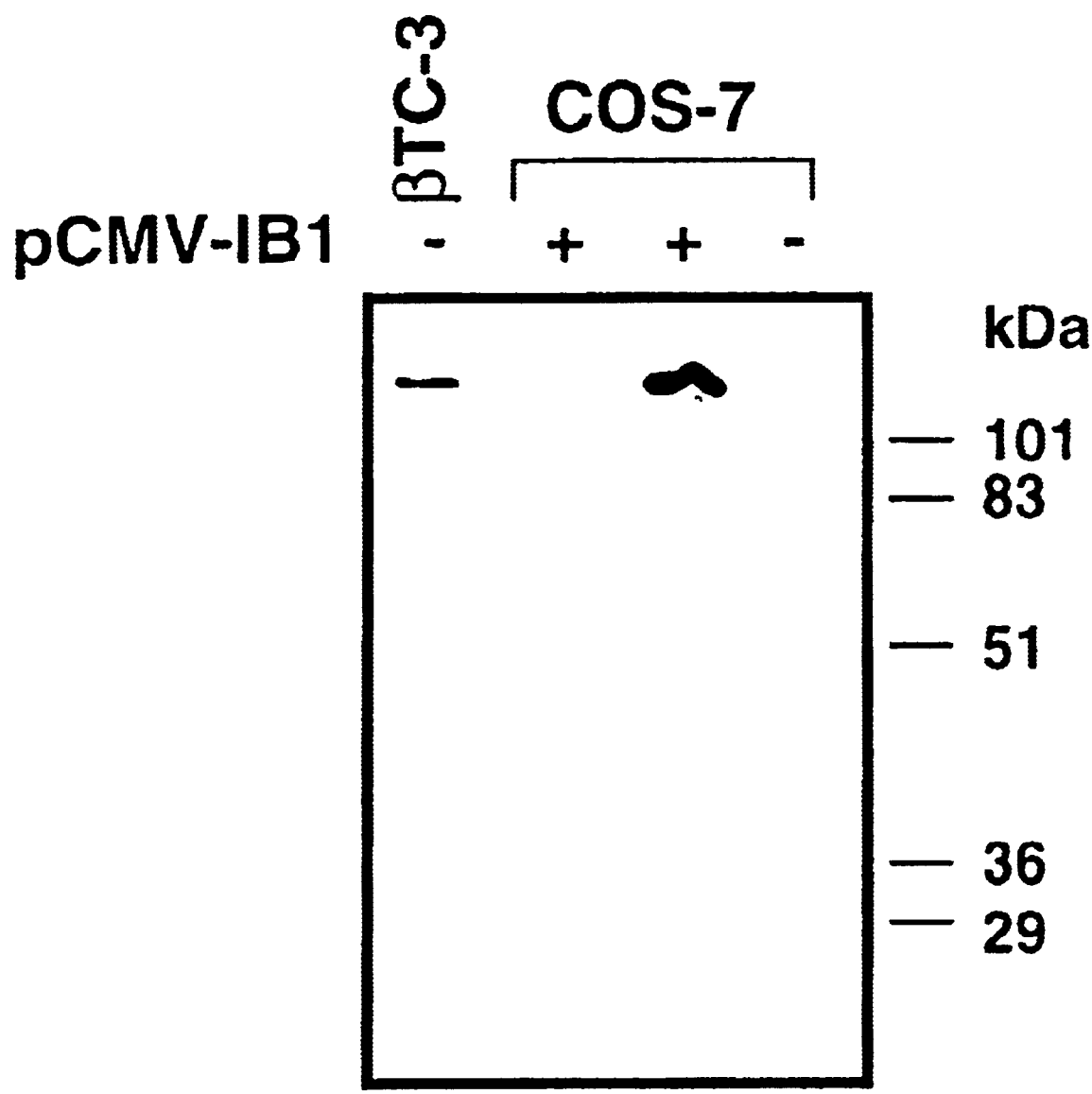

Antibodies were raised against the bacterially-produced N-terminal part of IB1 (aa 1–280 (SEQ ID NO: 2)). These polyclonal antibodies were affinity purified as described in Materials and Methods and used in Western blotting. As shown in FIG. 3A, these antibodies detect a 120 kDa protein in βTC3 nuclear extracts which comigrate with the product obtained by in vitro translating the IB1 cDNA in presence of $^{35}$S methionine (FIG. 3B). Similarly, the IB1 protein could be detected in both the nuclear and cytoplasmic extracts obtained from COS-7 cells transiently transfected with the CMV driven IB1 cDNA, which suggests that IB1 is actively translocated in the nucleus (FIGS. 3C and D). A survey of several rat tissues confirmed that the IB1 transcripts expressed in brain are translated into immunodetectable protein once analyzed by Western blotting (FIG. 3E).

EXAMPLE 4

Immunostaining Analysis of IB1 Expression

To gain further information regarding the tissue and cellular localization of IB1 within the pancreas, immuno-histochemistry studies were performed on mouse islets and βTC3 cells. Using the affinity-purified antibodies directed against IB1, this factor was detected in the pancreatic islet, with a staining which differs from the one obtained with the anti-GLUT2 or the anti-insulin antibodies. The immunostaining reaction is negative in βTC3 cells incubated with preimmune serum whereas the signal was positive in the nuclei and the cytoplasm of the same cells exposed to the anti-IB1 serum. In order to confirm the specificity of the anti-IB1 antibodies in immunocytochemistry, a construct was generated which includes a FLAG epitope N-terminal to the IB1 protein expressed under the control of a CMV promoter. This construct was transiently transfected into COS-7 cells, immunodetected with an anti-FLAG antibody subsequently visualized by FITC-staining or with the anti- IB1 antibody subsequently visualized with an anti-rabbit Texas red-labeled antibody. The IB1 protein was detected in transfected COS-7 cells with both the anti-FLAG and the anti-IB1 antibodies confirming that the protein is, at least in part, correctly translocated to the nuclei of COS-7 cells and that the anti-IB1 antibody is specific to IB1.

EXAMPLE 5

The IB1 Protein Binds Specifically to GTII and to the Insulin Enhancer Sequence RIPE3

Figure 4A:
FIG. 4
Similar DNA-binding Activity Between the GTII cis Element of the GLUT2 Promoter and the Insulin Enhancer Sequence RIPE3.

By analogy with PDX-1 which was shown to be an homeodomain transcription factor and which is expressed specifically in the pancreatic islets and is able to control several genes expressed only in these cells through homologous DNA sequences (22,24,28,53,54), we hypothesized that IB1 could similarly control several genes within the β-cells. The GTII cis sequence used for the expression cloning of IB1 shares some nucleic acid sequences identity with an important enhancer sequence of the insulin promoter termed RIPE3 for rat insulin promoter element 3. This RIPE3 element was previously shown to participate in the β-cell specific control of the insulin gene (17,20). As depicted in FIG. 4A, some conserved nucleic acid sequences are present between GTII and RIPE3 (SEQ ID NOS: 54–55).

Figure 4B:
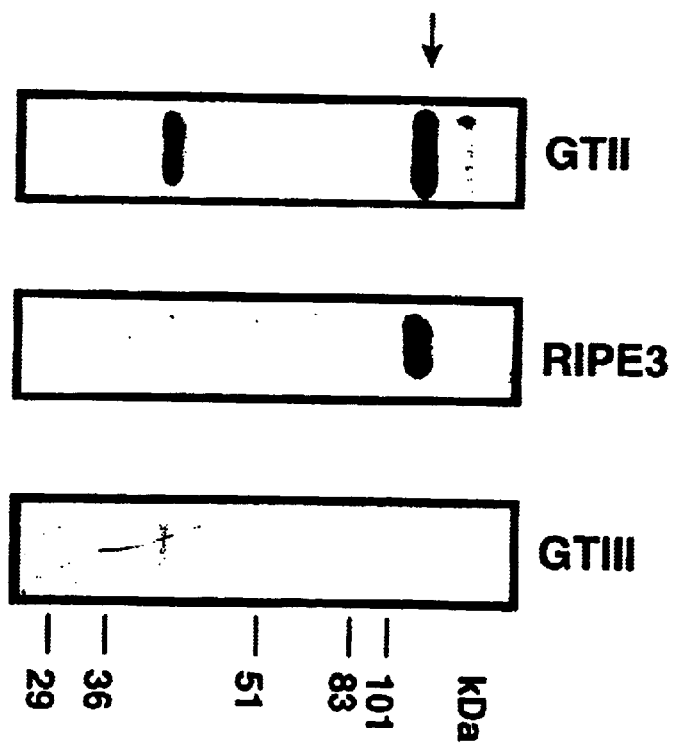
Figure 4C:
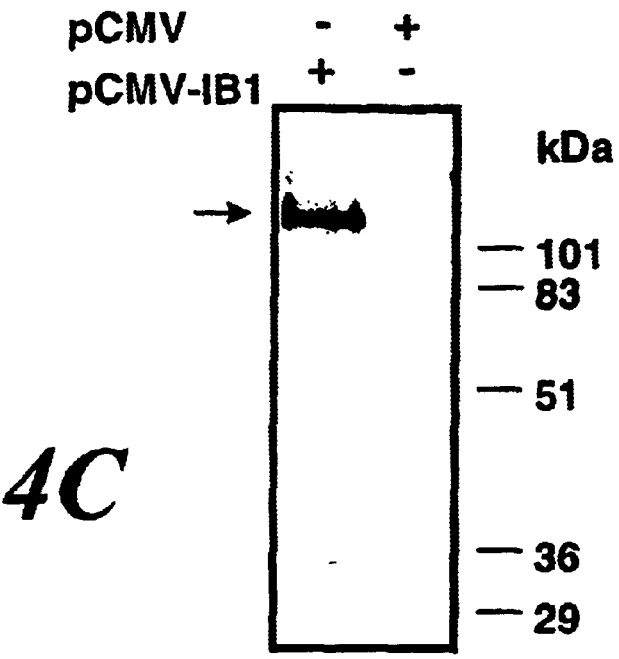

By SouthWestern analysis of INS-1 nuclear extracts, both the GTII and RIPE3 probes detected a 120 kDa protein which is similar in size to the product obtained by in vitro translating the IB1 cDNA in presence of $^{35}S$ methionine and to the protein detected using anti-IB1 antibodies (FIG. 4B). Furthermore, the IB1 cDNA was cloned 3' to a CMV promoter and transiently transfected into COS-7, a cell line lacking endogenous IB1. Crude cellular extracts were subsequently analyzed by the SouthWestern technique using the GTII probe. Only IB1-transfected COS-7 cells express the expected 120 kDa GTII-binding protein (FIG. 4C). The IB1 cDNA is therefore translated into a 120 kDa product which is able to bind the GTII probe in a manner similar to the endogenous binding activity observed in INS-1 or βTC3 nuclear extracts.

Figure 4D:
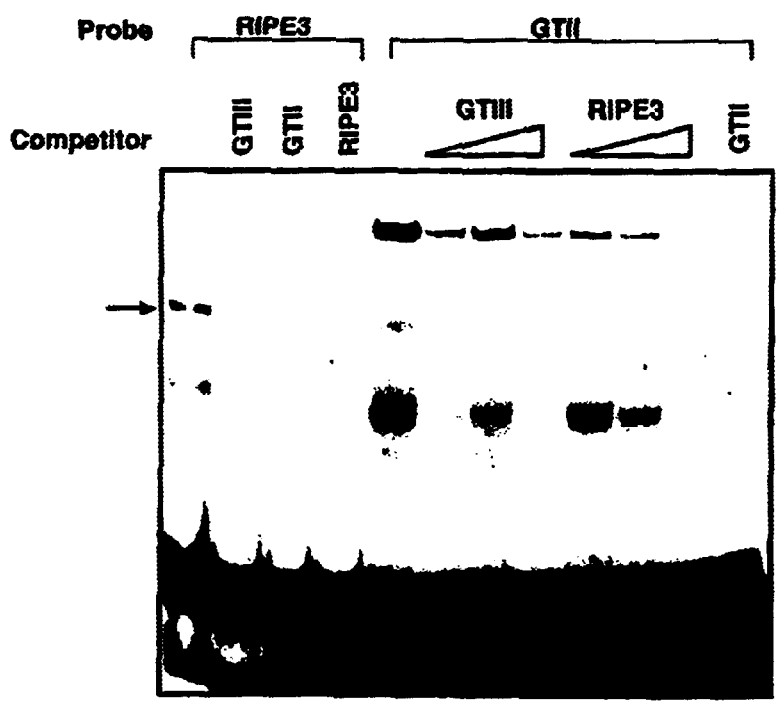

Gel retardation analysis were also conducted using either the GTII or the RIPE3 elements as probe with βTC3 nuclear extracts. A shown in FIG. 4D, the GTII-binding activity is competed with an excess of cold RIPE3 and inversely, the RIPE3 binding activity is competed with an excess of cold GTII nucleotides. Therefore, similar DNA-binding activities present in insulin secreting cells interact with both the GTII and the RIPE3 regulatory sequences. This suggests that IB1, which binds GTII and RIPE3, may regulates expression of the GLUT2 and insulin genes. Constructs were then generated that include only the amino (amino acids 1–280 (SEQ ID NO: 2)) or the COOH-terminal part (280–714 (SEQ ID NO: 2)) of the protein, and bacterially produced recombinant IB1 proteins were obtained from these plasmids. The 280–714aa protein, but not the 1–280aa protein, was able to bind the GTII cis sequence when tested by SouthWestern analysis implying that the carboxy end of the protein contains the DNA-binding domain of IB1.

EXAMPLE 6

Transcriptional Activation by IB1

Figure 5A:
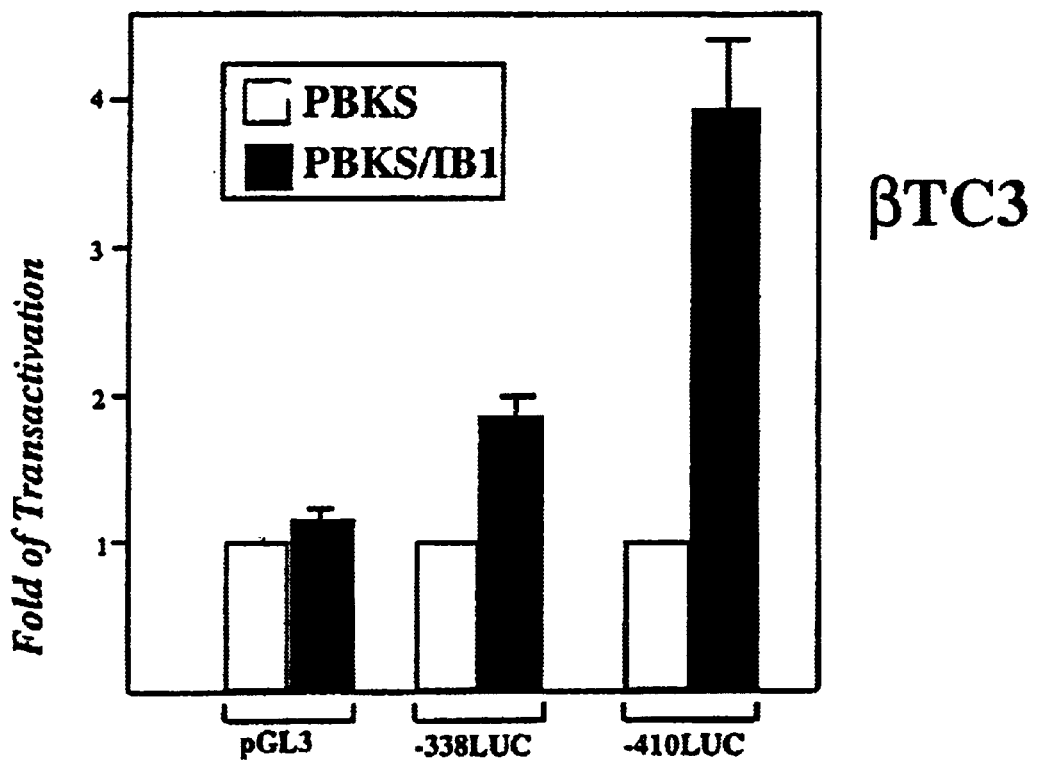
Figure 5A:
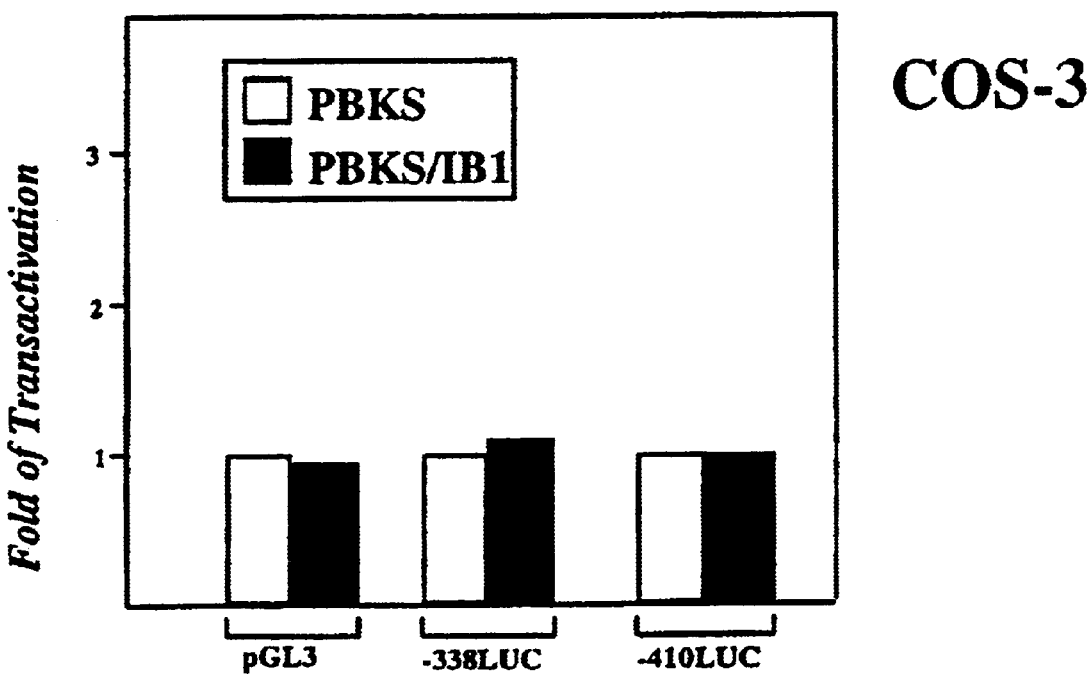
Figure 5B:
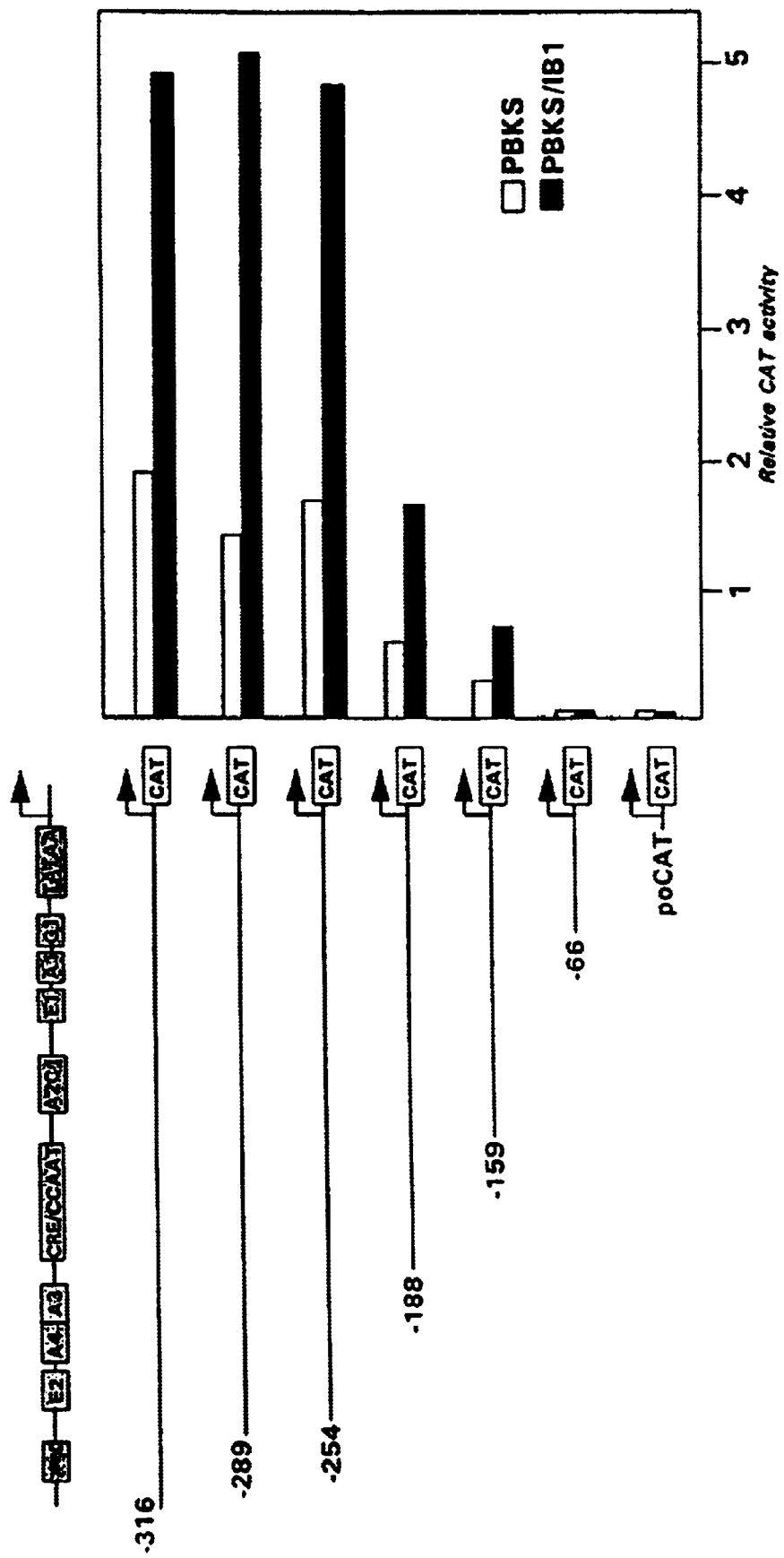
Figure 5C:
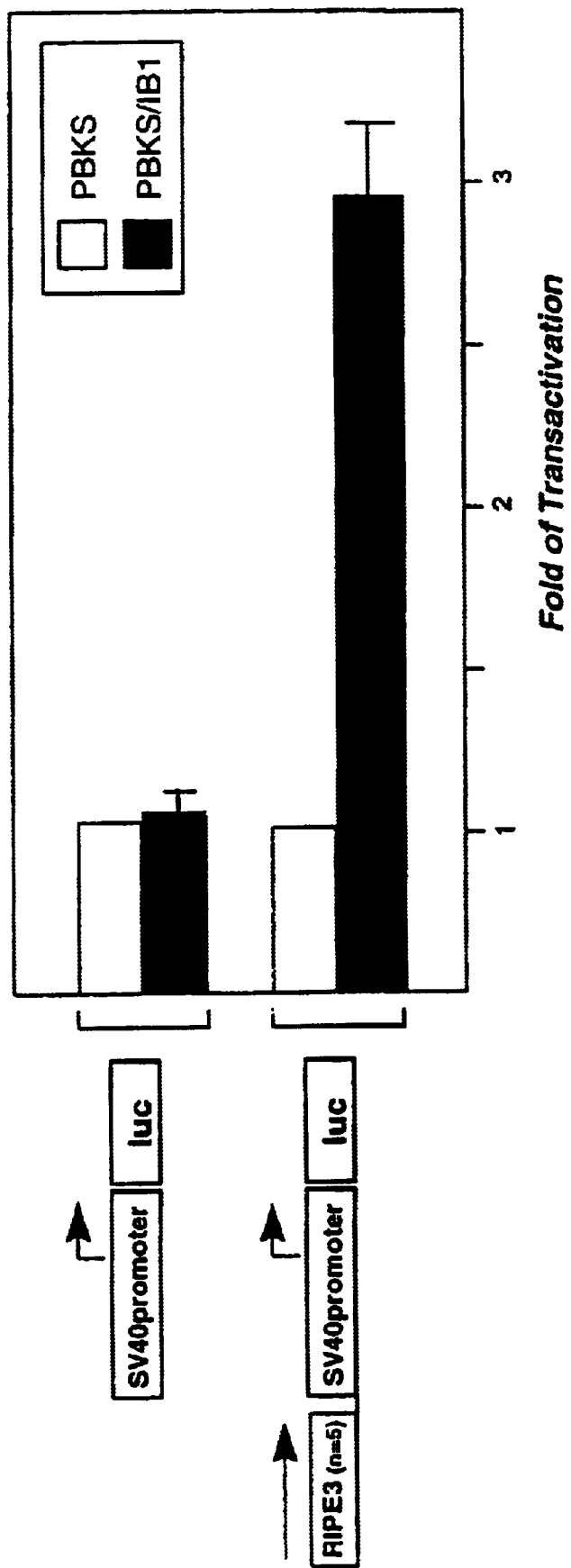

Transcriptional activation by IB1 was assayed by cotransfection experiments in the insulin-secreting cell line βTC3 and in a glucagon producing cell line (InR1-G9) as well as the non pancreatic-derived cell line COS-7 cells with an IB1 expression vector (PBK/IB1) and several reporter contructs (FIG. 5A). The wild-type insulin I promoter region (−410 bp) and the proximal region of the GLUT2 promoter (−338 bp) were linked to a luciferase reporter gene and transiently transfected in these cell lines. Overexpression of IB1 transactivated the GLUT2 promoter 1.7 fold whereas the insulin gene was induced 3.8 fold when compared to a co-transfection with the expression vector lacking the IB1 cDNA (PBKS). This effect was restricted to the insulin-secreting cells and clearly absent with the promoterless reporter construct (pGL3). The restricted action of IB1 in β-cells suggest that IB1 functions only in the presence of other regulators present in pancreatic β-cells, possibly others yet-to-be-identified β-cell specific transcription factors. Several 5' deletion constructs of the rat insulin I promoter were then similarly transfected into βTC3 cells in the presence or the absence of the expression vector encoding IB1. This latter transactivated several exonuclease III-deleted regions of the insulin promoter, although this effect was lower once constructs 3' to the −159 bp were used (FIG. 5B). This indicates that the RIPE3 sequence located 5' to the −159 bp of the promoter could be an important regulatory element through which IB1 transactivates the insulin gene (13). For the next series of experiments we addressed the question whether IB1 could mediate its stimulatory effect through the RIPE3 enhancer sequence of the rat insulin II gene. This enhancer sequence has been extensively studied by several investigators. Two separate subelements of RIPE3, RIPE3a and RIPE3b, function cooperatively to generate maximal activity of this tissue-specific enhancer (17). Each subelement binds ubiquitously expressed or β-cell specific trans-acting factors such as BETA1, BETA2 and E47 (26,27,34, 37). Most interestingly, the BETA2/E47 heterodimer has been shown to be a potent transactivator of the RIPE3 elements, effect mediated through the E box located within the RIPE3a subelement (27). However, this stimulatory effect necessitate the RIPE3b adjacent subelement where putative β-cell specific trans-acting factor(s) may bind to optimise the stimulatory effect the HLH factors. To investigate if IB1 is one of the possible partners of the RIPE3 binding factors, 5 copies of the RIPE3 element were cloned 5' to a minimal heterologous promoter (SV40) linked to a luciferase gene. This construct or its parent vector (SV40 luciferase) were transfected into βTC3 cells with or without the expression vector encoding IB1. As shown in FIG. 5C, IB1 transactivated the RIPE3 construct 5-fold and this effect was not present in the glucagon producing cell line InR1-G9 (data not shown). Taken together, these results confirm that IB1 is a component of the RIPE3 binding factors as evaluated by Southwestern analyses and cross-competition assays with the RIPE3 and GTII elements (FIG. 5) and as evaluated by the functional data obtained with the RIPE3 construct (FIG. 5).

EXAMPLE 7

Sequence of Human IB1 cDNA and Comparison with Rat IB1 cDNA

Screening of a human insulinoma cDNA library using as a probe the rat IB1 cDNA yielded the 3' end of sequence of human IB1 cDNA. This sequence started at position corresponding to nucleotide 1324 of rat IB1 cDNA. Part of the 5' end of human IB1 cDNA was obtained by a RACE and RT-PCR performed on total RNA isolated from a human glucagonoma, as described in the Methods, whereas the remaining 5' end sequence was deduced by comparison of genomic sequences with the rat IB1 cDNA. Human IB1 cDNA comprises a total of 2136 nucleotides (FIG. 1 (SEQ ID NO: 3)). A 141-bp sequence corresponding to a 47 amino-acid motif which distinguishes IB1 from JIP-1 was present in the cDNA clone and is given in bold. Comparison at the amino acid level of the deduced human (upper lane) and rat (lower lane) IB1 sequences is given in Table 2 (SEQ ID NOS: 32–53). Overall, there is a 95% similarity and 94% identity between rat and human IB1. Rat IB1 cDNA comprised two ATG codons separated by an 18-bp sequence, so that the initiating methionine was ambiguous. Human IB1 cDNA only contains one unambiguous ATG codon which is flanked in 3' by a large open reading frame (ORF) homologous to nucleotides 21 to 122 of the rat IB1 cDNA. As compared to rat IB1, human IB1 contains five inserted residues (in positions 7, 115, 142 and 267), whereas one amino acid is lacking between residues 79 and 80 so that, altogether, human IB1 contains four more residues than rat IB1. It is worth noting the fact that apparently functionally important sequences, as deduced from computer analysis of rat IB1 sequence are highly conserved between rat and human IB1. Finally, 46 amino acids out of the 47-amino acid residues fragments which distinguishes IB1 from JIP-1 were identical between rat and human IB1. Taken together, these data show that the IB1 gene is expressed in human insulinoma. In addition, the high degree of identity at the amino-acid level between rat and human IB1 suggests that IB1 may play an important biological role.

EXAMPLE 8

Southern Blot Analysis of the Human IB1 Gene

Figure 7:
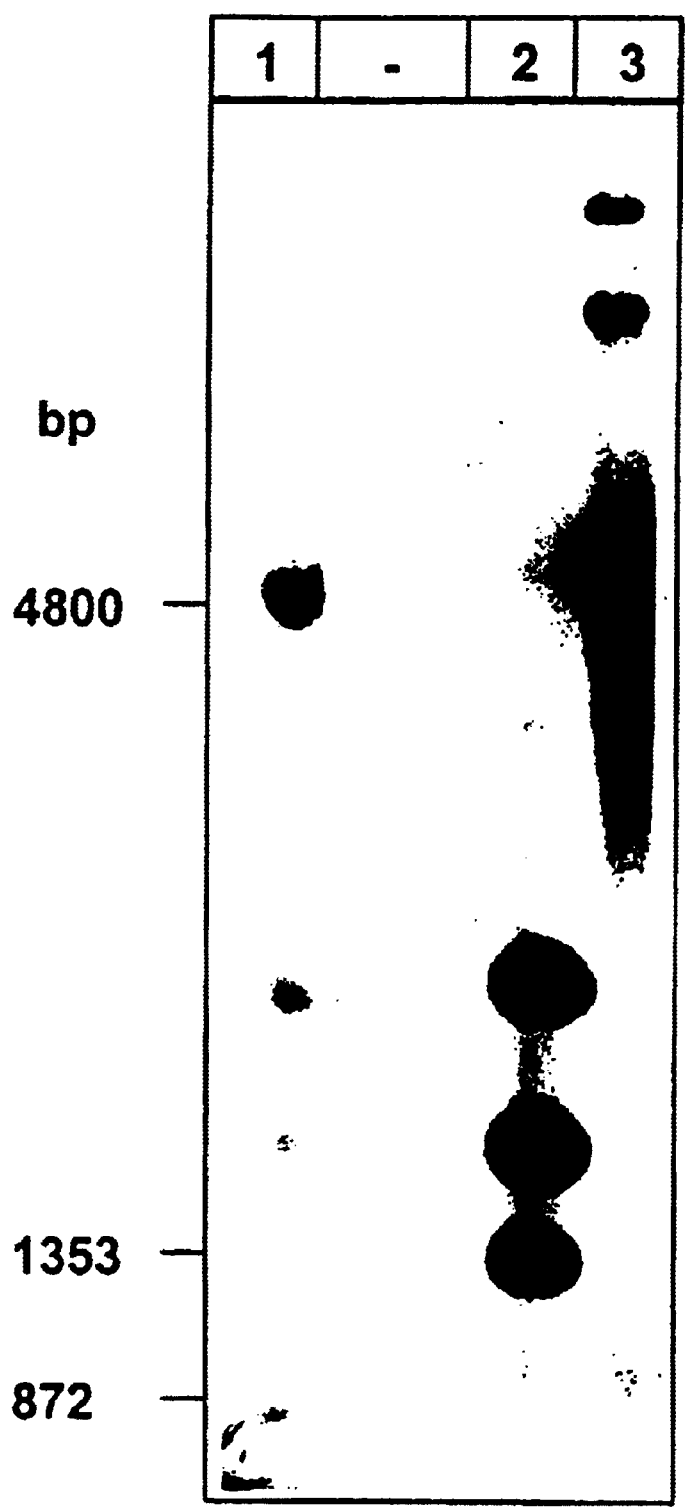

A BAC library of human genomic DNA was screened using as a probe a 1.8 kb fragment corresponding to the 3' end of human IB1 cDNA. Six strongly positive clones were selected. Southern blot analysis was performed on BamHI/BglII digested BAC clones using this same probe. Two different patterns were observed. One clone, BAC-A, displayed four bands of apparent size [18] 2.0, ~1.6, ~1.3 and ~0.8 kb (FIG. 7, lane 2), respectively. In contrast, BAC-B (lane 3) showed the presence of a strong 4.8 kb band and two additional larger faint bands. The prominent 4.8 kb band visible in BAC-B was also present in the remaining four selected BAC clones (data not shown). The banding patterns obtained with BAC-A and BAC-B clones were compared to the one observed when analyzing BamHI/BglII digested human genomic DNA (lane 1). A total of seven bands were visible in human genomic DNA. All the bands identified in human genomic DNA were accounted for by the bands visible when analyzing BAC-A and BAC-B. In particular, the prominent 4.8 kb band and two larger faint bands were similar in size to the bands detected in BAC-B (lane 3), whereas the four smaller faint bands visible in human genomic DNA were comparable in size to the four bands visible in BAC-A (lane 2). The filter was stripped and the a 955-bp fragment corresponding to the 5' end of rat Ibl cDNA was used as a probe. A total of three bands of apparent sizes 6.0, 1.5 and 1.4 kb, respectively, were visible for BAC-A, whereas the strong 4.8 kb band previously identified when using the 3' probe was the only band visible for BAC-B (data not shown). Taken together, these data indicate that 1) BAC-A is likely to include the multi-exonic IB1 gene: 2) the size of the IB1 gene approximates 14 kb; 3) BAC-B contains an homologue of the IB1 gene or an IB1 pseudogene; 4) the presence of additional IB1 homologues or pseudogenes in the human genome is unlikely; in particular, our data do not provide any evidence for the presence in human genome of a gene other than the IB1 gene that would encode JIP-1.

EXAMPLE 9

Structure of the Human IB1 Gene

Figure 6:
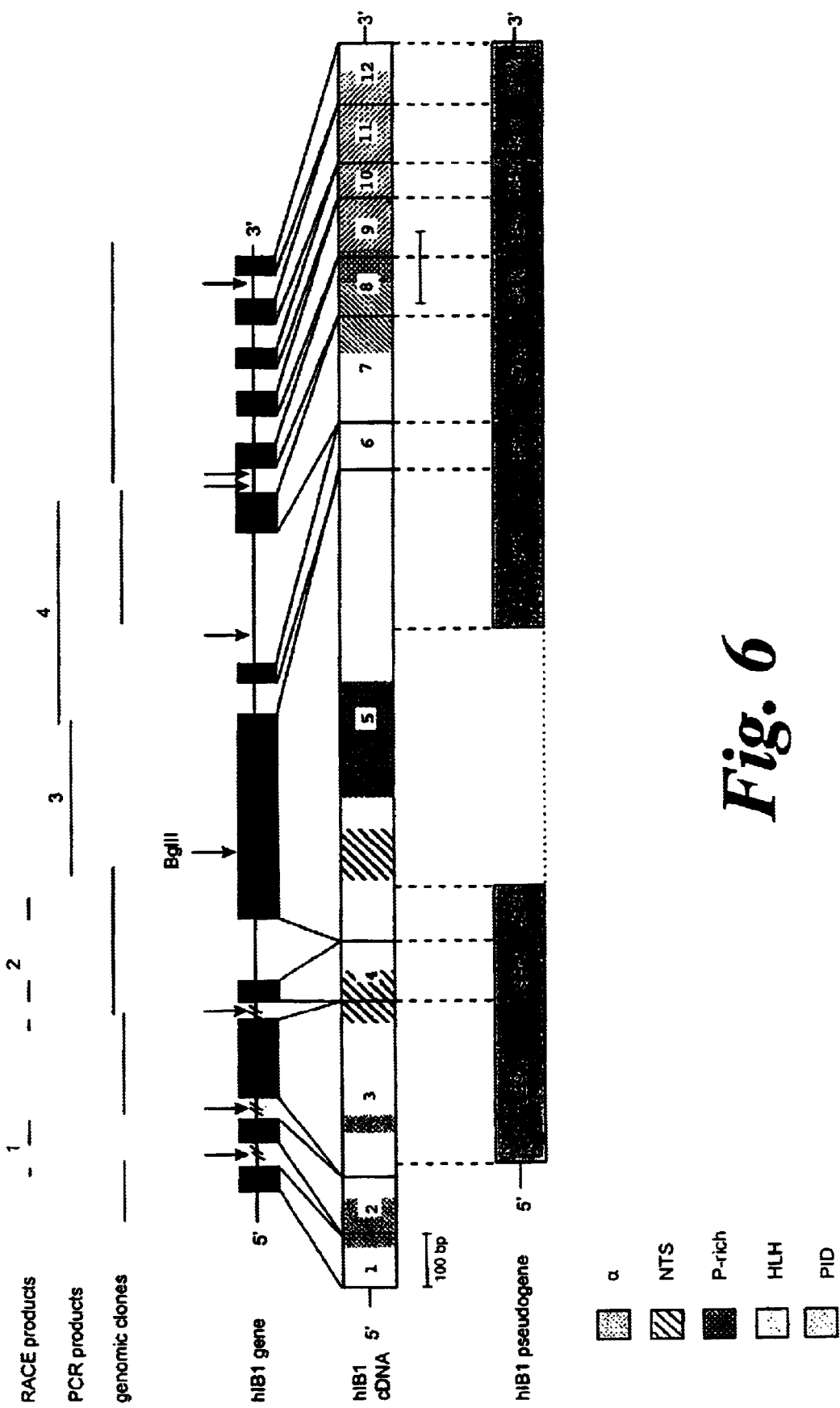

Fragments generated by digestion of BAC-A with BamHI/BglII were cloned into a Bluescript phagemid vector and these clones were screened using two non-overlapping probes, a 955-bp fragment corresponding to the 5' end of rat IB1 cDNA or the 1.8-kb fragment corresponding to the 3' end of human IB1 cDNA. Positive clones were subjected to sequence analysis. This analysis, completed by a PCR-based approach for regions of the gene that were not present in the Bluescript subclones, revealed the sequence of the coding region of the IB gene and its structural organization (FIG. 6). The IB1 gene contains 12 exons and 11 introns. The size of the exons ranges from 71 (exon 10) to 813 (exon 5) nucleotides. A complete identity was observed between the available nucleic acid sequence of human IB1 cDNA (obtained as described above) and sequences of the coding regions of the IB1 gene. The position of the intron-exon junctions are indicated in FIG. 6 by a bullet. It is worth noting that the sequence encoding the 47 amino-acid motif which distinguishes IB1 from JIP-1 (which is indicated by a bar in FIG. 6) spans over two adjacent exons (exons 8 and 9). Sequence analysis of the intron-exons junctions (Table 3) revealed that all splice sites obeyed to the GT-AG paradigm. These data indicate that 1) IB1 is encoded by a multi-exonic gene contained within the BAC-A clone and 2) the JIP-1 isoform may be an alternative spliced variant of the IB1 gene; however, the intron-exon structure of the IB1 gene renders this possibility unlikely.

EXAMPLE 10

Sequence of the 4.8 kb Fragment of BAC-B Clone

This analysis disclosed a high degree of homology between this genomic fragment and human IB1 cDNA (SEQ ID NO: 3). In particular, a 737-bp ORF which was 97% homologous to nucleotides 1297 to 2133 of human IB1 cDNA was identified. An additional 657 bp ORF was identified which included a 488-bp sequence homologous to nucleotides 228 to 716 of human IB1 cDNA. However, numerous stop codons were identified between the ORF's. As a first step in determining whether these ORFs were expressed in eukaryotic cells, the Bluescript vector containing the 4.8 kb fragment was transfected into COS-1 cells. No immunoreactive material was identified in transfected COS-1 cells (data not shown), a finding consistent with the ORF being not expressed in COS-1 cells. The same result was obtained when the 4.8 kb fragment was excised and inserted within a CMV-driven plasmid transfected in the same way (data not shown). Altogether, these data strongly suggest that this IB1 cDNA-related genomic sequence corresponds to an IB1 pseudogene. The nature of the two larger bands identified in Southern blot analysis of human genomic DNA and BAC-B was not determined. The fact that these two bands were only detected when using the 1.8 kb probe from the 3' end of the IB1 cDNA suggests that they correspond to sequences which share some homology with the 3' end of human IB1 cDNA.

EXAMPLE 11

Chromosomal Localization of the IB1 Gene and the IB1 Pseudogene

Fluorescent in-situ hybridization (FISH) was performed to map the IB1 gene and the IB1 pseudogene. Fragments generated by BamHI/BglII digestion of BAC-A and BAC-B were labelled and used as probes BAC-A (corresponding to the IB1 gene) and BAC-B (corresponding to the IB1 pseudogene) probes. The IB1 gene and the IB1 pseudogene are located on separate chromosomes. The IB1 gene is positioned close to the centromere on the short arm of chromosome 11, whereas the IB1 pseudogene maps to the long arm of chromosome 17. The chromosomal localizations were confirmed when using centromere-specific markers for chromosome 11 and chromosome 17.

Next, fine mapping of the IB1 gene and IB1 pseudogene was performed using radiation hybrid mapping. This analysis was initially carried out using one pair of oligonucleotides designed using the sequence of human IB1 cDNA. These primers amplified a ~260 bp fragment in the radiation hybrid mapping system corresponding to sequences 1346 to 1602 of human cDNA (SEQ ID NOS: 28 and 29). This fragment corresponds to sequences from the IB1 pseudogene, as amplification of sequences from the IB1 gene would have resulted in a larger product spanning over three exons (exons 5 to 7) and two introns. Analysis of the Stanford G3 and Genebridge G4 radiation hybrid panels confirmed the observation done by FISH that the IB1 pseudogene is localized on the long arm of chromosome 17, which corresponds to 17q21.32–33 on the LDB (59) cytogenic map. The reason why the location of the IB1 gene was not detected using this pair of oligonucleotides is not known. To locate the position of the IB1 gene, an additional pair of primers were used. One primer was designed based on the sequence of IB1 cDNA and the other one on intronic sequences within the IB1 gene. Results from the two radiation hybrid panels placed the IB1 gene on the short arm of chromosome 11, thus confirming the previous observation done by FISH, which corresponds to 11p11.12 on the. LDB (59) cytogenic map. The IB1 gene was localized adjacent to markers D11S1344 and D11S3979.

EXAMPLE 12

Expression of IB1 in Human Tissues

Expression of IB1 in human tissues was examined using Northern blot analysis of poly(a)+RNA isolated from a panel of different human tissues and the 1.8 kb fragment corresponding to the 3' end of human IB1 cDNA as a probe. IB1 was expressed as a single transcript in the pancreas, the heart, brain and testis. The tissue distribution of IB1 in human tissues closely resembles the distribution previously reported in rat tissues.

Discussion

These results show the isolation and characterization of a new transactivator of the GLUT2 and the insulin genes. This factor, termed IB1, is highly expressed in pancreatic β-cells and was isolated by its ability to bind to a cis regulatory element of the GLUT2 promoter. We also demonstrate that IB1 is able to bind to a homologous regulatory element of the insulin gene, RIPE3. This enhancer sequence contains two separate sub-elements, RIPE3a and RIPE3b, which function cooperatively to generate maximal activity of this tissue-specific enhancer (Hwung et al., 1990). RIPE3 binds ubiquitously expressed and β-cell specific trans-acting factors such as BETA1, BETA2 and E47 (Shieh and Tsai, 1991; Murre et al., 1989; Peyton et al., 1994; Naya et al., 1995). The BETA2/E47 heterodimer has been shown to be a potent transactivator of the RIPE3 element, an effect mediated through the E box located within the RIPE3a subelement (Naya et al., 1995). This stimulatory effect necessitates the RIPE3b adjacent sub-element where yet-to-be-identified β-cell specific trans-acting factor(s) bind. As IB1 is able to bind RIPE3 in vitro and as this factor is able to transactivate RIPE3 mediated reporter gene expression in β cells, we propose that IB1 is one of the important partners of the RIPE3-binding proteins. The competition assays using as probe either GTII or RIPE3 demonstrated that the GTII-binding proteins have a high affinity for the GTII cis element, however they are competed with an excess of cold RIPE3 oligonucleotides. Conversely, the RIPE3-binding proteins detected by mobility shift (EMSA) assay with the RIPE3 probe are competed with an excess of cold GTII. However, we were unable to supershift, using anti-IB1 antibodies, the GTII- or RIPE3-binding activities detected by EMSA. This observation suggests that the antibodies raised against IB1 are unable to detect IB1 in non-denaturating conditions where the epitopes may be masked by other binding proteins. Furthermore, IB1 binding activity necessitates post-translational modifications. Dephosphorylation of βTC3 nuclear extracts abolishes the binding of IB1 to GTII or RIPE3 when assessed by SouthWestern analysis.

Functionally, IB1 is a transactivator of the GLUT2 promoter (170% increase over basal) but a potent inducer of insulin gene transcription (380% increase over basal) This effect may reflect the higher binding affinity of IB1 to GTII rather than RIPE3 (see FIG. 5). As IB1 functions only in β-cell lines where endogenous IB1 is present, one may speculate that the GLUT2 reporter construct cannot be stimulated with the expression vector encoding IB1 since the high affinity GTII cis elements are already occupied by endogenous IB1. More recently, Stellrecht and co-authors have elegantly demonstrated that multiple copies of the RIPE3 sequence are able to drive reporter gene expression in a restricted manner in pancreatic β-cells and in the brain of transgenic mice (Stellrecht et al., 1997). As IB1 expression is the highest in the brain and in β-cells and as this factor transactivates the insulin gene through RIPE3, these observations show that IB1 participates in the tissue-specific control of the insulin gene.

As observed with BETA2, IB1 is expressed in a highly restricted manner (Naya et al., 1995). BETA2 is found in α- and β-cells and in the brain whereas IB1 expression is present only in β-cells, in the brain and to a lower extent in the heart and the kidney. Interestingly, GLUT2 is expressed in β-cells, in the gut, the kidney, the liver and in a subset of neurons (Thorens et al., 1988; Leloup et al., 1994; Orci et al., 1989) and the gene encoding GLUT2 is abnormally regulated only in the endocrine pancreas when diabetes is present (Johnson et al., 1990; Ohneda et al., 1993; Orci et al., 1990b; Orci et al., 1990a; Thorens et al., 1992; Thorens et al., 1990; Unger, 1991). As IB1 is a transactivator of the insulin and the GLUT2 genes and as IB1 expression is mainly restricted to β-cells and is not expressed in liver, abnormal expression or function of IB1 could be responsible for the diabetic- and β-cell specific dysregulation of GLUT2. Phosphorylation is necessary, as a post translational modification of IB1, to allow the binding of IB1 to its recognition site. Some β-cell functions, including phosphorylating activities, are altered during diabetes and therefore could induce a loss of IB1 binding activity.

The recent identification of mutations present in the transcription factors HNF-1α and HNF-4α, factors which are weak transactivators of the insulin gene and which are also expressed in β-cells, is of interest since they are responsible for the onset of two forms of diabetes, MODY3 and MODY1, respectively (Yamagata et al., 1996b; Yamagata et al., 1996a).

An intriguing observation on IB1 is its subcellular localization as it is located in both the cytoplasmic and nuclear compartments. IB1 contains a putative nuclear translocation signal (Dingwall and Laskey, 1991) and several lines of evidence suggest that indeed, IB1 is a nuclear protein. First, IB1 is a DNA-binding protein as this factor has been cloned based on its ability to bind to the GTII cis element. Second, the SouthWestern experiments could detect IB1 in nuclear extracts of transfected COS cells with the expression vector encoding IB1. Third, immunodetectable nuclear staining is present by histochemistry in pancreatic islets as well as in βTC3 cells and Western blot analysis of these cells could also detect IB1 in the cytoplasm and the nucleus. Finally, IB1 is clearly a transactivator of the GLUT2 and the insulin promoter linked to a reporter gene which implies that this factor functions as a transcription factor. The mechanisms responsible for the active translocation of IB1 in the nucleus are not yet understood but could be of importance as IB1 transacting functions may simply depend on the control of translocation. Several other similar observations are described where a DNA binding protein is sequestrated in the cytoplasm and translocated into the nucleus once proper stimulus is present. NFκB is sequestered in the cytoplasm by an interaction with Iκ-B (Beg et al., 1992). Once phosphorylated, the complex is dissociated and NFκB is translocated in the nucleus and acts as a transactivator (Ghosh and Baltimore, 1990). BZP has also recently been described as a zinc finger DNA-binding protein expressed in β-cells (Franklin et al., 1994). Serum deprivation caused BZP to remain cytoplasmic, whereas the adjunction of serum induces BZP translocation allowing its function as an inhibitor of gene transcription. The mechanism of sequestration of the cAMP responsive element binding protein (CREB) in the cytoplasm of germinal cells has also been described and involves the formation of a truncated CREB protein, lacking the nuclear translocation signal, by the use of an alternatively spliced exon (Waeber and Habener, 1991; Waeber et al., 1991). The mechanisms which trigger the translocation of IB1 into the nucleus might involve glucose, serum or any cellular component such as cAMP or ATP. This issue is important to resolve as the IB1 transactivating function may be dependent upon proper regulated translocation of the protein into the nucleus.

The above results demonstrate that IB1 is a novel DNA-binding protein which is expressed in a highly restricted manner in β-cells and in the brain, which functions, together with other unidentified β-cell specific factors, as a transactivator of the GLUT2 and the insulin gene through homologous DNA sequences. Due to the restricted expression of IB1, we propose that IB1 is an important factor which confers β-cell-specificity to the insulin and GLUT2 genes.

IB1/JIP-1 is a key regulator of insulin secretion in the rat and an inhibitor of the JNK-activation pathway in the mouse. We demonstrate in this study that IB1/JIP-1 is also present in humans. Indeed, human IB1 is highly similar to mouse and rat IB1. Furthermore, IB1 is expressed in humans in the same tissues as was previously reported for rodents. The IB1 gene maps to the long arm of chromosome 11 at position 11p11.12 and is multi-exonic. There is also a pseudogene which shares a high degree of homology with IB1 cDNA and is located on chromosome 17. The results above also show that no other IB1-related homologue is present in human genome suggesting that, if JIP-1 is present in humans, it represents an IB1 isoform encoded by the IB1 gene.

Apart from its 47-residue insert, rat IB1 was previously shown to be 97% identical to mouse JIP-1. This striking inter-species identity is further reinforced by the present observations which show a 94% identity between human and rat or mouse IB1. The highly conserved structure of IB1 in mammals is evidence of the biological importance of IB1.

A sequence highly homologous to human IB1 cDNA was identified in human genome and was mapped to chromosome 17q21–22. Two observations support the conclusion that this sequence represents an IB1-pseudogene. First, despite the presence of two potential ORF's of 737 and 657 nucleotides, respectively, this sequence contained numerous stop codons. Second, the data shows that these potential ORF's are not translated into proteins once transfected into COS-1 cells, even when placed in front of a strong CMV promoter, suggesting the lack of correct initiating sites. In addition, it is of interest that this sequence contains the 141-bp sequence which is missing in JIP-1. It is thus very unlikely that JIP-1 is encoded by this sequence.

Our data show that, apart from the IB1 pseudogene, the presence of additional IB1-related gene in human genome is unlikely. In addition, we show that the 141-bp insert which distinguishes JIP-1 from IB1 spans over two exons. Taken together, these observations raise the questions as to whether JIP-1 is expressed in human tissues, and if so, what is the mechanism responsible for the generation of the transcript. The clone containing the 3' end of human IB1 cDNA was obtained from a human insulinoma cDNA library and contained the insert. RT-PCR amplifications of this library was performed using oligonucleotides flanking the insert, and only one amplicon containing the insert was obtained. While it might be the case that JIP-1 is expressed in other tissues or during embryonic development, JIP-1 does not appear to be a "simple" spliced variant of the IB1 gene. Potential splice donor/acceptor sites are present in exons 8 and 9. However, splicing at these sites would result in a frameshift and a truncated protein.

TABLE 1

Sequence of the Oligonucleotides Used to Characterize the Human IB1 Gene.

| Name of the Oligonucleotides | 5' to 3' Sequence |
| --- | --- |
| Oligo-dT-anchor primer | GACCACGCGTATCGATGTCGAC(T)$_{16}$V (SEQ ID NO: 18) |
| PCR anchor primer | GACCACGCGTATCGATGTCGAC (SEQ ID NO: 19) |
| RACE-1 | ATCAGGTCCATCTGCAGCATCTC (SEQ ID NO: 20) |
| RACE-2 | GCAAGGGCTGTCGGTGGAGGTGCCTCGA (SEQ ID NO: 21) |

TABLE 1-continued

Sequence of the Oligonucleotides Used to Characterize the Human IB1 Gene.

| Name of the Oligonucleotides | 5' to 3' Sequence |
|---|---|
| RACE-3 | TCCATCTGCATCTCGGCCT (SEQ ID NO: 22) |
| RACE-4 | GGACAGGGTGTCTTTGC (SEQ ID NO: 23) |
| RACE-5 | GGGCAGCTCATCGCTCAGGCA (SEQ ID NO: 24) |
| RACE-6 | GTTCATGCGGTGGTGTCTGCT (SEQ ID NO: 25) |
| IB1-787F | CATCGAGACCGAATCCAC (SEQ ID NO: 26) |
| IB1-1326R | GTTCAGGAATTTCTTGGAGAAATG (SEQ ID NO: 27) |
| IB1-1346F | TGATGAACCCGACGTCCAT (SEQ ID NO: 28) |
| IB1-1602R | ACCAGTGCGCATGTTGTAGG (SEQ ID NO: 29) |
| hIB1-intrF: | CCTGCCTTCATGACCTGCCTG (SEQ ID NO: 30) |
| hIB1-924R: | GGATTCGGTCTCGATGCGAG (SEQ ID NO: 31) |

TABLE 2

Exon-Intron Boundaries of the hIB1 Gene

| Exon | Size (bp) | Splice acceptor | Splice donor | Intron size (kb) |
|---|---|---|---|---|
| 1 | 101 | | CAATTTCAGgtgagagtccccggccgccgcg | >4.2 (SEQ ID NO:32) |
| 2 | 106 (SEQ ID NO:33) | TttggcttcctgtccccaccagGCTCACCCA | TCCTTACGGgtaagggcaagctcccaggagc | >2 (SEQ ID NO:34) |
| 3 | 315 (SEQ ID NO:35) | CgccctccgtgcgctgtgcagCCCCCGCGC | CGGTCTCAGgtgaggcgccaacgtgggggc | >0.8 (SEQ ID NO:36) |
| 4 | 82 (SEQ ID NO:37) | gagccttttgttccctgcacagGACACACTG | TGAAGACAGgtaagtcagggccctcttcctt | 0.31 (SEQ ID NO:38) |
| 5 | 83 (SEQ ID NO:39) | tcatgacctgcctgctctccagGGGAGCAGA | GCTCCTCCAgtgagtcagcaaggggaagcag | 0.18 (SEQ ID NO:40) |
| 6 | 76 (SEQ ID NO:41) | agccacaccacctcacctgcagGTGCTGAGT | CATATTCAGgtgagagccatgggctggctgg | 0.558 (SEQ ID NO:42) |
| 7 | 173 (SEQ ID NO:43) | cacctgtccttgctggggacagGTTTGTOCC | ACATGGCAGgtagtgttccctccctggcctg | -0.6 (SEQ ID NO:44) |
| 8 | 110 (SEQ ID NO:45) | tcaattcacgcttgctttccagCCCTGGCCA | ATGCAAAAGgtacctgagccctctcccttct | 0.148 (SEQ ID NO:46) |
| 9 | 117 (SEQ ID NO:47) | tggctccatttgtcacctgtagATTGCCACC | GAGGCCAAGgtgacttcttccaacccagccc | 0.137 (SEQ ID NO:48) |
| 10 | 71 (SEQ ID NO:49) | gcttcttttctccctcctgtagGGGAATAAA | GAACAACAAgtaagtgggggtgggatggcag | 0.109 (SEQ ID NO: 50) |
| 11 | 99 (SEQ ID NO:51) | acagacagacctgtccctgcagGTACTTTGG | GTCCGTGGGgtacgtgtacaccctgctgagc | -0.4 (SEQ ID NO: 52) |
| 12 | 70 (SEQ ID NO:53) | ctgtgtgtccctggcttctagGAGAGCATT | | |

References

The references mentioned herein are all incorporated by reference in their entirety.
1. Asfari et al, *Endocrinology* 130:167–178, 1992.
2. Beg et al, *Genes and Development* 6:1899–1913, 1992.
3. Bonny et al, *Mol Endo* 9:1413–1426, 1995.
4. Brasier et al, *Biotechniques* 7:1116–1121, 1989.
5. De Vos et al, *J Clin Invest* 96:2489–2495, 1995.
6. Deltour et al, *Proc Natl Acad Sci USA* 90:527–531, 1993.
7. Dent and Latchman, *Transcription Factors: A Practical Approach*, New York:Oxford University Press, 1993. pp. 1–26.
8. Dingwall and Laskey, *TIBS* 16:478–481, 1991.
9. Efrat et al, *Proc. Natl. Acad. Sci. USA* 85:9037–9041, 1988.
10. Ferber et al, *J. Biol. Chem.* 269:11523–11529, 1994.
11. Ferrer et al, *Diabetes* 44:1369–1374, 1995.
12. Franklin et al, *Mol and Cell Biology* 14:6773–6788, 1994.
13. German et al, *Diabetes* 44:1002–1004, 1995.
14. Ghosh and Baltimore, *Nature* 344:678–682, 1990.
15. Gotoh et al, *Transplantation* 43:725–730, 1987.
16. Hughes et al, *J. Biol. Chem.* 268:15205–15212, 1993.
17. Hwung et al, *Mol and Cell Biology* 10:1784–1788, 1990.
18. Johnson et al, *Science* 250:546–548, 1990.
19. Jonsson et al, *Nature* 371:606–609, 1994.
20. Karlsson et al, *Proc Natl Acad Sci USA* 84:8819–8823, 1987.
21. Leloup et al, *Brain Research* 638:221–226, 1994.
22. Leonard et al, *Mol Endo* 7:1275–1283, 1993.

23. McKnight and Kingsbury, *Science* 217:316–324, 1982.
24. Miller et al, *EMBO J* 13:1145–1156, 1994.
25. Mitchell and Tjian, *Science* 245:371–378, 1989.
26. Murre et al, *Cell* 58:537–544, 1989.
27. Naya et al, *Genes and Development* 9:1009–1019, 1995.
28. Ohlsson et al, *EMBO J* 12:4251–4259, 1993.
29. Ohneda et al, *Diabetes* 42:1065–1072, 1993.
30. Orci et al, *Proc. Natl. Acad. Sci. USA* 87:9953–9957, 1990.
31. Orci et al, *Science* 245:295–297, 1989.
32. Orci et al, *J Clin Invest* 86:1615–1622, 1990.
33. Pearse and Polak, *gut* 12:783–788, 1971.
34. Peyton et al, *J Biol Chem* 269:25936–25941, 1994.
35. Rencurel et al, *Biochem J* 314:903–909, 1996.
36. Rencurel et al, *Biochem J* 322:441–448, 1997.
37. Shieh et al, *J. Biol. Chem.* 266:16707–16714, 1991.
38. Singh et al, *Cell* 52:415–423, 1988.
39. Stoffers et al, *Nature Genetics* 15:106–110, 1997.
40. Takaki et al, In Vitro Cell Dev. Biol. 22:120–126, 1986.
41. Teitelman et al, *Development* 118:1031–1039, 1993.
42. Teitelman et al, *Dev. Biol.* 121:454–466, 1987.
43. Thorens et al, *Int. Review of Cytology* 137A:209–237, 1992.
44. Thorens et al, *Cell* 55:281–290, 1988.
45. Thorens et al, *Proc. Natl. Acad. Sci. USA* 87:6492–6496, 1990.
46. Thorens et al, *J Clin Invest* 90:77–85, 1992.
47. Unger, *Science* 251:1200–1205, 1991.
48. Valera et al, *J. Biol. Chem.* 269:28543–28546, 1994.
49. Waeber et al, *Mol Endo* 10:1431–1438, 1991.
50. Waeber et al, *Mol Endo* 10:1419–1430, 1991.
51. Waeber et al, *Mol Cell Endocrinol* 114:205–215, 1995.
52. Waeber et al, *J Biol Chem* 269:26912–26919, 1994.
53. Waeber et al, *Mol Endo* 10:1327–1334, 1996.
54. Watada et al, *Diabetes* 45:1478–1488, 1996.
55. Yamagata et al, *Nature* 384:458–460, 1996.
56. Yamagata et al, *Nature* 384:455–458, 1996.
57. Lunetta et al, *Am. J. Hum Genet* 59:717–725, 1996.
58. Stein et al, 1995 "RHMAPPER", unpublished software, Whitehead Institute/MIT Center for Human Genome Research. Available at http://www.genome.wi.mit.edu/ftp/pub/software/rhmapper/, and via anonymous ftp to ftp.genome.wi.mit.edu, directory/pub/software/rhmapper.
59. A Collins, J Teage, B J Keats, N E Morton (1996). Linkage map Integration. Genomics 36:157–162. Available at http://cedar.genetics.soton.ac.uk/public_html and via anonymous ftp to ftp.cedar.genetics.soton.ac.uk.

What is claimed is:

1. A substance which is an isolated polypeptide comprising a polypeptide comprising the amino acid sequence set out in FIG. 1F, SEQ ID NO: 4.

2. The substance of claim 1, wherein said substance displays an IB1 activity selected from the group consisting of GTII promoter binding activity, and RIPE3 promoter binding activity.

3. A substance which comprises a fragment of a polypeptide comprising the amino acid sequence set out in FIG. 1F, SEQ ID NO:4, wherein the fragment has the property of specifically binding to a GTII or RIPE3 promoter element having the nucleic acid sequence set out in SEQ ID NO: 55 and 56 so that the binding causes transcriptional activation of a gene under the control of a promoter including said promoter element.

4. A substance which comprises a fragment of a polypeptide comprising the amino acid sequence in FIG. 1F, SEQ ID NO: 4, the fragment consisting of a domain from amino acids 563–609 of the sequence shown in FIG. 1F.

5. An isolated nucleic acid molecule comprising the nucleic acid sequence set out in FIG. 1E, SEQ ID NO: 3.

6. An isolated nucleic acid molecule as claimed in claim 5, wherein said substance displays an IB1 activity selected from the group consisting of GTII promoter binding activity, and RIPE3 promoter binding activity.

7. An expression vector comprising a nucleic acid molecule of claim 5, operably linked to control sequences to direct its expression.

8. Host cells transformed with an expression vector of claim 1.

9. A method of producing IB1 polypeptide comprising culturing the host cells of claim 8 and isolating the polypeptide thus produced.

10. A composition comprising one or more substances of claim 2 in a carrier.

* * * * *

SEQUENCE LISTING

<160> NUMBER OF SEQ ID NOS: 55

<210> SEQ ID NO 1
<211> LENGTH: 2953
<212> TYPE: DNA
<213> ORGANISM: rattus

<400> SEQUENCE: 1

```
ccgccccagc tcagtccgaa ccccgcggcg gcggcggcct cctccacacg cctccacctc      60
cgccgccgcc gccgccgccg ccgcctcccg cgccgctctc cgcccggatg gccaggctga     120
gcccgggaat ggcggagcga gagagcggcc tgagcggggg tgccgcgtcc ccaccggccg     180
cttccccatt cctgggactg cacatcgcgt cgcctcccaa tttcaggctc acccatgata     240
tcagcctgga ggagtttgag gatgaagacc tttcggagat cactgatgag tgtggcatca     300
gcctgcagtg caaagacacc ttgtctctcc ggcccccgcg cgccgggcta ctgtctgcgg     360
gtagcagcgg tagcgcgggg agccggctgc aggcggagat gctgcagatg gacctgatcg     420
acgcggcaag tgacactccg ggcgccgagg acgacgaaga ggacgacgac gagctcgctg     480
cccaacggcc aggagtgggg ccttccaaag ccgagtctgg ccaggagccg gcgtctcgca     540
gccagggtca gggccagggc cccggcacag gctgcggaga cacctaccgg cccaagaggc     600
ctaccacgct caaccttttc ccgcaggtgc cgcggtctca ggacacgctg aataataact     660
ctttaggcaa aaagcacagt tggcaggacc gtgtgtctcg atcatcctcc cctctgaaga     720 cagggagca gacgcctcca catgaacata tctgcctgag tgatgagctg ccgccccagg     780
gcagtcctgt tcccacccag gatcgtggca cttccaccga cagcccttgt cgccgtactg     840
cagccaccca gatggcacct ccaagtggtc ccctgccac tgcacctggt ggccggggcc     900
actcccatcg agatcggtcc atatcagcag atgtgcggct cgaggcgact gaggagatct     960
acctgacccc agtgcagagg cccccagacc ctgcagaacc cacctccacc ttcttgccac    1020
ccactgagag ccggatgtct gtcagctcgg atcctgaccc tgccgcttac tctgtaactg    1080
```

-continued

```
cagggcgacc gcacccttcc atcagtgaag aggatgaggg cttcgactgt ctgtcatccc   1140
cagagcaagc tgagccacca ggtggagggt ggcggggaag cctcggggag ccaccaccgc   1200
ctccacgggc tcactgagc tcggacacca gcgcactgtc ctacgactct gtcaagtaca    1260
cactggtggt ggatgagcat gcccagcttg agttggtgag cctgcggcca tgttttggag   1320
attacagtga cgaaagcgac tctgccactg tctatgacaa ctgtgcctct gcctcctcgc   1380
cctacgagtc agccattggt gaggaatatg aggaggcccc tcaaccccgg cctcccacct   1440
gcctgtcaga ggactccaca ccggatgagc ctgacgtcca cttctctaag aagtttctga   1500
atgtcttcat gagtggccgc tctcgttcct ccagtgccga gtcctttggg ctgttctcct   1560
gtgtcatcaa tggggaggag catgagcaaa cccatcgggc tatattcagg tttgtgcctc   1620
ggcatgaaga tgaacttgag ctggaagtgg acgaccctct gctggtggag ctgcaggcag   1680
aagactattg gtatgaggcc tataacatgc gcactggagc ccgtggtgtc tttcctgcct   1740
actatgccat tgaggtcacc aaggagcctg agcacatggc agcccttgcc aaaaacagcg   1800
actggattga ccagttccgg gtgaagttcc tgggctctgt ccaggttcct tatcacaagg   1860
gcaatgatgt cctctgtgct gctatgcaaa agatcgccac cacccgccgg ctcaccgtgc   1920
actttaaccc gccctccagc tgtgtccttg aaatcagcgt tagggggtgtc aagataggtg   1980
tcaaagctga tgaagctcag gaggccaagg gaaataaatg tagccacttt ttccagctaa   2040
aaaacatctc tttctgtggg taccatccaa agaacaacaa gtactttggg tttatcacta   2100
agcaccctgc tgaccaccgg tttgcctgcc atgtctttgt gtctgaagat tccaccaaag   2160
ccctggcaga gtctgtgggg cgtgcatttc agcagttcta caagcaattt gtggaatata   2220
cctgtcctac agaagatatc tacttggagt agcagcaacc cccctctctg cagcccctca   2280
gccccaggcc agtactagga cagctgactg ctgacaggat gttgtactgc cacgagagaa   2340
tgggggagtg agggctgttg gggtcggggg gcaggggttt gggagaggc agatgcagtt    2400
tattgtaata tatgggggtta gattaatcta tggaggacag tacaggctct ctcggggctg   2460
gggaagggca gggctggggt gggggtcagg catctggcca caagggggtc ccctagggac   2520
agaggcgctg caccatcctg ggcttgtttc atactagagg ccctggcttt ctggctcttg   2580
ggtcctgcct tgacaaagcc cagccacctg gaagtgtcac cttcccttgt ccacctcacc   2640
cagtgccctg agctcatgct gagcccaagc acctccgaag gactttccag taaggaaatg   2700
gcaacatgtg acagtgagac cctgttctca tctgtggggc tccggcagct ccgaccccca   2760
gcctggccag cacgctgacc ctggcaagct tgtgtgttca aagaaggaga gggccacagc   2820
aagccctgcc tgccagggaa ggttccctct cagctgcccc cagccaactg gtcactgtct   2880
tgtcacctgg ctactactat taaagtgcca tttcttgtct gaaaaaaaaa aaaaaaaaa    2940
aaaaaaactc gag                                                      2953
```

<210> SEQ ID NO 2
<211> LENGTH: 714
<212> TYPE: PRT
<213> ORGANISM: rattus

<400> SEQUENCE: 2

Met Ala Arg Leu Ser Pro Gly Met Ala Glu Arg Glu Ser Gly Leu Ser
 1               5                   10                  15

Gly Gly Ala Ala Ser Pro Pro Ala Ala Ser Pro Phe Leu Gly Leu His
                20                  25                  30

Ile Ala Ser Pro Pro Asn Phe Arg Leu Thr His Asp Ile Ser Leu Glu

```
              35                    40                    45
Glu Phe Glu Asp Glu Asp Leu Ser Glu Ile Thr Asp Glu Cys Gly Ile
             50                    55                    60

Ser Leu Gln Cys Lys Asp Thr Leu Ser Leu Arg Pro Pro Arg Ala Gly
 65                    70                    75                    80

Leu Leu Ser Ala Gly Ser Ser Gly Ala Gly Ser Arg Leu Gln Ala
                  85                    90                    95

Glu Met Leu Gln Met Asp Leu Ile Asp Ala Ala Ser Asp Thr Pro Gly
                 100                   105                   110

Ala Glu Asp Glu Glu Asp Asp Glu Leu Ala Ala Gln Arg Pro
                 115                   120                   125

Gly Val Gly Pro Ser Lys Ala Glu Ser Gly Gln Glu Pro Ala Ser Arg
            130                   135                   140

Ser Gln Gly Gln Gly Gln Gly Pro Gly Thr Gly Cys Gly Asp Thr Tyr
145                   150                   155                   160

Arg Pro Lys Arg Pro Thr Thr Leu Asn Leu Phe Pro Gln Val Pro Arg
                 165                   170                   175

Ser Gln Asp Thr Leu Asn Asn Asn Ser Leu Gly Lys Lys His Ser Trp
                 180                   185                   190

Gln Asp Arg Val Ser Arg Ser Ser Pro Leu Lys Thr Gly Glu Gln
            195                   200                   205

Thr Pro Pro His Glu His Ile Cys Leu Ser Asp Glu Leu Pro Pro Gln
            210                   215                   220

Gly Ser Pro Val Pro Thr Gln Asp Arg Gly Thr Ser Thr Asp Ser Pro
225                   230                   235                   240

Cys Arg Arg Thr Ala Ala Thr Gln Met Ala Pro Pro Ser Gly Pro Pro
                 245                   250                   255

Ala Thr Ala Pro Gly Gly Arg Gly His Ser His Arg Asp Arg Ser Ile
                 260                   265                   270

Ser Ala Asp Val Arg Leu Glu Ala Thr Glu Glu Ile Tyr Leu Thr Pro
            275                   280                   285

Val Gln Arg Pro Pro Asp Pro Ala Glu Pro Thr Ser Thr Phe Leu Pro
            290                   295                   300

Pro Thr Glu Ser Arg Met Ser Val Ser Ser Asp Pro Asp Pro Ala Ala
305                   310                   315                   320

Tyr Ser Val Thr Ala Gly Arg Pro His Pro Ser Ile Ser Glu Glu Asp
                 325                   330                   335

Glu Gly Phe Asp Cys Leu Ser Ser Pro Glu Gln Ala Glu Pro Pro Gly
                 340                   345                   350

Gly Gly Trp Arg Gly Ser Leu Gly Glu Pro Pro Pro Pro Arg Ala
            355                   360                   365

Ser Leu Ser Ser Asp Thr Ser Ala Leu Ser Tyr Asp Ser Val Lys Tyr
370                   375                   380

Thr Leu Val Val Asp Glu His Ala Gln Leu Glu Leu Val Ser Leu Arg
385                   390                   395                   400

Pro Cys Phe Gly Asp Tyr Ser Asp Glu Ser Asp Ser Ala Thr Val Tyr
                 405                   410                   415

Asp Asn Cys Ala Ser Ala Ser Ser Pro Tyr Glu Ser Ala Ile Gly Glu
                 420                   425                   430

Glu Tyr Glu Glu Ala Pro Gln Pro Arg Pro Pro Thr Cys Leu Ser Glu
            435                   440                   445

Asp Ser Thr Pro Asp Glu Pro Asp Val His Phe Ser Lys Lys Phe Leu
450                   455                   460
```

-continued

```
Asn Val Phe Met Ser Gly Arg Ser Arg Ser Ser Ala Glu Ser Phe
465                 470                 475                 480

Gly Leu Phe Ser Cys Val Ile Asn Gly Glu Glu His Glu Gln Thr His
                485                 490                 495

Arg Ala Ile Phe Arg Phe Val Pro Arg His Glu Asp Glu Leu Glu Leu
                500                 505                 510

Glu Val Asp Asp Pro Leu Leu Val Glu Leu Gln Ala Glu Asp Tyr Trp
                515                 520                 525

Tyr Glu Ala Tyr Asn Met Arg Thr Gly Ala Arg Gly Val Phe Pro Ala
                530                 535                 540

Tyr Tyr Ala Ile Glu Val Thr Lys Glu Pro Glu His Met Ala Ala Leu
545                 550                 555                 560

Ala Lys Asn Ser Asp Trp Ile Asp Gln Phe Arg Val Lys Phe Leu Gly
                565                 570                 575

Ser Val Gln Val Pro Tyr His Lys Gly Asn Asp Val Leu Cys Ala Ala
                580                 585                 590

Met Gln Lys Ile Ala Thr Thr Arg Arg Leu Thr Val His Phe Asn Pro
                595                 600                 605

Pro Ser Ser Cys Val Leu Glu Ile Ser Val Arg Gly Val Lys Ile Gly
                610                 615                 620

Val Lys Ala Asp Glu Ala Gln Glu Ala Lys Gly Asn Lys Cys Ser His
625                 630                 635                 640

Phe Phe Gln Leu Lys Asn Ile Ser Phe Cys Gly Tyr His Pro Lys Asn
                645                 650                 655

Asn Lys Tyr Phe Gly Phe Ile Thr Lys His Pro Ala Asp His Arg Phe
                660                 665                 670

Ala Cys His Val Phe Val Ser Glu Asp Ser Thr Lys Ala Leu Ala Glu
                675                 680                 685

Ser Val Gly Arg Ala Phe Gln Gln Phe Tyr Lys Gln Phe Val Glu Tyr
                690                 695                 700

Thr Cys Pro Thr Glu Asp Ile Tyr Leu Glu
705                 710
```

<210> SEQ ID NO 3
<211> LENGTH: 2136
<212> TYPE: DNA
<213> ORGANISM: Homo sapiens

<400> SEQUENCE: 3

```
atggcggagc gagaaagcgg cggcctggga gggggggccg cgtccccgcc cgccgcctcc      60
ccgttcctgg ggctgcacat cgcttcgcct cccaatttca ggctcaccca tgacatcagc     120
ctggaggagt ttgaggatga agacctctcg agatcactg atgagtgtgg catcagctta     180
cagtgcaaag acaccctgtc cttacggccc ccgcgcgccg ggctgctctc tgcgggcggc     240
ggcggcgcgg ggagccggtt gcaggccgag atgctgcaga tggacctgat cgacgcgacg     300
ggggacactc ccgggccga ggacgacgag gaggacgacg acgaggagcg cgcggcccgg     360
cggccgggag cggggccgcc caaggccgag tccggccagg agccggcgtc ccgcggccag     420
ggccagagcc aaggccagag ccaggccccg gcagcggggg acacgtaccg gcccaagcgg     480
cccaccacgc tcaacctctt tccgcaggtg ccgcggtctc aggacacact gaataataat     540
tctctgggca aaaagcacag ttggcaggat cgggtgtctc gatcatcctc accccctgaag    600
acaggggagc agacaccacc gcatgaacac atctgcctga gcgatgagct gccccccag     660
```

-continued

| | |
|---|---|
| agcggccccg ccccaccac agatcgaggc acctccaccg acagcccttg ccgccgcagc | 720 |
| acagccaccc agatggcacc tccgggtggt cccctgctg cccgcctgg ggtcggggc | 780 |
| cactcgcatc gagaccgaat ccactaccag gccgatgtgc gactagaggc cactgaggag | 840 |
| attaacctga ccccagtgca gaggccccca gacgctgcag agcccacctc cgccttcctg | 900 |
| ccgcccactg agagccggat gtcagtcagt tccgatccag accctgccgc ctaccctcc | 960 |
| acggcagggc ggccgcaccc ctccatcagt gaagaggaag agggcttcga ctgcctgtcg | 1020 |
| tccccagagc gggctgagcc cccaggcgga gggtggcggg ggagcctggg ggagccgccg | 1080 |
| ccacctccac gggcctctct gagctcggac accagcgccc tgtcctatga ctctgtcaag | 1140 |
| tacacgctgg tggtagatga gcatgcacag ctggagctgg tgagcctgcg gccgtgcttc | 1200 |
| ggagactaca gtgacgagag tgactctgcc accgtctatg acaactgtgc ctccgtctcc | 1260 |
| tcgccctatg agtcggccat cggagaggaa tatgaggagg cccgcggcc ccagcccct | 1320 |
| gcctgcctct ccgaggactc cacgcctgat gaacccgacg tccatttctc caagaaattc | 1380 |
| ctgaacgtct tcatgagtgg ccgctcccgc tcctccagtg ctgagtcctt cgggctgttc | 1440 |
| tcctgcatca tcaacgggga ggagcaggag cagacccacc gggccatatt caggtttgtg | 1500 |
| cctcgacacg aagacgaact tgagctgaa gtggatgacc ctctgctagt ggagctccag | 1560 |
| gctgaagact actggtacga ggcctacaac atgcgcactg gtgcccgggg tgtctttcct | 1620 |
| gcctattacg ccatcgaggt caccaaggag cccgagcaca tggcagccct ggccaaaaac | 1680 |
| agtgactggg tggaccagtt ccgggtgaag ttcctgggct cagtccaggt tcctatcac | 1740 |
| aagggcaatg acgtcctctg tgctgctatg caaaagattg ccaccacccg ccggctcacc | 1800 |
| gtgcacttta acccgccctc cagctgtgtc ctggagatca gcgtgcgggg tgtgaagata | 1860 |
| ggcgtcaagg ccgatgactc ccaggaggcc aaggggaata aatgtagcca ctttttccag | 1920 |
| ttaaaaaaca tctcttctg cggatatcat ccaaagaaca caagtactt tgggttcatc | 1980 |
| accaagcacc ccgccgacca ccggtttgcc tgccacgtct tgtgtctga agactccacc | 2040 |
| aaagccctgg cagagtccgt ggggagagca ttccagcagt tctacaagca gtttgtggag | 2100 |
| tacacctgcc ccacagaaga tatctacctg gagtag | 2136 |

<210> SEQ ID NO 4
<211> LENGTH: 711
<212> TYPE: PRT
<213> ORGANISM: Homo sapiens

<400> SEQUENCE: 4

Met Ala Glu Arg Glu Ser Gly Gly Leu Gly Gly Gly Ala Ala Ser Pro
 1               5                  10                  15

Pro Ala Ala Ser Pro Phe Leu Gly Leu His Ile Ala Ser Pro Pro Asn
                20                  25                  30

Phe Arg Leu Thr His Asp Ile Ser Leu Glu Glu Phe Glu Asp Glu Asp
            35                  40                  45

Leu Ser Glu Ile Thr Asp Glu Cys Gly Ile Ser Leu Gln Cys Lys Asp
        50                  55                  60

Thr Leu Ser Leu Arg Pro Pro Arg Ala Gly Leu Leu Ser Ala Gly Gly
65                  70                  75                  80

Gly Gly Ala Gly Ser Arg Leu Gln Ala Glu Met Leu Gln Met Asp Leu
                85                  90                  95

Ile Asp Ala Thr Gly Asp Thr Pro Gly Ala Glu Asp Asp Glu Glu Asp
            100                 105                 110

-continued

```
Asp Asp Glu Glu Arg Ala Ala Arg Arg Pro Gly Ala Gly Pro Pro Lys
        115                 120                 125

Ala Glu Ser Gly Gln Glu Pro Ala Ser Arg Gly Gln Gly Gln Ser Gln
    130                 135                 140

Gly Gln Ser Gln Gly Pro Gly Ser Gly Asp Thr Tyr Arg Pro Lys Arg
145                 150                 155                 160

Pro Thr Thr Leu Asn Leu Phe Pro Gln Val Pro Arg Ser Gln Asp Thr
                165                 170                 175

Leu Asn Asn Asn Ser Leu Gly Lys Lys His Ser Trp Gln Asp Arg Val
            180                 185                 190

Ser Arg Ser Ser Ser Pro Leu Lys Thr Gly Glu Gln Thr Pro Pro His
        195                 200                 205

Glu His Ile Cys Leu Ser Asp Glu Leu Pro Pro Gln Ser Gly Pro Ala
    210                 215                 220

Pro Thr Thr Asp Arg Gly Thr Ser Thr Asp Ser Pro Cys Arg Arg Ser
225                 230                 235                 240

Thr Ala Thr Gln Met Ala Pro Pro Gly Gly Pro Pro Ala Ala Pro Pro
                245                 250                 255

Gly Gly Arg Gly His Ser His Arg Asp Arg Ile His Tyr Gln Ala Asp
            260                 265                 270

Val Arg Leu Glu Ala Thr Glu Glu Ile Asn Leu Thr Pro Val Gln Arg
        275                 280                 285

Pro Pro Asp Ala Ala Glu Pro Thr Ser Ala Phe Leu Pro Pro Thr Glu
    290                 295                 300

Ser Arg Met Ser Val Ser Ser Asp Pro Asp Pro Ala Ala Tyr Pro Ser
305                 310                 315                 320

Thr Ala Gly Arg Pro His Pro Ser Ile Ser Glu Glu Glu Glu Gly Phe
                325                 330                 335

Asp Cys Leu Ser Ser Pro Glu Arg Ala Glu Pro Pro Gly Gly Gly Trp
            340                 345                 350

Arg Gly Ser Leu Gly Glu Pro Pro Pro Pro Arg Ala Ser Leu Ser
        355                 360                 365

Ser Asp Thr Ser Ala Leu Ser Tyr Asp Ser Val Lys Tyr Thr Leu Val
    370                 375                 380

Val Asp Glu His Ala Gln Leu Glu Leu Val Ser Leu Arg Pro Cys Phe
385                 390                 395                 400

Gly Asp Tyr Ser Asp Glu Ser Asp Ser Ala Thr Val Tyr Asp Asn Cys
                405                 410                 415

Ala Ser Val Ser Ser Pro Tyr Glu Ser Ala Ile Gly Glu Glu Tyr Glu
            420                 425                 430

Glu Ala Pro Arg Pro Gln Pro Ala Cys Leu Ser Glu Asp Ser Thr
        435                 440                 445

Pro Asp Glu Pro Asp Val His Phe Ser Lys Lys Phe Leu Asn Val Phe
    450                 455                 460

Met Ser Gly Arg Ser Arg Ser Ser Ser Ala Glu Ser Phe Gly Leu Phe
465                 470                 475                 480

Ser Cys Ile Ile Asn Gly Glu Glu Gln Thr His Arg Ala Ile
                485                 490                 495

Phe Arg Phe Val Pro Arg His Glu Asp Glu Leu Glu Leu Glu Val Asp
            500                 505                 510

Asp Pro Leu Leu Val Glu Leu Gln Ala Glu Asp Tyr Trp Tyr Glu Ala
        515                 520                 525

Tyr Asn Met Arg Thr Gly Ala Arg Gly Val Phe Pro Ala Tyr Tyr Ala
```

```
                530             535             540
Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
                565                 570                 575

Val Pro Tyr His Lys Gly Asn Asp Val Leu Cys Ala Ala Met Gln Lys
                580                 585                 590

Ile Ala Thr Thr Arg Arg Leu Thr Val His Phe Asn Pro Pro Ser Ser
                595                 600                 605

Cys Val Leu Glu Ile Ser Val Arg Gly Val Lys Ile Gly Val Lys Ala
                610                 615                 620

Asp Asp Ser Gln Glu Ala Lys Gly Asn Lys Cys Ser His Phe Gln
625                 630                 635                 640

Leu Lys Asn Ile Ser Phe Cys Gly Tyr His Pro Lys Asn Asn Lys Tyr
                645                 650                 655

Phe Gly Phe Ile Thr Lys His Pro Ala Asp His Arg Phe Ala Cys His
                660                 665                 670

Val Phe Val Ser Glu Asp Ser Thr Lys Ala Leu Ala Glu Ser Val Gly
                675                 680                 685

Arg Ala Phe Gln Gln Phe Tyr Lys Gln Phe Val Glu Tyr Thr Cys Pro
690                 695                 700

Thr Glu Asp Ile Tyr Leu Glu
705                 710

<210> SEQ ID NO 5
<211> LENGTH: 30
<212> TYPE: PRT
<213> ORGANISM: Homo sapiens

<400> SEQUENCE: 5

Arg Thr Gly Ala Arg Gly Val Phe Pro Ala Tyr Tyr Ala Ile Glu Val
1               5                   10                  15

Thr Lys Glu Pro Glu His Met Ala Ala Leu Ala Lys Asn Ser
                20                  25                  30

<210> SEQ ID NO 6
<211> LENGTH: 17
<212> TYPE: PRT
<213> ORGANISM: Homo sapiens

<400> SEQUENCE: 6

Lys Gly Asn Asp Val Leu Cys Ala Ala Met Gln Lys Ile Ala Thr Thr
1               5                   10                  15

Arg

<210> SEQ ID NO 7
<211> LENGTH: 29
<212> TYPE: PRT
<213> ORGANISM: Homo sapiens

<400> SEQUENCE: 7

Arg Glu Arg Arg Met Ala Asn Asn Ala Arg Glu Arg Leu Arg Val Arg
1               5                   10                  15

Asp Ile Asn Glu Ala Phe Arg Glu Leu Gly Arg Met Cys
                20                  25

<210> SEQ ID NO 8
<211> LENGTH: 16
```

```
<212> TYPE: PRT
<213> ORGANISM: Homo sapiens

<400> SEQUENCE: 8

Lys Leu Leu Ile Leu Gln Gln Ala Val Gln Val Ile Leu Gly Leu Glu
 1               5                  10                  15

<210> SEQ ID NO 9
<211> LENGTH: 29
<212> TYPE: PRT
<213> ORGANISM: Homo sapiens

<400> SEQUENCE: 9

Ala Asp Arg Arg Lys Ala Ala Thr Met Arg Glu Arg Arg Arg Leu Ser
 1               5                  10                  15

Lys Val Asn Glu Ala Phe Glu Thr Leu Lys Arg Cys Thr
            20                  25

<210> SEQ ID NO 10
<211> LENGTH: 16
<212> TYPE: PRT
<213> ORGANISM: Homo sapiens

<400> SEQUENCE: 10

Lys Val Glu Ile Leu Arg Asn Ala Ile Arg Tyr Ile Glu Gly Leu Gln
 1               5                  10                  15

<210> SEQ ID NO 11
<211> LENGTH: 29
<212> TYPE: PRT
<213> ORGANISM: Homo sapiens

<400> SEQUENCE: 11

Asn Val Lys Arg Arg Thr His Asn Val Leu Glu Arg Gln Arg Arg Asn
 1               5                  10                  15

Glu Leu Lys Arg Ser Phe Phe Ala Leu Arg Asp Gln Ile
            20                  25

<210> SEQ ID NO 12
<211> LENGTH: 16
<212> TYPE: PRT
<213> ORGANISM: Homo sapiens

<400> SEQUENCE: 12

Lys Val Val Ile Leu Lys Lys Ala Thr Ala Tyr Ile Leu Ser Val Gln
 1               5                  10                  15

<210> SEQ ID NO 13
<211> LENGTH: 29
<212> TYPE: PRT
<213> ORGANISM: Homo sapiens

<400> SEQUENCE: 13

Lys Glu Arg Arg Val Ala Asn Asn Ala Arg Glu Arg Leu Arg Val Arg
 1               5                  10                  15

Asp Ile Asn Glu Ala Phe Lys Glu Leu Gly Arg Met Cys
            20                  25

<210> SEQ ID NO 14
<211> LENGTH: 16
<212> TYPE: PRT
<213> ORGANISM: Homo sapiens

<400> SEQUENCE: 14
```

```
Lys Leu Leu Ile Leu His Gln Ala Val Ser Val Ile Leu Asn Leu Glu
 1               5                  10                  15
```

<210> SEQ ID NO 15
<211> LENGTH: 29
<212> TYPE: PRT
<213> ORGANISM: Homo sapiens

<400> SEQUENCE: 15

```
Arg Glu Arg Arg Met Ala Asn Asn Ala Arg Glu Arg Val Arg Val Arg
 1               5                  10                  15

Asp Ile Asn Glu Ala Phe Arg Glu Leu Gly Arg Met Cys
            20                  25
```

<210> SEQ ID NO 16
<211> LENGTH: 16
<212> TYPE: PRT
<213> ORGANISM: Homo sapiens

<400> SEQUENCE: 16

```
Lys Leu Leu Ile Leu Gln Gln Ala Val Gln Val Ile Leu Gly Leu Glu
 1               5                  10                  15
```

<210> SEQ ID NO 17
<211> LENGTH: 711
<212> TYPE: PRT
<213> ORGANISM: Homo sapiens

<400> SEQUENCE: 17

```
Met Ala Glu Arg Glu Ser Gly Gly Leu Gly Gly Gly Ala Ala Ser Pro
 1               5                  10                  15

Pro Ala Ala Ser Pro Phe Leu Gly Leu His Ile Ala Ser Pro Pro Asn
            20                  25                  30

Phe Arg Leu Thr His Asp Ile Ser Leu Glu Glu Phe Glu Asp Glu Asp
        35                  40                  45

Leu Ser Glu Ile Thr Asp Glu Cys Gly Ile Ser Leu Gln Cys Lys Asp
    50                  55                  60

Thr Leu Ser Leu Arg Pro Pro Arg Ala Gly Leu Leu Ser Ala Gly Gly
65                  70                  75                  80

Gly Gly Ala Gly Ser Arg Leu Gln Ala Glu Met Leu Gln Met Asp Leu
                85                  90                  95

Ile Asp Ala Thr Gly Asp Thr Pro Gly Ala Glu Asp Asp Glu Glu Asp
            100                 105                 110

Asp Asp Glu Glu Arg Ala Ala Arg Arg Pro Gly Ala Gly Pro Pro Lys
        115                 120                 125

Ala Glu Ser Gly Gln Glu Pro Ala Ser Arg Gly Gln Gly Gln Ser Gln
    130                 135                 140

Gly Gln Ser Gln Gly Pro Gly Ser Gly Asp Thr Tyr Arg Pro Lys Arg
145                 150                 155                 160

Pro Thr Thr Leu Asn Leu Phe Pro Gln Val Pro Arg Ser Gln Asp Thr
                165                 170                 175

Leu Asn Asn Asn Ser Leu Gly Lys Lys His Ser Trp Gln Asp Arg Val
            180                 185                 190

Ser Arg Ser Ser Pro Leu Lys Thr Gly Glu Gln Thr Pro Pro His
        195                 200                 205

Glu His Ile Cys Leu Ser Asp Glu Leu Pro Pro Gln Ser Gly Pro Ala
    210                 215                 220
```

-continued

```
Pro Thr Thr Asp Arg Gly Thr Thr Asp Ser Pro Cys Arg Arg Ser
225                 230                 235                 240

Thr Ala Thr Gln Met Ala Pro Pro Gly Gly Pro Pro Ala Ala Pro Pro
            245                 250                 255

Gly Gly Arg Gly His Ser His Arg Asp Arg Ile His Tyr Gln Ala Asp
            260                 265                 270

Val Arg Leu Glu Ala Thr Glu Glu Ile Tyr Leu Thr Pro Val Gln Arg
            275                 280                 285

Pro Pro Asp Ala Ala Glu Pro Thr Ser Ala Phe Leu Pro Pro Thr Glu
    290                 295                 300

Ser Arg Met Ser Val Ser Ser Asp Pro Asp Pro Ala Ala Tyr Pro Ser
305                 310                 315                 320

Thr Ala Gly Arg Pro His Pro Ser Ile Ser Glu Glu Glu Gly Phe
            325                 330                 335

Asp Cys Leu Ser Ser Pro Glu Arg Ala Glu Pro Pro Gly Gly Gly Trp
            340                 345                 350

Arg Gly Ser Leu Gly Glu Pro Pro Pro Pro Arg Ala Ser Leu Ser
            355                 360                 365

Ser Asp Thr Ser Ala Leu Ser Tyr Asp Ser Val Lys Tyr Thr Leu Val
            370                 375                 380

Val Asp Glu His Ala Gln Leu Glu Leu Val Ser Leu Arg Pro Cys Phe
385                 390                 395                 400

Gly Asp Tyr Ser Asp Glu Ser Asp Ser Ala Thr Val Tyr Asp Asn Cys
            405                 410                 415

Ala Ser Val Ser Ser Pro Tyr Glu Ser Ala Ile Gly Glu Glu Tyr Glu
            420                 425                 430

Glu Ala Pro Arg Pro Gln Pro Ala Cys Leu Ser Glu Asp Ser Thr
            435                 440                 445

Pro Asp Glu Pro Asp Val His Phe Ser Lys Lys Phe Leu Asn Val Phe
    450                 455                 460

Met Ser Gly Arg Ser Arg Ser Ser Ser Ala Glu Ser Phe Gly Leu Phe
465                 470                 475                 480

Ser Cys Ile Ile Asn Gly Glu Glu Gln Glu Gln Thr His Arg Ala Ile
            485                 490                 495

Phe Arg Phe Val Pro Arg His Glu Asp Glu Leu Glu Leu Glu Val Asp
            500                 505                 510

Asp Pro Leu Leu Val Glu Leu Gln Ala Glu Asp Tyr Trp Tyr Glu Ala
            515                 520                 525

Tyr Asn Met Arg Thr Gly Ala Arg Gly Val Phe Pro Ala Tyr Tyr Ala
            530                 535                 540

Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
            565                 570                 575

Val Pro Tyr His Lys Gly Asn Asp Val Leu Cys Ala Ala Met Gln Lys
            580                 585                 590

Ile Ala Thr Thr Arg Arg Leu Thr Val His Phe Asn Pro Pro Ser Ser
            595                 600                 605

Cys Val Leu Glu Ile Ser Val Arg Gly Val Lys Ile Gly Val Lys Ala
            610                 615                 620

Asp Asp Ser Gln Glu Ala Lys Gly Asn Lys Cys Ser His Phe Phe Gln
625                 630                 635                 640

Leu Lys Asn Ile Ser Phe Cys Gly Tyr His Pro Lys Asn Asn Lys Tyr
```

```
                    645                 650                 655
Phe Gly Phe Ile Thr Lys His Pro Ala Asp His Arg Phe Ala Cys His
            660                 665                 670

Val Phe Val Ser Glu Asp Ser Thr Lys Ala Leu Ala Glu Ser Val Gly
        675                 680                 685

Arg Ala Phe Gln Gln Phe Tyr Lys Gln Phe Val Glu Tyr Thr Cys Pro
    690                 695                 700

Thr Glu Asp Ile Tyr Leu Glu
705                 710

<210> SEQ ID NO 18
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 18
gaccacgcgt atcgatgtcg actttttttt ttttttttv                          39

<210> SEQ ID NO 19
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 19
gaccacgcgt atcgatgtcg ac                                            22

<210> SEQ ID NO 20
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 20
atcaggtcca tctgcagcat ctc                                           23

<210> SEQ ID NO 21
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 21
gcaagggctg tcggtggagg tgcctcga                                      28

<210> SEQ ID NO 22
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 22
tccatctgca tctcggcct                                                19

<210> SEQ ID NO 23
<211> LENGTH: 17
<212> TYPE: DNA
<213> ORGANISM: Artificial Sequence
```

```
<220> FEATURE:
<223> OTHER INFORMATION: Synthetic Sequence

<400> SEQUENCE: 23
ggacagggtg tctttgc                                                    17

<210> SEQ ID NO 24
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 24
gggcagctca tcgctcaggc a                                               21

<210> SEQ ID NO 25
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 25
gttcatgcgg tggtgtctgc t                                               21

<210> SEQ ID NO 26
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 26
catcgagacc gaatccac                                                   18

<210> SEQ ID NO 27
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 27
gttcaggaat ttcttggaga aatg                                            24

<210> SEQ ID NO 28
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 28
tgatgaaccc gacgtccat                                                  19

<210> SEQ ID NO 29
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 29
accagtgcgc atgttgtagg                                                 20
```

```
<210> SEQ ID NO 30
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 30
cctgccttca tgacctgcct g                                           21

<210> SEQ ID NO 31
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 31
ggattcggtc tcgatgcgag                                             20

<210> SEQ ID NO 32
<211> LENGTH: 31
<212> TYPE: DNA
<213> ORGANISM: Homo sapiens

<400> SEQUENCE: 32
caatttcagg tgagagtccc cggccgccgc g                                31

<210> SEQ ID NO 33
<211> LENGTH: 31
<212> TYPE: DNA
<213> ORGANISM: Rattus

<400> SEQUENCE: 33
tttggcttcc tgtccccacc aggctcaccc a                                31

<210> SEQ ID NO 34
<211> LENGTH: 31
<212> TYPE: DNA
<213> ORGANISM: Homo sapiens

<400> SEQUENCE: 34
tccttacggg taagggcaag ctcccaggag c                                31

<210> SEQ ID NO 35
<211> LENGTH: 31
<212> TYPE: DNA
<213> ORGANISM: Rattus

<400> SEQUENCE: 35
cgcccctccg tgcgctgtgc agcccccgcg c                                31

<210> SEQ ID NO 36
<211> LENGTH: 31
<212> TYPE: DNA
<213> ORGANISM: Homo sapiens

<400> SEQUENCE: 36
cggtctcagg tgaggcgcca acgtgggggg c                                31

<210> SEQ ID NO 37
<211> LENGTH: 31
<212> TYPE: DNA
<213> ORGANISM: Rattus
```

<400> SEQUENCE: 37
gagccttttg ttccctgcac aggacacact g                                  31

<210> SEQ ID NO 38
<211> LENGTH: 31
<212> TYPE: DNA
<213> ORGANISM: Homo sapiens

<400> SEQUENCE: 38
tgaagacagg taagtcaggg ccctcttcct t                                  31

<210> SEQ ID NO 39
<211> LENGTH: 31
<212> TYPE: DNA
<213> ORGANISM: Rattus

<400> SEQUENCE: 39
tcatgacctg cctgctctcc agggagcag a                                   31

<210> SEQ ID NO 40
<211> LENGTH: 31
<212> TYPE: DNA
<213> ORGANISM: Homo sapiens

<400> SEQUENCE: 40
gctcctccag tgagtcagca aggggaagca g                                  31

<210> SEQ ID NO 41
<211> LENGTH: 31
<212> TYPE: DNA
<213> ORGANISM: Rattus

<400> SEQUENCE: 41
agccacacca cctcacctgc aggtgctgag t                                  31

<210> SEQ ID NO 42
<211> LENGTH: 31
<212> TYPE: DNA
<213> ORGANISM: Homo sapiens

<400> SEQUENCE: 42
catattcagg tgagagccat gggctggctg g                                  31

<210> SEQ ID NO 43
<211> LENGTH: 31
<212> TYPE: DNA
<213> ORGANISM: Rattus

<400> SEQUENCE: 43
cacctgtcct tgctggggac aggtttgtgc c                                  31

<210> SEQ ID NO 44
<211> LENGTH: 31
<212> TYPE: DNA
<213> ORGANISM: Homo sapiens

<400> SEQUENCE: 44
acatggcagg tagtgttccc tccctggcct g                                  31

<210> SEQ ID NO 45
<211> LENGTH: 31
<212> TYPE: DNA

<213> ORGANISM: Rattus

<400> SEQUENCE: 45
tcaattcacg cttgctttcc agccctggcc a        31

<210> SEQ ID NO 46
<211> LENGTH: 31
<212> TYPE: DNA
<213> ORGANISM: Homo sapiens

<400> SEQUENCE: 46
atgcaaaagg tacctgagcc ctctcccttc t        31

<210> SEQ ID NO 47
<211> LENGTH: 31
<212> TYPE: DNA
<213> ORGANISM: Rattus

<400> SEQUENCE: 47
tggctccatt tgtcacctgt agattgccac c        31

<210> SEQ ID NO 48
<211> LENGTH: 31
<212> TYPE: DNA
<213> ORGANISM: Homo sapiens

<400> SEQUENCE: 48
gaggccaagg tgacttcttc caacccagcc c        31

<210> SEQ ID NO 49
<211> LENGTH: 31
<212> TYPE: DNA
<213> ORGANISM: Rattus

<400> SEQUENCE: 49
gcttcttttc tccctcctgt agggaataa a         31

<210> SEQ ID NO 50
<211> LENGTH: 31
<212> TYPE: DNA
<213> ORGANISM: Homo sapiens

<400> SEQUENCE: 50
gaacaacaag taagtggggg tgggatggca g        31

<210> SEQ ID NO 51
<211> LENGTH: 31
<212> TYPE: DNA
<213> ORGANISM: Rattus

<400> SEQUENCE: 51
acagacagac ctgtccctgc aggtactttg g        31

<210> SEQ ID NO 52
<211> LENGTH: 31
<212> TYPE: DNA
<213> ORGANISM: Homo sapiens

<400> SEQUENCE: 52
gtccgtgggg tacgtgtaca ccctgctgag c        31

<210> SEQ ID NO 53
<211> LENGTH: 31

```
<212> TYPE: DNA
<213> ORGANISM: Rattus

<400> SEQUENCE: 53
ctgtgtgtcc cctggcttct aggagagcat t                                    31

<210> SEQ ID NO 54
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 54
gtaaagggtg tattgattgg attaccatca atactcagct tct                       43

<210> SEQ ID NO 55
<211> LENGTH: 46
<212> TYPE: DNA
<213> ORGANISM: Artificial Sequence
<220> FEATURE:
<223> OTHER INFORMATION: Synthetic Sequence

<400> SEQUENCE: 55
gatctggaaa ctgcagcttc agccctctg gccatctgct gatccg                    46
```